(12) United States Patent
Fish et al.

(10) Patent No.: US 7,776,313 B2
(45) Date of Patent: Aug. 17, 2010

(54) METHODS OF DIAGNOSING AND TREATING RHEUMATOID ARTHRITIS AND OSTEOARTHRITIS

(75) Inventors: Eleanor Fish, Toronto (CA); Carole Galligan, Scarborough (CA); Kathy Siminovitch, Toronto (CA); Omar Perez, San Francisco, CA (US); Edward Keystone, Toronto (CA); Vivian Bykerk, Toronto (CA)

(73) Assignees: University Health Network, Ontario (CA); The Board of Trustees of the Leland Stanford Junior University, Palo Alto, CA (US)

( * ) Notice: Subject to any disclaimer, the term of this patent is extended or adjusted under 35 U.S.C. 154(b) by 167 days.

(21) Appl. No.: 11/807,088

(22) Filed: May 25, 2007

(65) Prior Publication Data

US 2007/0292881 A1 Dec. 20, 2007

Related U.S. Application Data

(60) Provisional application No. 60/808,294, filed on May 25, 2006.

(51) Int. Cl.
*A61K 49/00* (2006.01)

(52) U.S. Cl. ...................................................... 424/9.1
(58) Field of Classification Search ....................... None
See application file for complete search history.

(56) References Cited

OTHER PUBLICATIONS

Verschueren et al. "Detection, identification and evaluation of in vivo anti-TNF responsiveness of a BMP activated stromal precursor cell population in the human RA synovium", Arthritis Rheum. 2005, 52(s):S474.*

\* cited by examiner

*Primary Examiner*—Karen Cochrane Carlson
*Assistant Examiner*—Bin Shen
(74) *Attorney, Agent, or Firm*—Fulbright & Jaworski

(57) ABSTRACT

The invention provides a novel cell that is a precursor of a fibroblast-like synovial cell. The novel cell is a circulating synovial tissue cell that stains positive for collagen, CD34, CD45, prolyl 4-hydroxylase and CD14. The invention also relates to methods of diagnosing or monitoring rheumatoid arthritis and/or osteoarthritis using gene expression profiles, protein expression profiles, and/or protein phosphorylation profiles of different cell types, including the novel precursor, CD3+ cells, synovial tissue fibroblast-like synovial cells and fibrocytes. The invention also includes methods to identify substances to treat or prevent rheumatoid arthritis and/or osteoarthritis.

6 Claims, 18 Drawing Sheets
(16 of 18 Drawing Sheet(s) Filed in Color)

Gene expression levels in ST FLS cells: Affymetrix analysis

Representative heat maps of phospho-protein signature profiles

Signature protein expression in RA ST FLS cells

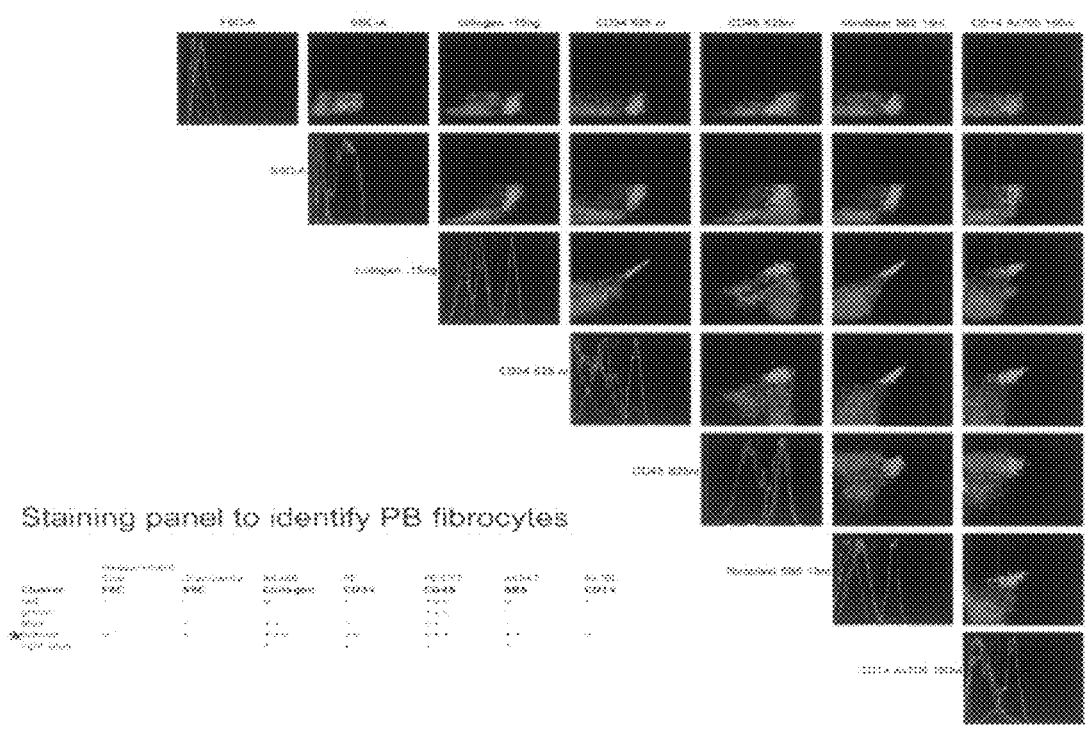

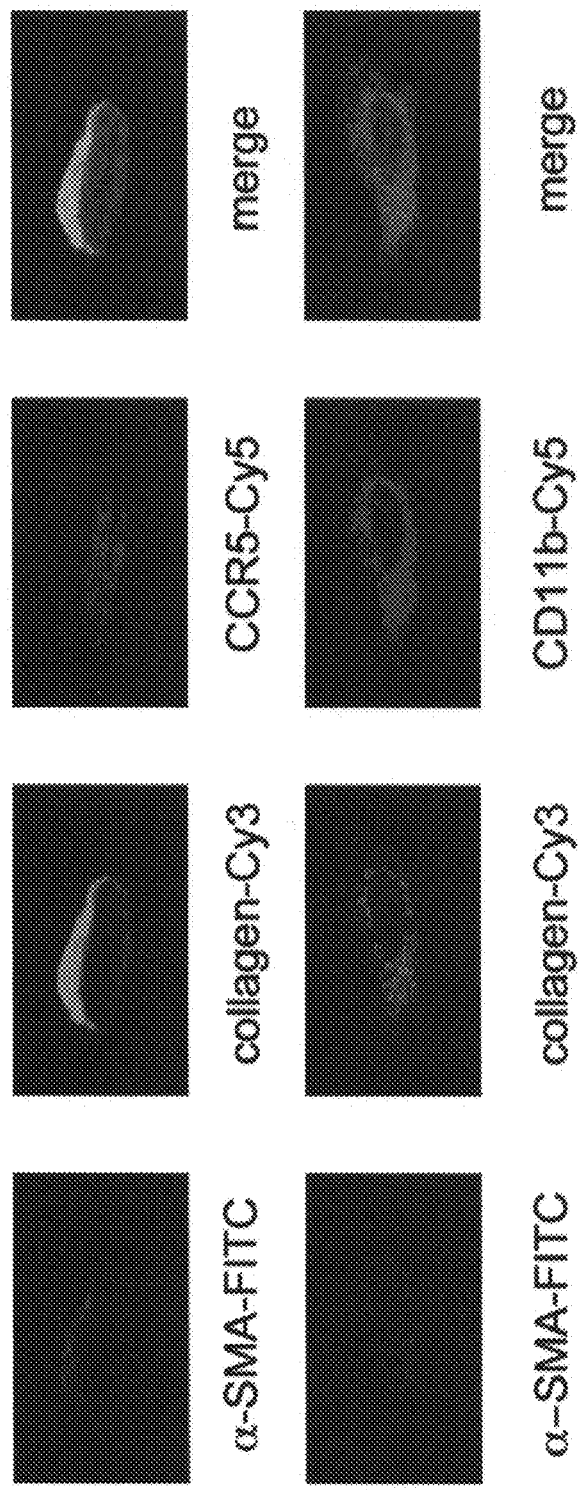

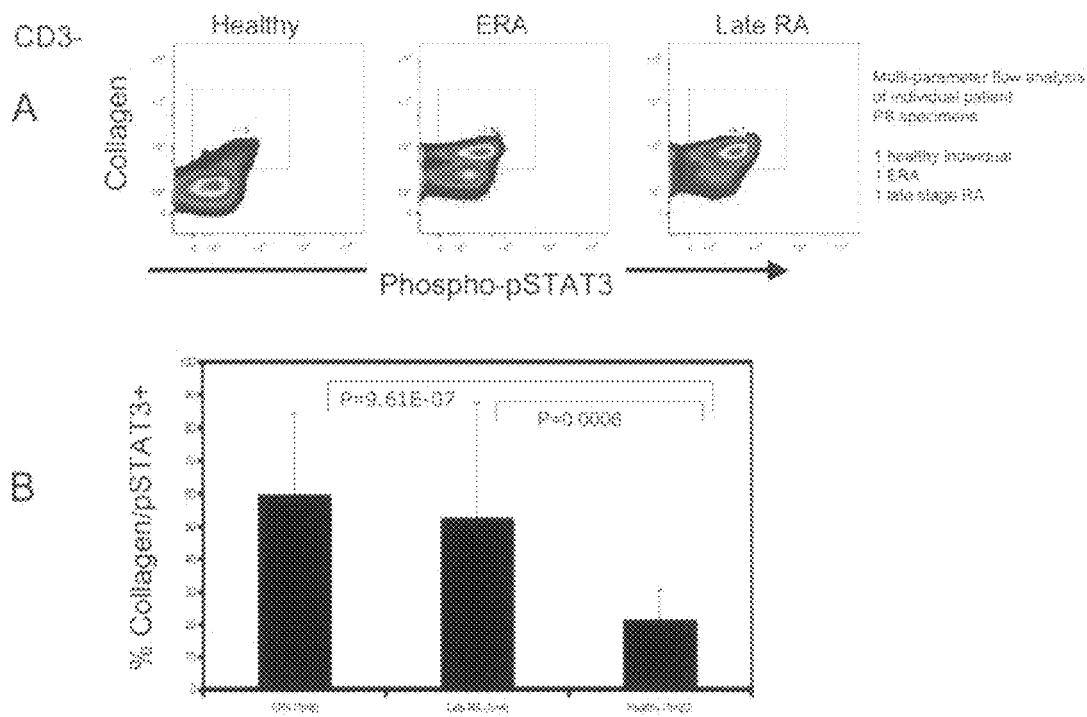

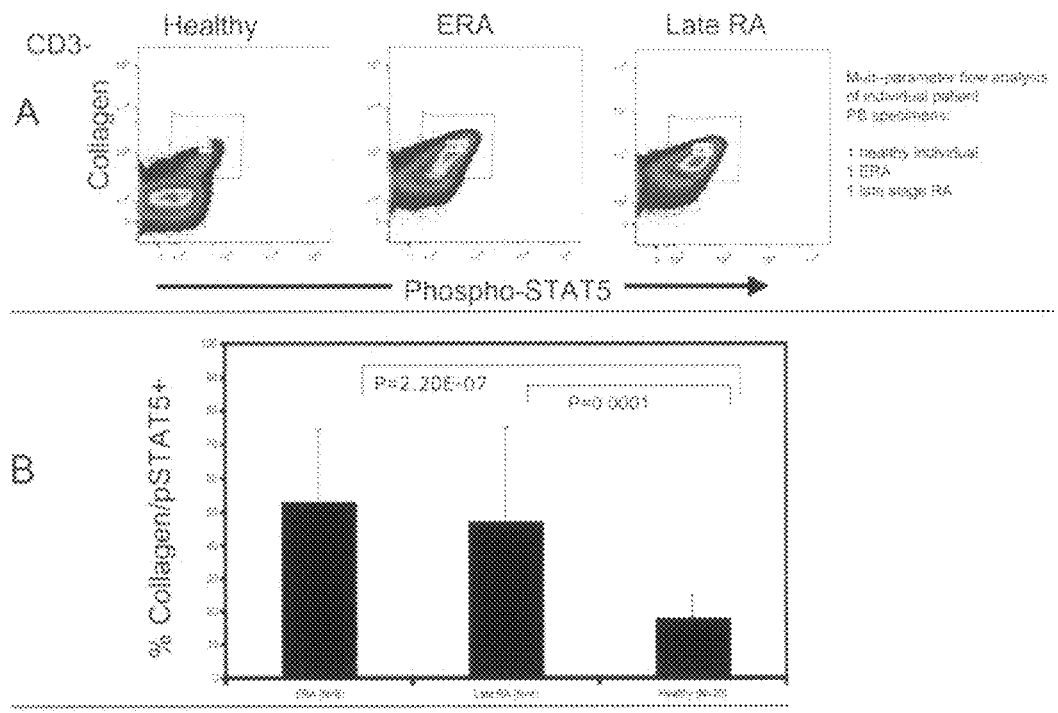

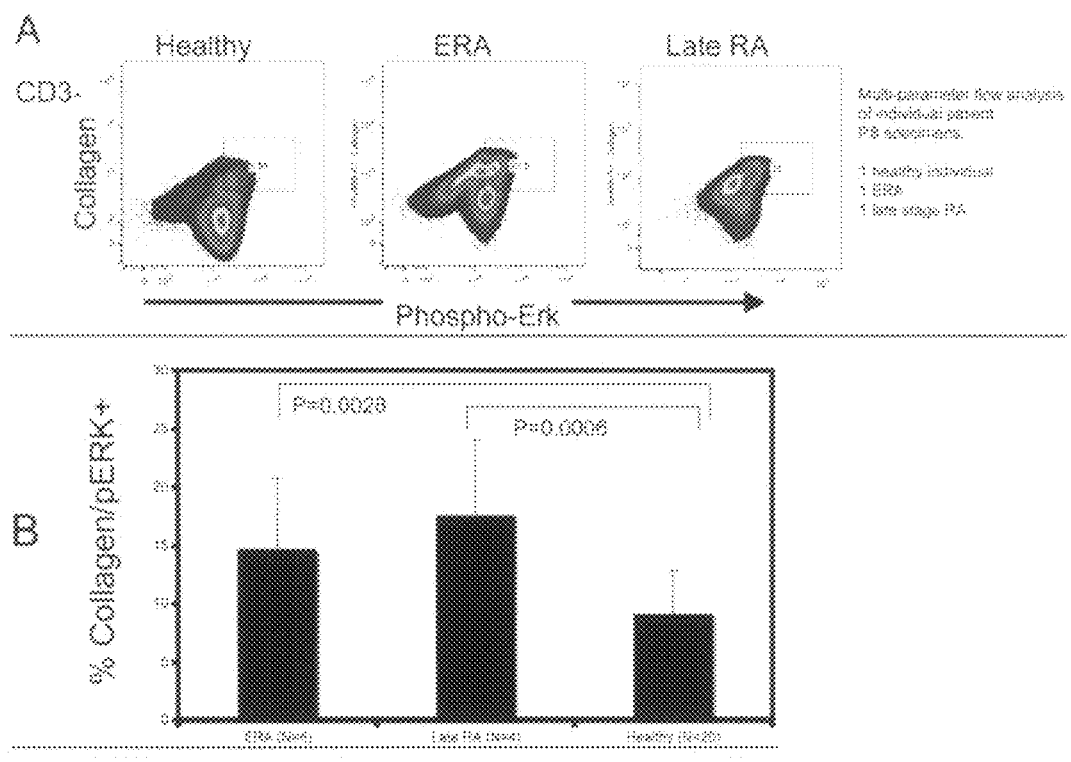

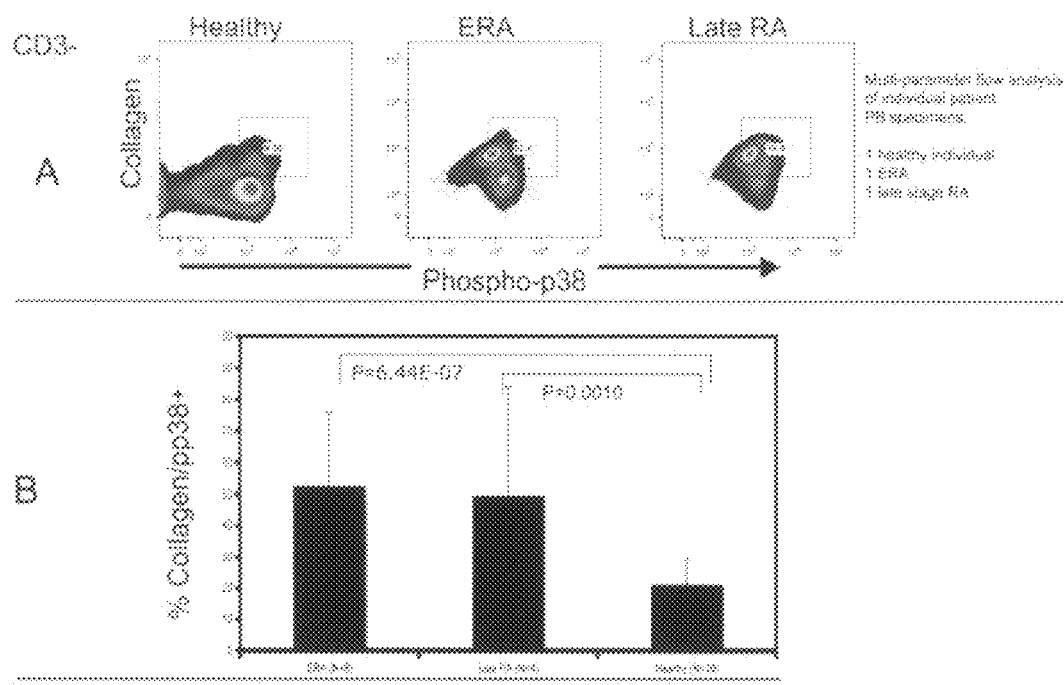

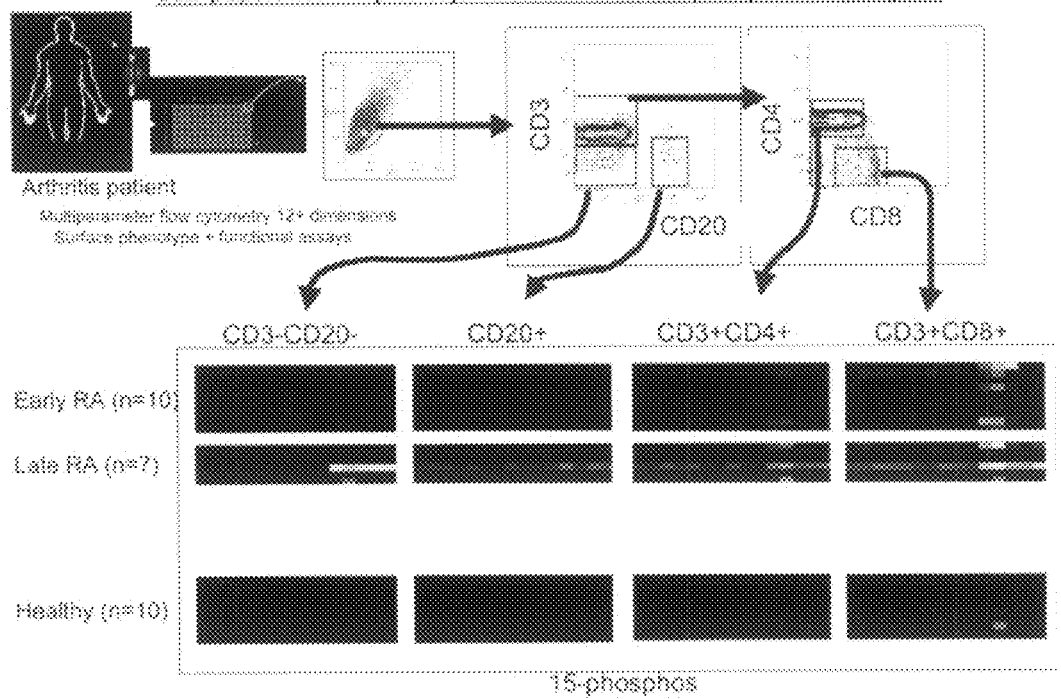

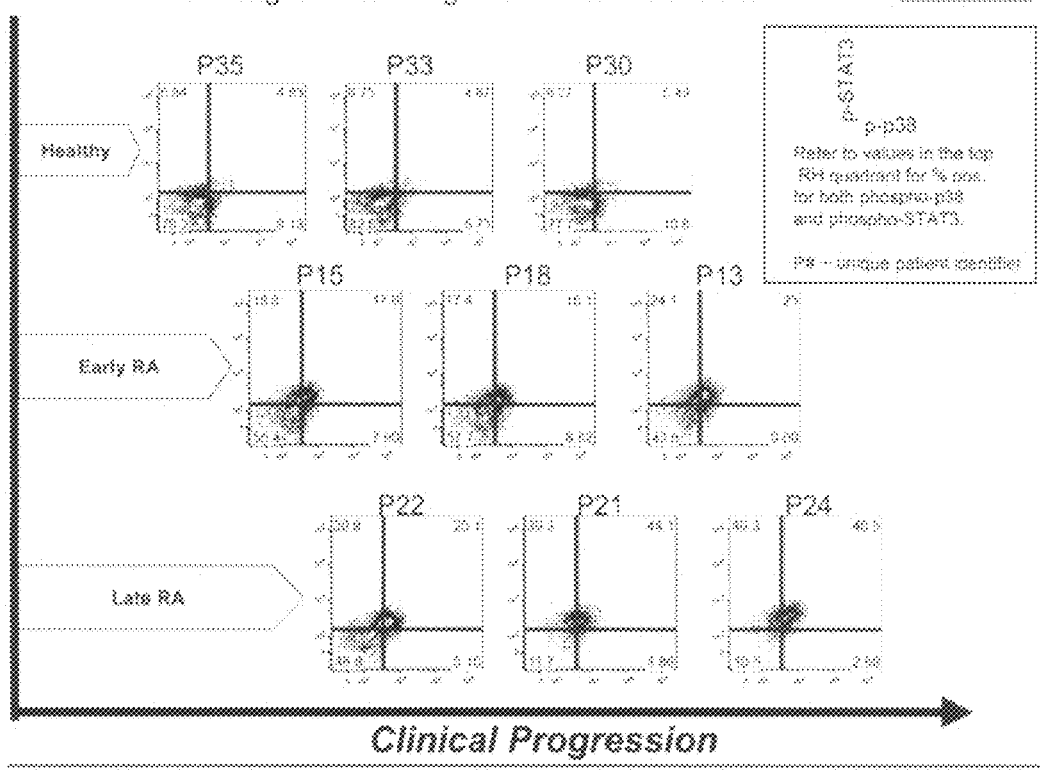

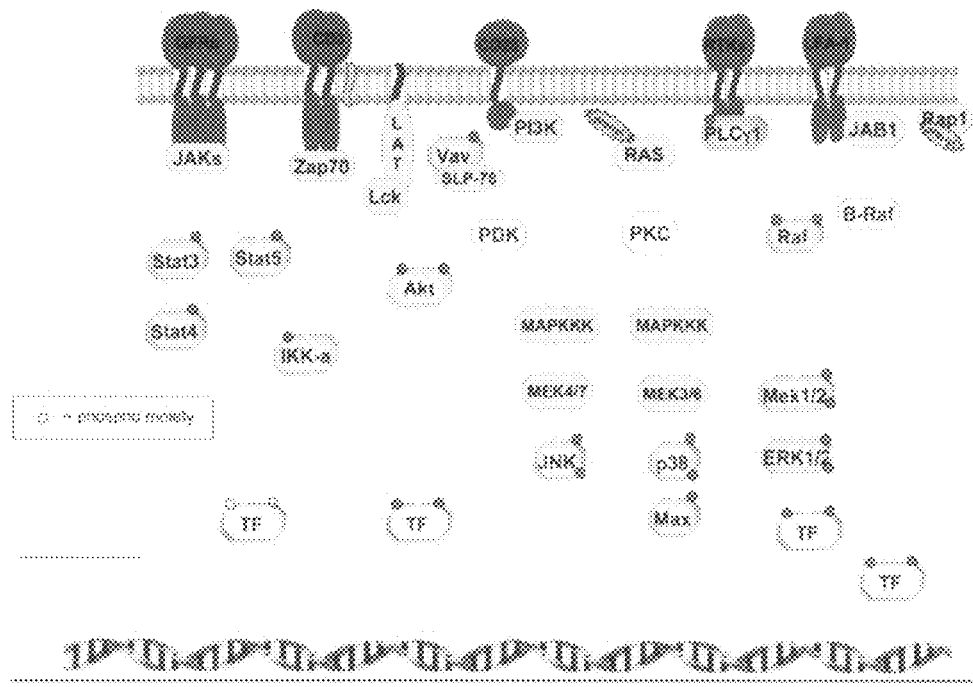

FIGURE 12
A
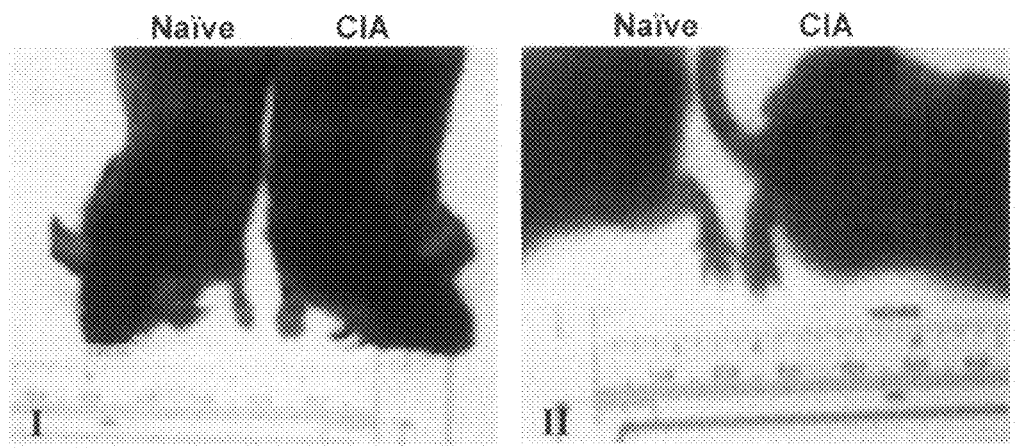
B
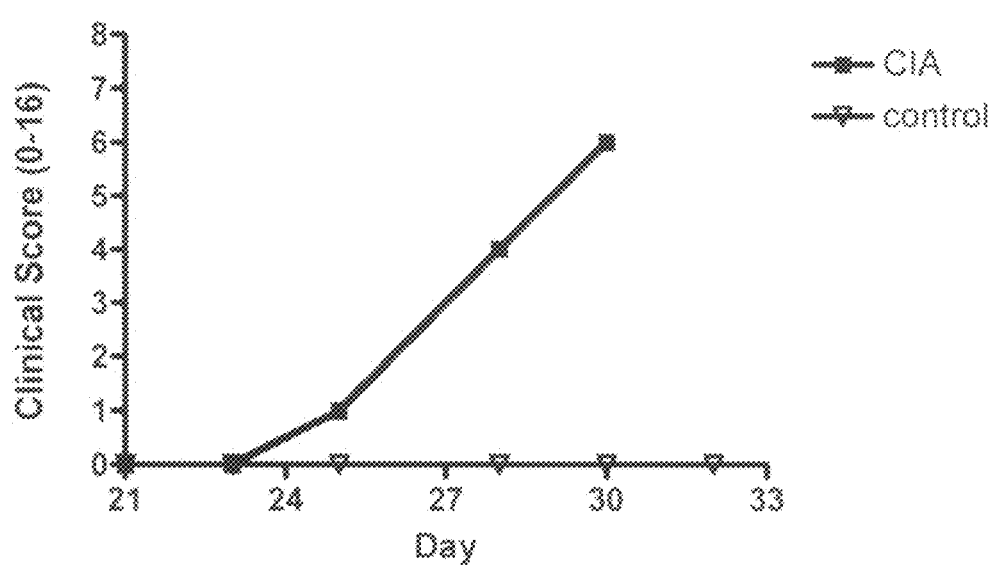

FIGURE 12 (continued)
C
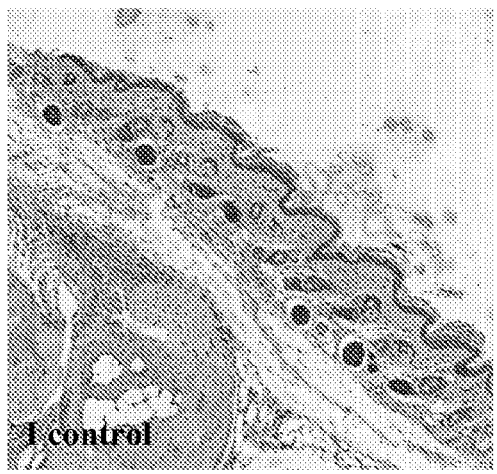
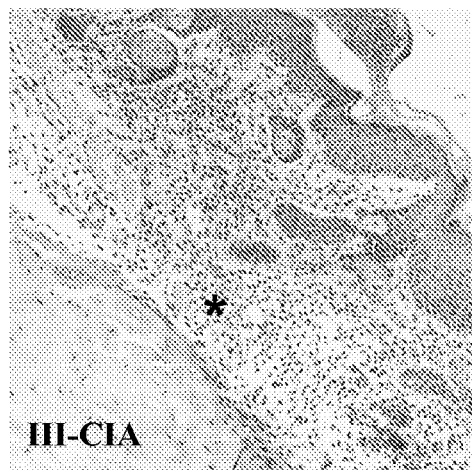
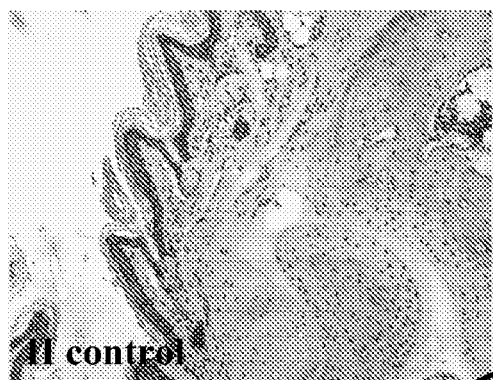
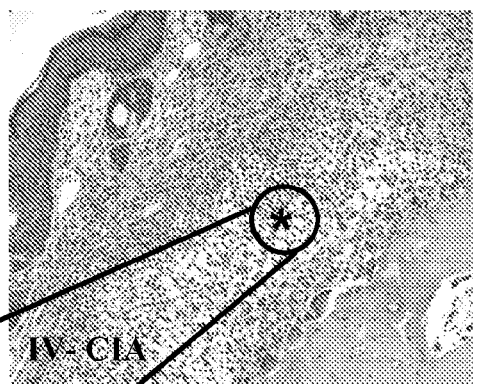
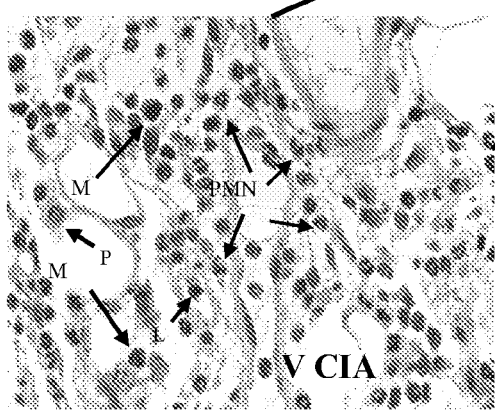
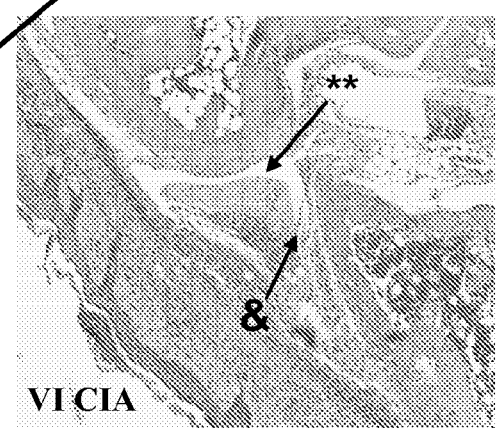

FIGURE 12 (continued)
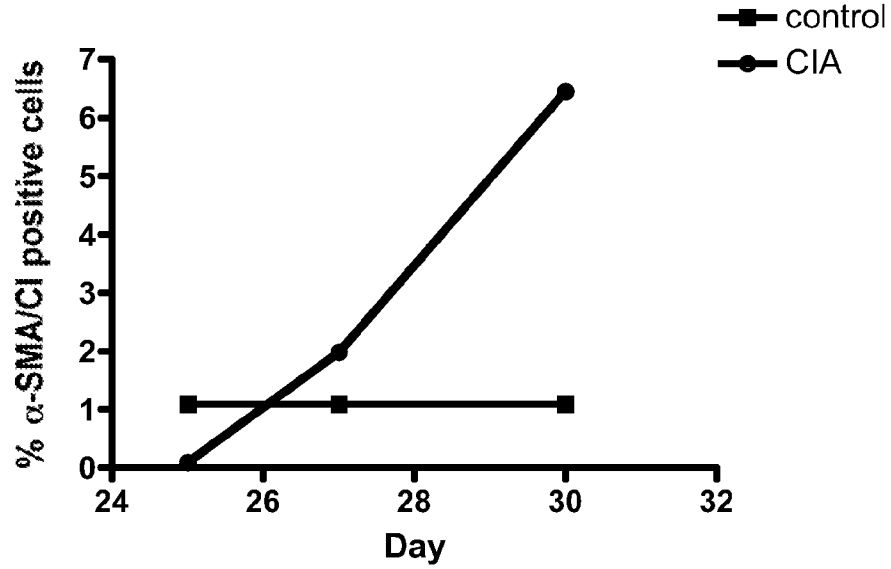
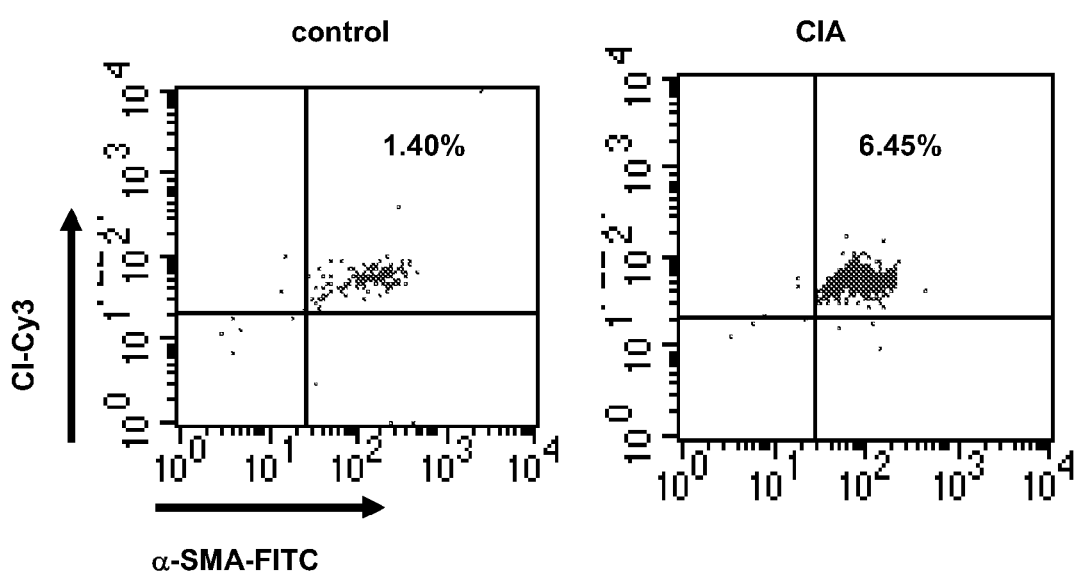

METHODS OF DIAGNOSING AND TREATING RHEUMATOID ARTHRITIS AND OSTEOARTHRITIS

CROSS REFERENCE TO RELATED APPLICATIONS

This application claims priority under 35 USC 119(e) from U.S. provisional application No. 60/808,294, filed on May 25, 2006, which is incorporated by reference herein its entirety.

FEDERALLY-SPONSORED RESEARCH OR DEVELOPMENT

This invention was made with Government support under contract HV028183 awarded by the National Institutes of Health. The Government has certain rights in this invention.

FIELD OF THE INVENTION

The invention relates to a novel cell that is a precursor of a fibroblast-like synovial cell. The invention also relates to methods of diagnosing or monitoring rheumatoid arthritis and/or osteoarthritis using gene expression profiles, protein expression profiles, and/or protein phosphorylation profiles of different cell types, including the novel precursor, CD3+ cells, fibroblast-like synovial cells, and fibrocytes.

BACKGROUND OF THE INVENTION

Rheumatoid arthritis (RA) is a common, relapsing autoimmune disease affecting 0.8-1% of the population worldwide (1) (2). RA presents clinically with joint swelling, deformity, pain, stiffness, and weakness (3). The primary sites of tissue damage are joints, but systemic involvement of the eyes, kidneys, chest and lungs may also occur (4). The rheumatoid synovial environment is an area of intense immunological activity. The cellular composition of the affected RA joint is characterized by proliferation of synovial lining cells, pannus accumulation over articular cartilage and the infiltration of inflammatory cells, including mononuclear cells and lymphocytes. Fibroblast-like synovial (FLS) cells are thought to be responsible for pannus formation and contribute to bone and cartilage destruction.

One of the hallmarks of RA is synovial hyperplasia. Two critical resident cells types in affected synovial tissue (ST) are: a CD68+/MHCII+ macrophage-like synoviocyte (MLS) and a CD68−/MHCII-FLS cell (5). The intimal layer increases from several cells to 15 cells deep, due to increased FLS cell numbers, through a combination of increased proliferation, decreased apoptosis and decreased senescence (5). FLS cells synthesize and secrete many pro-inflammatory mediators—cytokines, chemokines, growth factors—that are involved in autocrine and paracrine regulation of inflammation (5) and, therefore, are critical effectors in regulating the inflammatory response in RA. FLS cells are found in the intima and subintima, and FLS cells in RA are thought to transform into cells that proliferate in an anchorage-independent manner, lack contact inhibition and secrete cytokines constitutively. Many growth factors, such as PDGF, bFGF, TGF-β and activin are expressed in RA and drive fibroblast proliferation in vitro (6) (7) (8) (9) (10).

SUMMARY OF THE INVENTION

The present inventors have identified a precursor of a fibroblast-like synovial cell that comprises a circulating cell that stains positive for collagen, CD34, CD45, prolyl 4-hydroxylase and CD14. The activation status of the novel precursor is useful to diagnose or monitor rheumatoid arthritis in a subject.

Accordingly, the invention includes an isolated precursor of a fibroblast-like synovial cell, comprising a circulating cell that stains positive for collagen, CD34, CD45, prolyl 4-hydroxylase and CD14.

The invention also includes a method of diagnosing or monitoring rheumatoid arthritis in a subject, comprising the steps:
  (a) determining the number of isolated precursor cells of the invention in a sample from the subject; and
  (b) comparing the number of isolated precursor cells from the sample with a control;
wherein a difference in the number of isolated precursor cells in the sample from the subject as compared to the control is indicative of rheumatoid arthritis.

Another aspect of the invention, is a method of diagnosing or monitoring rheumatoid arthritis in a subject, comprising the steps:
  (a) determining the activation state of the isolated precursor cell of the invention from a sample from the subject; and
  (b) (b) comparing the activation state of the isolated precursor cell from the sample with a control;
wherein the activation state of the precursor cell is determined by measuring the phosphorylation levels of signaling molecules, and
wherein a difference in the activation state of the isolated precursor cell as compared to the control is indicative of rheumatoid arthritis.

The invention also includes the use of the isolated precursor cell of the invention to diagnose or monitor rheumatoid arthritis.

An additional aspect of the invention is a method of identifying a substance to treat or prevent rheumatoid arthritis, comprising the steps:
  (a) determining the number of isolated precursor cells of the invention in a sample from a subject treated with a substance; and
  (b) comparing the number of isolated precursor cells from the sample with a control;
wherein a difference in the number of isolated precursor cells in the sample from the subject as compared to the control is indicative of a substance to treat or prevent rheumatoid arthritis.

A further aspect of the invention is a method of identifying a substance to treat or prevent rheumatoid arthritis, comprising the steps:
  (a) determining the activation state of the isolated precursor cell of the invention from a sample from a subject treated with a substance; and
  (b) comparing the activation state of the isolated precursor cell from the sample with a control;
wherein the activation state of the precursor cell is determined by measuring the phosphorylation levels of signaling molecules, and
wherein a difference in the activation state of the isolated precursor cell as compared to the control is indicative of a substance to treat or prevent rheumatoid arthritis.

In addition, the invention includes the use of the isolated precursor cell of the invention to identify a substance to treat or prevent rheumatoid arthritis.

The inventors have also analyzed the activation status of circulating CD3+ cells and have determined that increases in phosphorylation of various signaling molecules correlates with the progression of rheumatoid arthritis.

Accordingly, the invention includes a method of diagnosing or monitoring rheumatoid arthritis in a subject, comprising the steps:
(a) determining the activation state of a CD3+ cell from a sample from the subject; and
(b) comparing the activation state of the CD3+ cell from the sample with a control;
wherein, the activation state of the CD3+ cell is determined by measuring the phosphorylation levels of signaling molecules, and
wherein a difference in the activation state of the CD3+ cell as compared to the control is indicative of rheumatoid arthritis.

The invention also includes the use of a CD3+ cell to diagnose or monitor rheumatoid arthritis in subject.

Another aspect of the invention is a method of identifying a substance to treat or prevent rheumatoid arthritis comprising the steps:
(a) determining the activation state of a CD3+ cell from a sample from a subject treated with a substance; and
(b) comparing the activation state of the CD3+ cell from the sample with a control;
wherein the activation state of the CD3+ cell is determined by measuring the phosphorylation levels of signaling molecules, and
wherein a difference in the activation state of the CD3+ cell as compared to the control is indicative of a substance to treat or prevent rheumatoid arthritis.

The invention also includes the use of a CD3+ cell to identify a substance to treat or prevent rheumatoid arthritis.

The inventors have also characterized the gene and protein expression profiles of synovial tissue fibroblast-like synovial cells, and the protein phosphorylation profiles of these cells in samples from individuals with rheumatoid arthritis or osteoarthritis.

Accordingly, the invention includes a method of diagnosing or monitoring rheumatoid arthritis in a subject, comprising the steps:
(a) determining the gene expression profile of a synovial tissue fibroblast-like synovial cell from a sample from the subject; and
(b) comparing the gene expression profile of the synovial tissue fibroblast-like synovial cell from the sample with a control;
wherein a difference in the gene expression profile of the synovial tissue fibroblast-like synovial cell as compared to the control is indicative of rheumatoid arthritis.

Another aspect of the invention is a method of diagnosing or monitoring osteoarthritis in a subject, comprising the steps:
(a) determining the gene expression profile of a synovial tissue fibroblast-like synovial cell from a sample from the subject; and
(b) comparing the gene expression profile of the synovial tissue fibroblast-like synovial cell from the sample with a control;
wherein a difference in the gene expression profile of the synovial tissue fibroblast-like synovial cell as compared to the control is indicative of osteoarthritis.

An additional aspect of the invention is a method of diagnosing or monitoring rheumatoid arthritis in a subject, comprising the steps:
(a) determining the protein expression profile of a synovial tissue fibroblast-like synovial cell from a sample from the subject; and
(b) comparing the protein expression profile of the synovial tissue fibroblast-like synovial cell from the sample with a control;
wherein a difference in the protein expression profile of the synovial tissue fibroblast-like synovial cell as compared to the control is indicative of rheumatoid arthritis.

A further aspect of the invention is a method of diagnosing or monitoring osteoarthritis in a subject, comprising the steps:
(a) determining the protein expression profile of a synovial tissue fibroblast-like synovial cell from a sample from the subject; and
(b) comparing the protein expression profile of the synovial tissue fibroblast-like synovial cell from the sample with a control;
wherein a difference in the protein expression profile of the synovial tissue fibroblast-like synovial cell as compared to the control is indicative of osteoarthritis.

An additional aspect of the invention is a method of diagnosing or monitoring rheumatoid arthritis in a subject, comprising the steps:
(a) determining the protein phosphorylation profile of a synovial tissue fibroblast-like synovial cell from a sample from the subject; and
(b) comparing the protein phosphorylation profile of the synovial tissue fibroblast-like synovial cell from the sample with a control;
wherein a difference in the protein phosphorylation profile of the synovial tissue fibroblast-like synovial cell as compared to the control is indicative of rheumatoid arthritis.

Another aspect of the invention is a method of diagnosing or monitoring osteoarthritis in a subject, comprising the steps:
(a) determining the protein phosphorylation profile of a synovial tissue fibroblast-like synovial cell from a sample from the subject; and
(b) comparing the protein phosphorylation profile of the synovial tissue fibroblast-like synovial cell from the sample with a control;
wherein a difference in the protein phosphorylation profile of the synovial tissue fibroblast-like synovial cell as compared to the control is indicative of osteoarthritis.

The methods of the invention can also be used to identify substances to treat or prevent rheumatoid arthritis or osteoarthritis.

A further aspect of the invention is a method of diagnosing or monitoring rheumatoid arthritis in a subject, comprising the steps:
(a) determining the number of circulating fibrocytes in a sample from the subject; and
(b) comparing the number of fibrocytes from the sample with a control;
wherein a difference in the number of fibrocytes in the sample from the subject as compared to the control is indicative of rheumatoid arthritis.

Another aspect of the invention, is a method of diagnosing or monitoring rheumatoid arthritis in a subject, comprising the steps:
(a) determining the activation state of a circulating fibrocyte from a sample from the subject; and
(b) comparing the activation state of the fibrocyte from the sample with a control;
wherein the activation state of the fibrocyte is determined by measuring the phosphorylation levels of signaling molecules, and
wherein a difference in the activation state of the fibrocyte as compared to the control is indicative of rheumatoid arthritis.

The invention also includes using circulating fibrocytes to diagnose or monitor rheumatoid arthritis.

An additional aspect of the invention is a method of identifying a substance to treat or prevent rheumatoid arthritis, comprising the steps:
- (a) determining the number of circulating fibrocytes in a sample from a subject treated with a substance; and
- (b) comparing the number of fibrocytes from the sample with a control;

wherein a difference in the number of fibrocytes in the sample from the subject as compared to the control is indicative of a substance to treat or prevent rheumatoid arthritis.

A further aspect of the invention is a method of identifying a substance to treat or prevent rheumatoid arthritis, comprising the steps:
- (a) determining the activation state of circulating fibrocytes from a sample from a subject treated with a substance; and
- (b) comparing the activation state of the fibrocyte from the sample with a control;

wherein the activation state of the fibrocyte is determined by measuring the phosphorylation levels of signaling molecules, and wherein a difference in the activation state of the fibrocyte as compared to the control is indicative of a substance to treat or prevent rheumatoid arthritis.

In addition, the invention includes the use of circulating fibrocytes to identify a substance to treat or prevent rheumatoid arthritis.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will now be described in relation to the drawings in which:

FIG. 4 shows the immunostaining results of peripheral blood fibrocytes for various markers. (A) FACS analysis of a population of peripheral blood fibrotcyes. (B) Confocal microscopy of a single peripheral blood fibrocyte. Images were collected using an upright Leica SP2 confocal laser-scanning microscope (Leica Microsystems Heidelberg GmbH, Mannheim, Germany), 100× oil immersion lens (1.4 NA) and 4× digital zoom.

FIG. 5 shows the results of an intracellular analysis of phospho-STAT3 in CD3−, collagen+ peripheral blood fibrocytes.

FIG. 6 shows the results of an intracellular analysis of phospho-STAT5 in CD3−, collagen+ peripheral blood fibrocytes.

FIG. 7 shows the results of an intracellular analysis of phospho-ERK in CD3−, collagen+ peripheral blood fibrocytes.

FIG. 8 shows the results of an intracellular analysis of phospho-p38 MAPK in CD3−, collagen+ peripheral blood fibrocytes.

FIG. 9 shows protein phosphorylation profiles of sub-populations and primary cells.

FIG. 10 shows the results of an intracellular analysis of phospho-STAT3 and phospho-p38 in CD3+ cells from healthy individuals, early rheumatoid arthritis patients and late rheumatoid arthritis patients.

FIG. 11 depicts a signalizing cascade.

FIG. 12 shows circulating fibrocytes in CIA. Mice with CIA exhibit obvious swelling of the paws/joints compared to naïve animals (A-1, II). Affected joints were scored on a scale of 0-16 and the cumulative disease score is shown in panel B. Mice with CIA cumulative score of 6/individual paw score of 2, show obvious swelling and cellular infiltrates in the dermis (C III, magnification 100×; C IV, magnification 200×*) compared to control animals (C I, magnification 100×; C II, magnification 200×). The majority of the inflammatory infiltrate were neutrophils (PMN) but macrophages (M), lymphocytes (L) and plasma cells (P) were also observed (C V, 1000× magnification). Swelling (**) and early inflammatory infiltrates (&) were observed in the intra-articular spaces (C VI, 200× magnification). PBMC were collected by cardiac puncture at different stages of disease and FACS analysis performed to detect the α-SMA/CI fibrocyte population (D). Panel E describes the α-SMA/CI fibrocyte population on day 30. Large granular cells were gated by FSC/SSC and double positive cells are shown. Notably, the number of circulating fibrocytes was higher in mice with higher disease scores.

DETAILED DESCRIPTION OF THE INVENTION

Figure 1:
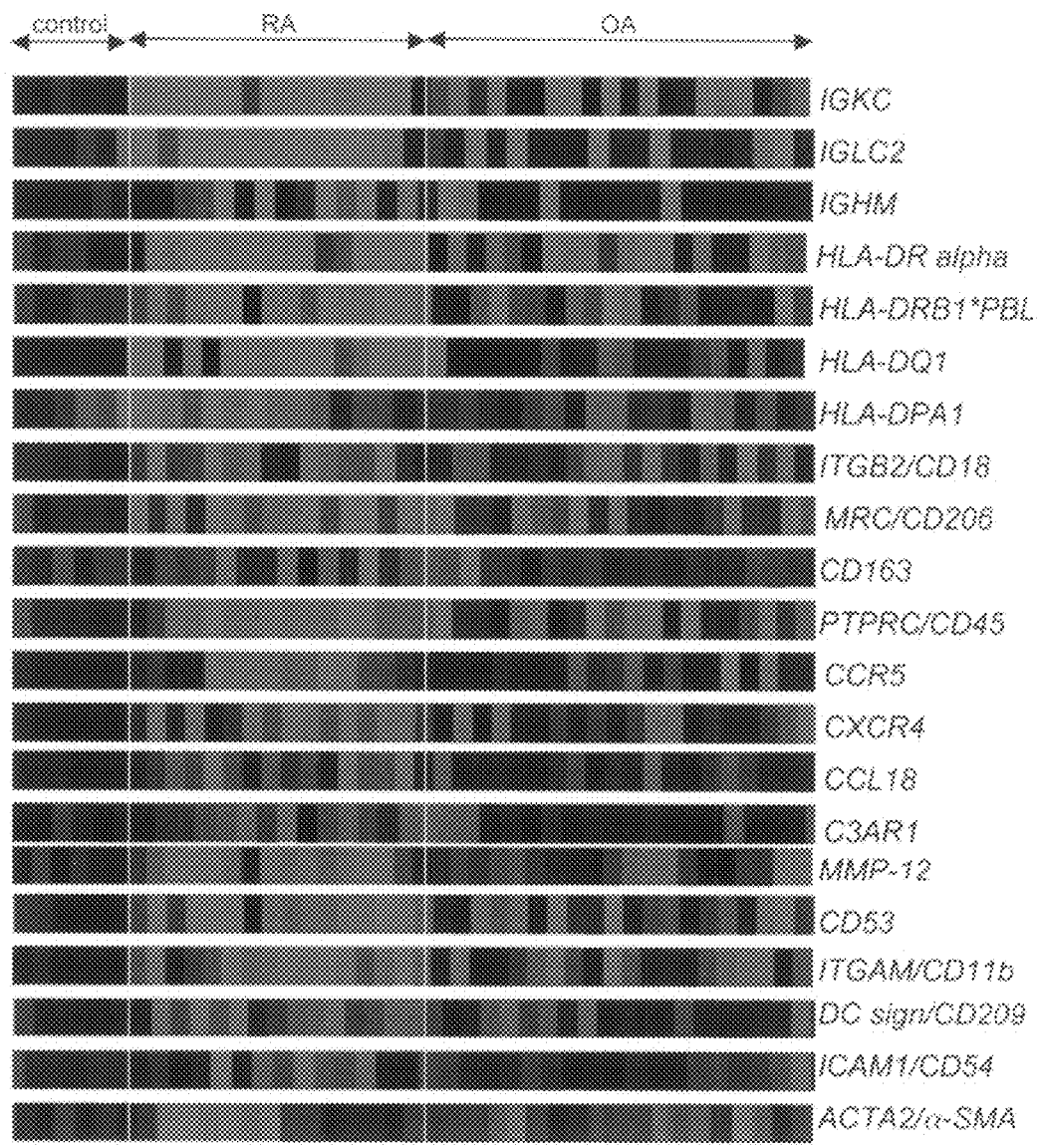
FIG. 1 is heat map representation showing the gene expression levels of synovial tissue fibroblast-like synovial cells in controls or subjects with rheumatoid arthritis or osteoarthritis. Red indicates increased expression levels above the mean and increasing blue intensity indicates reduced expression. The intensity of the red or blue corresponds to the extent of the change from normal.

The inventors have discovered a precursor of a fibroblast-like synovial cell. This cell is a circulating cell and can migrate to affected joints in subjects with rheumatoid arthritis, and is able to transform into resident myofibroblasts and fibroblast-like synovial cells. The precursor cell stains positive for collagen, CD34, CD45, prolyl 4-hydroxylase and CD14, and can be isolated from the circulatory system, for example from peripheral blood mononuclear cells from healthy individuals and individuals with rheumatoid arthritis.

Accordingly, the invention provides an isolated precursor of a fibroblast-like synovial cell, comprising a circulating cell that stains positive for collagen, CD34, CD45, prolyl 4-hydroxylase and CD14.

The term "isolated precursor of a fibroblast-like synovial cell" as used herein refers to the precursor cells of the invention substantially free of other cell types. In another embodiment, the cells are also substantially free of cellular debris or other cellular material, or culture medium.

The invention includes a method of diagnosing or monitoring rheumatoid arthritis in a subject, comprising the steps:
  (a) determining the number of isolated precursor cells of the invention in a sample from the subject; and
  (b) comparing the number of isolated precursor cells from the sample with a control;
  wherein a difference in the number of isolated precursor cells in the sample from the subject as compared to the control is indicative of rheumatoid arthritis.

The inventors also analyzed the activation state of this circulating precursor cell in healthy individuals and subjects with early rheumatoid arthritis and subjects with later stages of disease. The activation state of the precursor cell was determined by analyzing the phosphorylation levels of signaling molecules, including STAT3, STAT5, ERK and/or p38 MAPK.

Accordingly, the invention includes a method of diagnosing or monitoring rheumatoid arthritis in a subject, comprising the steps:
  (a) determining the activation state of the isolated precursor cell of the invention from a sample from the subject; and
  (b) comparing the activation state of the isolated precursor cell from the sample with a control;
  wherein the activation state of the precursor cell is determined by measuring the phosphorylation levels of signaling molecules, and
  wherein a difference in the activation state of the isolated precursor cell as compared to the control is indicative of rheumatoid arthritis.

The phrase "diagnosing or monitoring rheumatoid arthritis" as used herein refers to a method or process of determining if a subject has or does not have rheumatoid arthritis, or determining the severity or degree of rheumatoid arthritis.

The term "subject" as used herein refers to any member of the animal kingdom, preferably a human being.

The term "sample" as used here refers to any fluid, cell or tissue sample from an individual which includes the precursor cell of the invention. In one embodiment, the sample is from the circulatory system of the individual.

The term "control" as used herein refers to a sample from a subject or a group of subjects who are either known as having rheumatoid arthritis or not having rheumatoid arthritis, or who are known as having a particular severity or degree of rheumatoid arthritis or not. A subject known not to have rheumatoid arthritis is also referred to as a "healthy individual" herein. For example, the control can be from a healthy individual, a subject with early stage rheumatoid arthritis or a subject with late stage rheumatoid arthritis. A person skilled in the art will appreciate that a subject with early stage rheumatoid arthritis can be defined to include individuals within the first year of onset of symptoms with 3 swollen joints.

The phrase "difference in number of isolated precursor cells in the sample from the subject as compared to the control is indicative of rheumatoid arthritis" refers to the difference in frequency of cells. There are generally greater numbers of the isolated precursor cells in samples from subjects with rheumatoid arthritis as compared to healthy individuals. In addition, there are greater numbers of the isolated precursor cells in samples from subjects as the disease progresses. For example, there are greater numbers of the isolated precursor cell from subjects with late stage rheumatoid arthritis as compared to subjects with early stage rheumatoid arthritis. Thus, if the control is a healthy individual, then there are greater numbers of the isolated precursor cells in the samples from subjects with rheumatoid arthritis as compared to the control. If the control is a subject with early stage rheumatoid arthritis, then there are greater numbers of the precursor cells in samples with late stage rheumatoid arthritis as compared to the control.

The "activation state of the isolated precursor cell" can be determined by measuring the activation status of signaling molecules within the isolated precursor cell. For example, the activation status of signaling molecules can be determined by measuring the phosphorylation levels of signaling molecules, such as STAT3, STAT5, ERK and/or p38 MAPK.

The phrase "difference in the activation state of the isolated precursor cell as compared to the control is indicative of rheumatoid arthritis" refers to a difference in the frequency or levels of phosphorylation of signaling molecules in the isolated precursor cell, including STAT3, STAT5, ERK and p38 MAPK, as compared to the control. There are more frequent and/or higher levels of phosphorylation of signaling molecules in samples from subjects with rheumatoid arthritis as compared to healthy individuals. There are generally more frequent and/or higher levels of phosphorylation of signaling molecules in samples from subjects as the disease progresses. For example, there are more frequent and/or higher levels of phosphorylation of signaling molecules in samples from subjects with late stage rheumatoid arthritis as compared to subjects with early stage rheumatoid arthritis. Thus, if the control is a healthy individual, then there are more frequent and/or higher levels of phosphorylation of signaling molecules in precursor cells in samples from subjects with rheumatoid arthritis as compared to the control. If the control is a subject with early stage rheumatoid arthritis, then there are more frequent and/or higher levels of phosphorylation of signaling molecules in precursor cells in samples from subjects with late stage rheumatoid arthritis as compared to the control.

The invention also includes the use of the isolated precursor cell of the invention to diagnose or monitor rheumatoid arthritis.

The isolated precursor cell of the invention can also be used in methods of drug discovery or methods to identify substances that can treat or prevent rheumatoid arthritis. For example, an additional aspect of the invention is a method of identifying a substance to treat or prevent rheumatoid arthritis, comprising the steps:
  (a) determining the number of isolated precursor cells of the invention in a sample from a subject treated with a substance; and
  (b) comparing the number of isolated precursor cells from the sample with a control;
wherein a difference in the number of isolated precursor cells in the sample from the subject as compared to the control is indicative of a substance to treat or prevent rheumatoid arthritis.

In another example, the invention includes a method of identifying a substance to treat or prevent rheumatoid arthritis, comprising the steps:
  (a) determining the activation state of the isolated precursor cell of the invention from a sample from a subject treated with a substance; and
  (b) comparing the activation state of the isolated precursor cell from the sample with a control;
wherein the activation state of the precursor cell is determined by measuring the phosphorylation levels of signaling molecules, and
wherein a difference in the activation state of the isolated precursor cell as compared to the control is indicative of a substance to treat or prevent rheumatoid arthritis.

The phrase "treat or prevent rheumatoid arthritis" as used herein refers to a medical aid to counteract the disease itself, the symptoms and/or the progression of the disease.

"Measuring the phosphorylation levels of signaling molecules" as used herein refers to measuring the frequency and/or intensity of phosphorylation of signaling molecules, such as STAT3, STAT5, ERK and/or p38 MAPK.

A person skilled in the art will appreciate that the control can be a sample from a subject not treated with a substance or treated with a substance that is known not to treat or prevent rheumatoid arthritis. In one embodiment, reduced numbers of the isolated precursor cell in the sample as compared to the control is indicative of a substance for the treatment or prevention of rheumatoid arthritis. In another embodiment, a reduced activation state of the isolated precursor cell in the sample as compared to the control is indicative of a substance for the treatment or prevention of rheumatoid arthritis. In addition, the control can be a sample from the same subject, but before treatment with the substance to be tested or samples from the subject taken at different points of time during treatment with the substance to be tested.

Substances for the treatment or prevention of rheumatoid arthritis can also be identified using cells or cell lines. For example, individual precursor cells or cell lines derived from the precursor cell of the invention can be contacted with a substance and then the activation state of the cells can be compared to a control.

The inventors have also studied the activation status of circulating CD3+ cells from rheumatoid arthritis patients at different stages of disease. They discovered that there are progressive increases in the phosphorylation of signaling molecules, such as STAT3 and p38 MAPK, in CD3+ cells, which correlate with disease progression.

Accordingly, the invention includes method of diagnosing or monitoring rheumatoid arthritis in a subject, comprising the steps:
  (a) determining the activation state of a CD3+ cell from a sample from the subject; and
  (a) comparing the activation state of the CD3+ cell from the sample with a control;
wherein, the activation state of the CD3+ cell is determined by measuring the phosphorylation levels of signaling molecules, such as STAT3 and/or p38 MAPK, and
wherein a difference in the activation state of the CD3+ cell as compared to the control is indicative of rheumatoid arthritis.

The "activation state of the CD3+ cell" can be determined by measuring the activation status of signaling molecules within CD3+ cell. For example, the activation status of signaling molecules can be determined by measuring the phosphorylation levels of signaling molecules, such as STAT3 and/or p38 MAPK.

The phrase "difference in the activation state of the CD3+ cell as compared to the control" refers to a difference in the frequency or levels of phosphorylation of signaling molecules in the CD3+ cell, including STAT3 and/or p38 MAPK, as compared to the control.

The term "sample" as used here refers to any fluid, cell or tissue sample from an individual which includes a CD3+ cell.

The invention also includes the use of a CD3+ cell to diagnose or monitor rheumatoid arthritis in a subject.

The findings of the inventors can also be used in methods of drug discovery. Accordingly, the invention includes method of identifying a substance to treat or prevent rheumatoid arthritis comprising the steps:
  (a) determining the activation state of a CD3+ cell from a sample from a subject treated with a substance; and
  (b) comparing the activation state of the CD3+ cell from the sample with a control;
wherein the activation state of the CD3+ cell is determined by measuring the phosphorylation levels of signaling molecules, and
wherein a difference in the activation state of the CD3+ cell as compared to the control is indicative of a substance to treat or prevent rheumatoid arthritis.

The invention also includes the use of a CD3+ cell to identify a substance to treat or prevent rheumatoid arthritis.

The inventors have also analyzed and characterized the gene expression and protein expression profiles of synovial tissue fibroblast-like synovial cells from subjects with rheumatoid arthritis and osteoarthritis. The inventors have discovered that there are different gene expression and protein expression profiles, and protein phosphorylation profiles in synovial tissue fibroblast-like synovial cells from subjects with rheumatoid arthritis, osteoarthritis and healthy individuals.

The inventors discovered a number of rheumatoid arthritis specific genes that can be used to characterize the gene expression profile in the method of the invention. These genes include transport, apoptosis regulatory, cell adhesion, cell surface signaling receptors, intracellular signaling, secreted stimulatory and immunomodulatory genes. In addition, the inventors discovered a significant differential expression of 154 genes in fibroblast-like synovial cells in subjects with osteoarthritis or rheumatoid arthritis. See Tables 1 and 2.

Accordingly, the invention includes a method of diagnosing or monitoring rheumatoid arthritis in a subject, comprising the steps:

(a) determining the gene expression profile of a synovial tissue fibroblast-like synovial cell from a sample from the subject; and (b) comparing the gene expression profile of the synovial tissue fibroblast-like synovial cell from the sample with a control;

wherein a difference in the gene expression profile of the synovial tissue fibroblast-like synovial cell as compared to the control is indicative of rheumatoid arthritis.

In one embodiment, the gene expression profile that characterizes subjects with rheumatoid arthritis includes enhanced gene expression of one or more of the genes listed in Table 1.

In another embodiment, the gene expression profile that characterizes subjects with rheumatoid arthritis includes enhanced gene expression of genes encoding immunoglobulin constant regions, CD53, CD11b, CD18, CD86, CD206, CD163, mannose receptor, DC-SIGN, C3AR1, Fc-receptors, complement receptors, and/or MHC class II molecules as compared to the control.

The invention also includes a method of diagnosing or monitoring osteoarthritis in a subject, comprising the steps:

(a) determining the gene expression profile of a synovial tissue fibroblast-like synovial cell from a sample from the subject; and (b) comparing the gene expression profile of the synovial tissue fibroblast-like synovial cell from the sample with a control;

wherein a difference in the gene expression profile of the synovial tissue fibroblast-like synovial cell as compared to the control is indicative of osteoarthritis.

The term "control" as used here refers to a sample from a subject or group of subjects who are either known as having osteoarthritis or not, or who are known as having a particular severity or degree of osteoarthritis or not.

In one embodiment, the gene expression profile that characterizes subjects with osteoarthritis includes enhanced gene expression of one or more of the genes listed in Table 2.

The term "sample" as used here refers to any fluid, cell or tissue sample from an individual which includes a synovial tissue fibroblast-like synovial cell.

The term "gene expression profile" as used herein refers to the level of RNA expressed from one or more gene in the synovial tissue fibroblast-like synovial cell from a sample from the subject.

The term "difference in gene expression profile" as used here refers to an increase or decrease in the measurable expression of RNA of a particular gene or group of genes as compared to the measurable expression of RNA of the same gene or group of genes in a second sample. The comparison can be made between individual samples or populations of samples. In one embodiment, the differential expression can be compared using the ratio of the level of expression of the gene as compared with the expression level of the gene of a control, wherein the ratio is not equal to 1.0. For example, an RNA is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, a gene is identified as being differentially expressed as between a first and second population when the p-value is less than 0.1, preferably less than 0.05, more preferably less than 0.01, even more preferably less than 0.005, the most preferably less than 0.001.

In addition to measuring the gene expression profile, a person skilled in the art will appreciate that the protein expression profile of a synovial tissue fibroblast-like synovial cell can be measured.

The term "protein expression profile" as used herein refers to the level of one or more proteins expressed in the synovial tissue fibroblast-like synovial cell from a sample from the subject. The protein expression profile can include measurements of the expression of transport, apoptosis regulatory, cell adhesion, cell surface signaling receptors, intracellular signaling, secreted stimulatory and immunomodulatory proteins. This includes measuring the protein expression of immunoglobulin constant regions, CD53, CD11b, CD18, CD86, CD206, CD163, mannose receptor, DC-SIGN, C3AR1, Fc-receptors, complement receptors, and/or MHC class II molecules.

Accordingly, the invention includes a method of diagnosing or monitoring rheumatoid arthritis in a subject, comprising the steps:

(a) determining the protein expression profile of a synovial tissue fibroblast-like synovial cell from a sample from the subject; and (b) comparing the protein expression profile of the synovial tissue fibroblast-like synovial cell from the sample with a control;

wherein a difference in the protein expression profile of the synovial tissue fibroblast-like synovial cell as compared to the control is indicative of rheumatoid arthritis.

In one embodiment, the protein expression profile that characterizes subjects with rheumatoid arthritis includes enhanced protein expression of one or more proteins encoded by the genes listed in Table 1.

The invention also includes a method of diagnosing or monitoring osteoarthritis in a subject, comprising the steps:

(a) determining the protein expression profile of a synovial tissue fibroblast-like synovial cell from a sample from the subject; and (b) comparing the protein expression profile of the synovial tissue fibroblast-like synovial cell from the sample with a control;

wherein a difference in the protein expression profile of the synovial tissue fibroblast-like synovial cell as compared to the control is indicative of osteoarthritis.

In one embodiment, the protein expression profile that characterizes subjects with osteoarthritis includes enhanced protein expression of one or more of the proteins encoded by the genes listed in Table 2.

The term "difference in protein expression profile" as used here refers to an increase or decrease in the measurable expression of a particular protein or group of proteins as compared to the measurable expression of the same protein or group of proteins in a second sample. The comparison can be made between individual samples or populations of samples. In one embodiment, the differential expression can be compared using the ratio of the level of expression of the protein as compared with the expression level of the protein of a control, wherein the ratio is not equal to 1.0. For example, a protein is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, a protein is identified as being differentially expressed as between a first and second population when the p-value is less than 0.1, preferably less than 0.05, more preferably less than 0.01, even more preferably less than 0.005, the most preferably less than 0.001.

In addition to gene and protein expression profiles, the inventors also examined protein phosphorylation profiles in synovial tissue fibroblast-like synovial cells.

Accordingly, the invention includes a method of diagnosing or monitoring rheumatoid arthritis in a subject, comprising the steps:
(a) determining the protein phosphorylation profile of a synovial tissue fibroblast-like synovial cell from a sample from the subject; and
(a) comparing the protein phosphorylation profile of the synovial tissue fibroblast-like synovial cell from the sample with a control;
wherein a difference in the protein phosphorylation profile of the synovial tissue fibroblast-like synovial cell as compared to the control is indicative of rheumatoid arthritis.

The term "protein phosphorylation profile" as used herein refers to the level or frequency of phosphorylation of one or more proteins expressed in synovial tissue fibroblast-like synovial cells from a sample from a subject.

In one embodiment, the difference in the protein phosphorylation profile includes a difference in phosphorylation of AKT, FAK, p38, JNK, cdc-2 and/or PLC-g1 in the synovial tissue fibroblast-like synovial cells in the subject as compared to the control.

The invention also includes a method of diagnosing or monitoring osteoarthritis in a subject, comprising the steps:
(a) determining the protein phosphorylation profile of a synovial tissue fibroblast-like synovial cell from a sample from the subject; and
(b) comparing the protein phosphorylation profile of the synovial tissue fibroblast-like synovial cell from the sample with a control;
wherein a difference in the protein phosphorylation profile of the synovial tissue fibroblast-like synovial cell as compared to the control is indicative of osteoarthritis.

The methods of the invention can also be used to identify substances to treat or prevent rheumatoid arthritis or osteoarthritis.

The inventors also determined that the number of circulating fibrocytes and the activation status of fibrocytes can be used to diagnose or monitor rheumatoid arthritis in a subject.

The term "sample" as used here refers to any fluid, cell or tissue sample from an individual which includes circulating fibrocytes. In one embodiment, the sample is from the circulatory system of the individual.

Accordingly, a further aspect of the invention is a method of diagnosing or monitoring rheumatoid arthritis in a subject, comprising the steps:
(a) determining the number of circulating fibrocytes in a sample from the subject; and
(b) comparing the number of fibrocytes from the sample with a control;
wherein a difference in the number of fibrocytes in the sample from the subject as compared to the control is indicative of rheumatoid arthritis.

The phrase "difference in number of fibrocytes in the sample from the subject as compared to the control is indicative of rheumatoid arthritis" refers to the difference in frequency of cells. There are generally greater numbers of the circulating fibrocytes in samples from subjects with rheumatoid arthritis as compared to healthy individuals. In addition, there are greater numbers of circulating fibrocytes in samples from subjects as the disease progresses. For example, there are greater numbers of circulating fibrocytes from subjects with late stage rheumatoid arthritis as compared to subjects with early stage rheumatoid arthritis. Thus, if the control is a healthy individual, then there are greater numbers of circulating in the samples from subjects with rheumatoid arthritis as compared to the control. If the control is a subject with early stage rheumatoid arthritis, then there are greater numbers of circulating fibrocytes in samples with late stage rheumatoid arthritis as compared to the control.

Another aspect of the invention, is a method of diagnosing or monitoring rheumatoid arthritis in a subject, comprising the steps:
(a) determining the activation state of a circulating fibrocyte from a sample from the subject; and
(b) comparing the activation state of the fibrocyte from the sample with a control;
wherein the activation state of the fibrocyte is determined by measuring the phosphorylation levels of signaling molecules, and
wherein a difference in the activation state of the fibrocyte as compared to the control is indicative of rheumatoid arthritis.

The "activation state of the fibrocyte" can be determined by measuring the activation status of signaling molecules within the isolated precursor cell. For example, the activation status of signaling molecules can be determined by measuring the phosphorylation levels of signaling molecules, such as STAT5.

The phrase "difference in the activation state of the fibrocyte as compared to the control is indicative of rheumatoid arthritis" refers to a difference in the frequency or levels of phosphorylation of signaling molecules in the isolated precursor cell, such as STAT5, as compared to the control. There are more frequent and/or higher levels of phosphorylation of signaling molecules in samples from subjects with rheumatoid arthritis as compared to healthy individuals. There are generally more frequent and/or higher levels of phosphorylation of signaling molecules in samples from subjects as the disease progresses. For example, there are more frequent and/or higher levels of phosphorylation of signaling molecules in samples from subjects with late stage rheumatoid arthritis as compared to subjects with early stage rheumatoid arthritis. Thus, if the control is a healthy individual, then there are more frequent and/or higher levels of phosphorylation of signaling molecules in precursor cells in samples from subjects with rheumatoid arthritis as compared to the control. If the control is a subject with early stage rheumatoid arthritis, then there are more frequent and/or higher levels of phosphorylation of signaling molecules in precursor cells in samples from subjects with late stage rheumatoid arthritis as compared to the control.

The invention also includes using circulating fibrocytes to diagnose or monitor rheumatoid arthritis.

An additional aspect of the invention is a method of identifying a substance to treat or prevent rheumatoid arthritis, comprising the steps:
(a) determining the number of circulating fibrocytes in a sample from a subject treated with a substance; and
(b) comparing the number of fibrocytes from the sample with a control;
wherein a difference in the number of fibrocytes in the sample from the subject as compared to the control is indicative of a substance to treat or prevent rheumatoid arthritis.

A further aspect of the invention is a method of identifying a substance to treat or prevent rheumatoid arthritis, comprising the steps:

(a) determining the activation state of circulating fibrocytes from a sample from a subject treated with a substance; and (b) comparing the activation state of the fibrocyte from the sample with a control;

wherein the activation state of the fibrocyte is determined by measuring the phosphorylation levels of signaling molecules, and wherein a difference in the activation state of the fibrocyte as compared to the control is indicative of a substance to treat or prevent rheumatoid arthritis.

In addition, the invention includes the use of circulating fibrocytes to identify a substance to treat or prevent rheumatoid arthritis.

The following non-limiting examples are illustrative of the present invention:

EXAMPLES

Example 1

Characterization of Gene and Protein Expression Profiles in RA ST FLS Cells

The activated phenotype of distinct cell populations in affected RA patients determines disease severity. Suppression of the activated phenotype of cells in early RA synovitis will subdue the disease process. A clear understanding of those factors that contribute to the activated phenotype is required. The objective of the inventors' studies was to determine the signature gene and protein expression profiles in target cell populations in patients diagnosed with RA. The inventors' hypothesized that a signature pattern of activated factors in distinct cell types would identify potential therapeutic targets. Over the past few years, the inventors have initiated a collection of blood, synovial fluid and ST from RA patients, osteoarthritis (OA) patients and trauma patients at the time of joint surgery. Sample collection involves confirmation of the diagnosis of RA/OA using clinical, serologic and radiologic data and informed consent on all study participants. Clinical parameters are recorded at the time of sample collection. Synovial samples are collected by joint aspiration, fine needle biopsy and via arthroscopic or other surgeries. FLS cells from ST from affected RA joints, OA joints and tissue from trauma patients (non-RA, non-OA, surgery) were collected using a negative-selection protocol for cell fractionation, and cultured in DMEM media. Initial studies examined gene expression profiles of RNA from freshly harvested ST, cells that were passaged up to 3× and cells maintained beyond three passages. Affymetrix microarray analysis (U133 Plus 2.0 microarray representing over 30,000 genes) was performed. RA FLS cells at 3× passage exhibit similar gene expression profiles compared to freshly harvested FLS cells, yet the inventors observed that this characteristic gene expression profile changed with extended time in culture. All subsequent gene expression analyses were conducted on RNA extracted from ST FLS cells cultured for <3 passages. Gene expression data were initially analyzed using GeneSpring 6.1 software (Silicon Genetics). Results of gene tree data analysis of ST FLS cells have revealed distinct and reproducible expression profiles, reflective of the different patient populations (trauma patients, OA, RA), that is significant as determined by one-way ANOVA. Gene tree data analysis sorted the RA-specific genes into functional groupings: transport, apoptosis regulatory, cell adhesion, cell surface signaling receptors, intracellular signaling, secreted stimulatory, and immunomodulatory genes. A gene tree based comparison of OA versus RA ST FLS cell expression profiles revealed significant differential expression of 154 genes (one-way ANOVA, p<0.01), including 17 apoptosis regulatory, 17 cell adhesion, 39 cell surface receptors, 25 immunomodulatory and 28 signal transduction genes. To further analyze these data, the Binary Tree-Structured Vector Quantization (BTSVQ) program was used (11). BTSVQ is a computational tool that combines partitive k-means clustering and Self-Organizing Maps (SOM) to analyze and visualize microarray gene expression data with minimal noise and without preconceived bias. These analyses confirmed distinct signature patterns of gene expression for FLS cells derived from RA (n=16) and OA (n=20) specimens and further distinguished healthy control (trauma patients, n=6) gene expression patterns from RA and OA expression profiles (FIG. 1). Differentially regulated genes in RA FLS cells included cytokines, chemokines and receptors. In agreement with previous studies (12), the inventors also show a transformed phenotype in RA FLS cells, with expression of many genes that are typically not found in fibroblasts. High levels of gene expression for immunoglobulin constant regions: IGKC, IGLC2 and IGHM were seen, typically expressed in B cells. Also, gene expression for many receptors found on antigen presenting cells such as: CD53, CD11b, CD18, CD86, scavenger receptors (CD206, CD163 and the mannose receptor, MRC), DC-SIGN and complement receptor (C3AR1), were observed. The MRC processes molecules for presentation of MHCII and binds to both endogenous and exogenous ligands. Increases in gene expression for Fc- and complement receptor gene expression were observed in RA FLS cells and suggest that these cells trap antigens in the form of immune complexes on their cell surface for presentation. Gene expression for HLA-DR, DQ and DP were also upregulated in RA vs. OA or control FLS cells in the array analyses. HLA molecules are expressed on CD68+ synoviocytes following treatment with IFN-γ (13). Notably, gene expression for CD68 was not evident in the isolated FLS cells. Upregulation of HLA molecules would be consistent with the role of synovial fibroblasts in antigen presentation during an autoimmune disease. The likelihood of contaminating leukocytes, e.g. macrophage-like synoviocytes (MLS), in the fibroblast preparations was eliminated since only adherent prolyl-4 hydroxylase (5B5 antibody) positive cells were processed for gene expression analysis, and there was no significant CD2, CD3 or CD5 gene expression observed in the analysis. This suggests that RA FLS cells either upregulate the B cell/macrophage/dendritic cell markers, de-differentiate into this phenotype, or that immature fibroblast-like cells are recruited and differentiate into these cells in affected joints.

Figure 2:
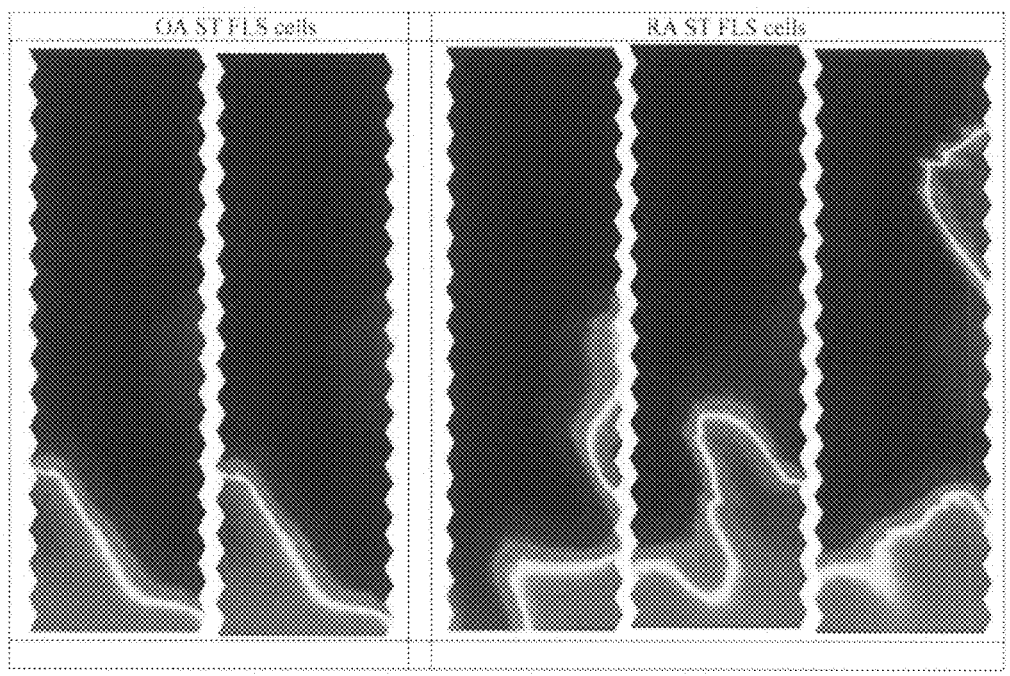
FIG. 2 is a heat map representation showing the phospho-protein signature profiles of synovial tissue fibroblast-like synovial cells (ST FLS) from subjects with rheumatoid arthritis or osteoarthritis. Cell lysates derived from ST FLS cells from affected joints from 2 OA patients (LHS panel) and 3 RA patients (RHS panel) were analyzed using customized BD phospho-protein PowerBlots. Heat map representation: phospho-protein expression profiles are represented as a "heat-map" in which red indicates increased expression levels above the mean and increasing blue intensity indicates reduced expression. The intensity of the red or blue corresponds to the extent of the change from normal. Each array map represents 80 phosphospecificities. Similar patterns are indicative of similar phospho-protein profiles. This is evident for the 2 representative OA ST FLS cell specimens. These are distinguishable from the 3 RA ST FLS cell signature profiles. Interestingly, in regard to the RA specimens, although exhibiting similar phosphorylation-activation of many signaling effectors and kinases, there are clusters of distinctive patterns, allowing for stratification of the RA specimens into 3 subgroups, exemplified by the 3 profiles provided.
Figure 3:
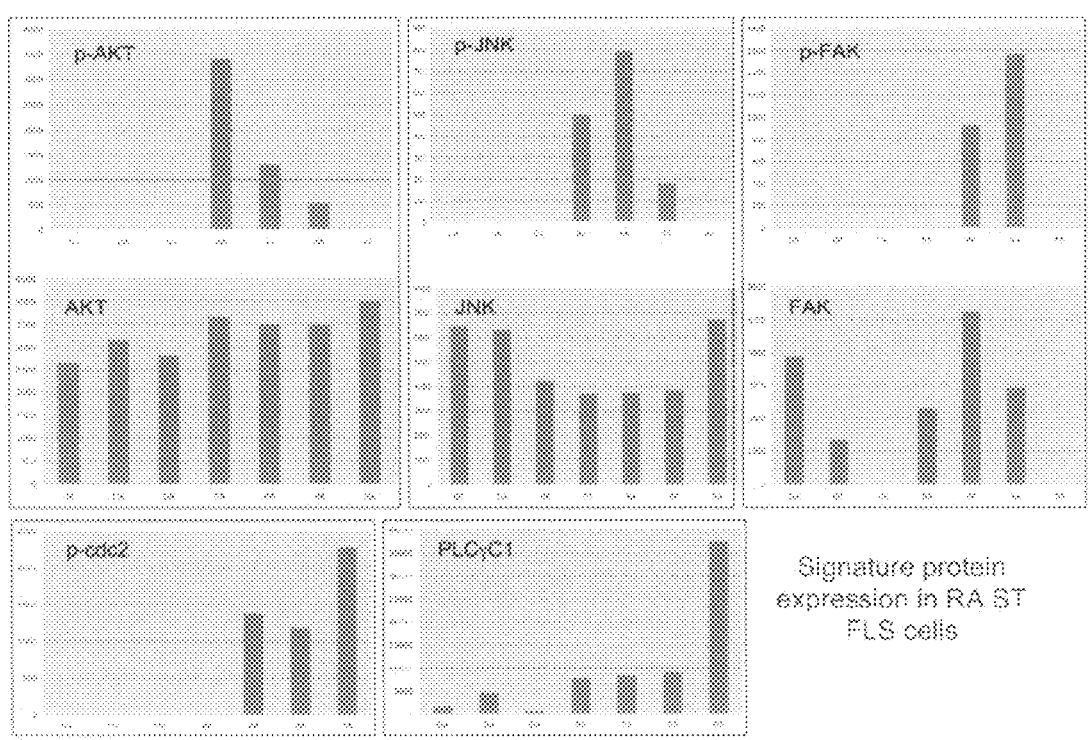
FIG. 3 shows the protein expression in synovial tissue fibroblast-like synovial cells derived from individuals with rheumatoid arthritis or osteoarthritis.

In parallel, protein extracted from the RA, OA and surgical trauma ST FLS cells was analyzed using the BD BioSciences PowerBlot Western immunoarray technology platform. The full array allows 996 proteins to be interrogated, and the inventors have developed a customized mini-array that specifically interrogates phospho-proteins. In agreement with the data for distinct gene expression, distinct protein expression patterns were observed in the RA FLS cells compared to OA FLS cells (FIG. 2). RA FLS cells were activated as determined by higher levels of phospho-AKT, phospho-FAK, phospho-p38, JNK, cdc-2 and PLC-γ1 proteins (FIG. 3). The PI3K/AKT pathway plays an important role in balancing apoptosis and survival (14) and is involved in cell cycle progression, glucose metabolism and chemotaxis (15). RA fibroblasts show enhanced survival in response to TNF-a (16) and TGF-β (17) through an AKT-dependent pathway (17). Additionally, this pathway has also been implicated in TRAIL induced proliferation in RA fibroblasts (18). Activation of the insulin-like growth factor-1 receptor (IGF-1R) (19), IL-17 (20) and the IL-18 receptor (21) also effect signal transduction in an AKT-dependent manner to induce cytokine/chemokine or adhesion molecule synthesis in RA fibroblasts. Focal adhesion kinase (FAK) regulates anti-apoptotic pathways through PI3K-dependent and -independent pathways. FAK is a widely expressed cytoplasmic protein tyrosine kinase involved in integrin mediated signal transduction. B1 integrin signaling through FAK upregulates ICAM-1 and Fas in RA FLS cells (22). The JNK and p38 pathways are preferentially activated by stress, inflammatory cytokines and growth factors. TNF can signal through both JNK and p38 to activate AP-1 and NF-kB (23) and IL-1 upregulates MMP13 (24) and collagenase 1 (25) via the JNK pathway in RA FLS cells. The entry of all cells into mitosis is regulated by cdc2 and increased cdc2 phosphorylation has been reported in RA fibroblasts and may be involved in aberrant mitosis (26). Viewed altogether, the data confirms that multiple genes and signaling pathways are activated in RA FLS cells contributing to the distinct phenotype of these cells.

Example 2

Fibrocytes in RA

RA is a complex heterogeneous disease. Hyperproliferation of FLS cells is considered to be a major contributor to pannus formation; however, little direct evidence supports hyperproliferation of these cells in vivo. Few mitotic figures are observed, thymidine uptake only occurs in a percentage of the cells (27) and FLS cells divide very slowly in culture (28). Decreased senescence in FLS cells may occur and RA FLS cells have been shown to retain telomerase activity (29), but these cells are not immortalized in vitro (29) (30). The outgrowth of FLS cells in the ST of affected RA joints is, therefore an enigma, and one possible explanation might be that FLS cells are recruited from the circulation. Many years ago, a circulating population of fibroblasts-like cells, was identified (31). More recently, these cells have been characterized further, designated as fibrocytes, and implicated in influencing disease development in tumor biology, scleroderma, asthma and pulmonary fibrosis (32) (33) (34) (35).

Fibrocytes are unique circulating cells that are relatively rare in the circulation, comprising only 0.1-1% of the white blood cells. Characterization of these cells has been predominantly by FACS staining of cells cultured for up to two weeks ex vivo and relatively little work has been performed in vivo. In vitro, fibrocytes have a unique phenotype and express markers of both stromal cells and hematopoietic cells, including: fibronectin, collagen, prolyl 4-hydroxylase, CD11a, CD11b, CD13, CD18, CD45RO, ICAM1, CD80, CD86, CXCR4, CCR7 and CCR5 (32) (36). Fibrocytes originate from the bone marrow (37) and arise from a CD14+ve pool of cells in the circulation, but fibrocytes themselves become CD14– (38). At the time of culture, these cells express CD34 and CD45 (33). When cultured ex vivo, these cells become adherent and develop a spindle-shaped morphology (33) (39) and downregulate CD45 and CD34. Three weeks after culture these cells express the myofibroblast marker, a-smooth muscle actin (SMA) (33), and have the ability to contract collagen gels in vitro (38). Ex vivo cultured fibrocytes differentiated into a-SMA expressing cells when directly co-cultured with T cells or upon TGF-b stimulation (38). Fibrocyte differentiation is inhibited by serum amyloid P (SAP) (36). Recently, in vivo evidence indicates that the fibrocyte population contributes to the myofibroblast population in a murine wound healing model (37). Fibrocytes secrete collagen and fibronectin, thereby contributing to granulation formation, and they are contractile, enhancing wound contraction and healing. They have also been shown to present antigen (40) and can secrete chemokines, cytokines and angiogenic factors (32), suggesting that fibrocytes contribute to both inflammation and its resolution.

Increased myofibroblast-like cells in the joint are observed in RA and correlate with the degree of inflammatory synovitis. It has been suggested that RA myofibroblasts originate from the circulating fibrocyte population (41) (42). The percentage of a-SMA expressing cells in RA patients varies from 1-30% (43) and the inventors have observed upregulated a-SMA gene expression in RA FLS cells (FIG. 1). Whether these myofibroblasts were derived locally, or were recruited from the circulating pool, is unclear. Certainly, circulating endothelial progenitor cells are increased during the onset of collagen induced arthritis, likely contributing to neoangiogenesis in affected tissues (Kurosaka et al 2005). Endothelial precursors are recruited in RA (44) and increased circulating endothelial precursors are observed in murine CIA (45) and in patients with RA (46). The inference is that circulating endothelial precursors will traffic to affected RA joints to promote the neoangiogenesis. Given that fibrocytes express CCR3, CCR5 and CCR7, and the cognate ligands for these receptors are found in synovial fluid, it is likely that fibrocytes will also traffic to the inflamed RA joint. Indeed, RA FLS cells expressed higher levels of some fibrocyte markers including: CCR5, CXCR4, CD54, CD18, CD11b and CD45 (FIG. 1). Fibrocytes and fibroblasts can differentiate into a-SMA expressing myofibroblasts upon stimulation with TGF-b Notably, increased levels of TGF-b are present in RA STs. Myofibroblast transformation involves activation of adhesion and integrin signaling through FAK and AKT pathways (47). TGF-b promotes AKT-dependent survival of mesenchymal cells through p38 MAPK-induced growth factor secretion (48). Constitutive phosphorylation of FAK is involved in myofibroblast differentiation in scleroderma (49). Apparently, many of the pathways the inventors have identified as potentially activated in the RA FLS cells have been implicated in fibrocyte differentiation.

Example 3

Signal Taxonomy in Defined RA Cell Populations

Changes in intracellular protein levels, subcellular localization, or activation state are considered to be reflective of a cell's capabilities or functions. Some of these events are relatively transitory—such as some phosphorylation of proteins in cell signaling cascades. Some of the relevant cell populations are so rare as to make their isolation for standard biochemical analysis nearly impossible. Remodeling of such cell signaling mechanisms drives disease pathogenesis contributing to immune cell dysregulation despite intense therapy regimens. Therefore, to understand how signaling networks are remodeled in RA there is a need to measure complex populations of immune system cells and phenotype them not only for their cell lineage status, but also for their relative activation state.

Studies in human myeloid leukemia have shown that signaling can be mapped at the individual cell level by flow cytometry and have demonstrated links between oncogene mutations and patterns of proliferative signaling in tumors (50). Furthermore, this work suggested that a tumor could be described by its signal transduction potential and that this status stratified patient risk of relapse following chemotherapy. Since RA is a systemic and chronic inflammatory autoimmune disease that targets synovial joints, disease pathogenesis is multifactorial and extends beyond T or FLS cell mediated destruction of cartilage. Production of pro-inflammatory cytokines such as TNFa and IL-1β by activated monocytes and macrophages contribute to tissue destruction by activation of chondrocytes and fibroblasts that release metalloproteinases and collagenases into the synovial cavity. Cartilage loss and bone erosion are physical manifestations of disease progression. Additional blood borne compartments, such as B cells, contribute to production of autoantibodies and rheumatoid factor and have been regarded as playing important roles. Both T and B cell lymphocyte deregulation, as well as the involvement of chondrocytes and fibroblasts suggest a dynamic interaction of cell-to-cell communications contribute to disease pathogenesis of RA.

The nature of the intracellular pathways activated with most primary immune cell interactions is not well understood in vivo and less clear in disease states. In many cases it is only understood using derived cell lines, in vitro, and at best is often accomplished by lysis of cells and western immunoblots of total cellular material. Therefore significant information on population variations that exist is missed and advances in genomics and proteomic technologies that rely on lysate material do not access the heterogeneous subsets that exist in the immune system.

Multiparameter flow cytometric analysis allows for small subpopulations to be discerned using cell surface markers—representing different cellular subsets, differentiation or activation states.

The inventors developed a series of assay systems for flow cytometric based biochemical analysis at the single cell level for kinase and phospho-protein profiling. Measurement of up to 12 simultaneous protein or kinase events per cell for studying signaling events in primary cells are possible with these systems (51) (52) (53) (54). This allows for unprecedented study of signaling in autoimmune diseases as immunocytes are particularly amenable to these techniques.

Underlying the gross dysfunctionality of autoimmunity are the signaling systems that drive their actions. The last two decades of research have uncovered numerous pathways leading from surface receptors to gene regulation. Many of these pathways, if not all, at one point or another pass signals through phosphorylation or dephosphorylation events on proteins or lipids. Integration of signaling events leads to relocalization of proteins within cells, such as with translocation of proteins to the nucleus. Until recently, measurement of such events has been limited to cell lines or bulk lysis assays. Interpretation of such assays is considered a pale rendition of what we know is the intricacy of complex population primary cell events. Therefore a true understanding of the nature of signaling dysfunctions during disease processes in heterogeneous patient samples or animal model systems has been beyond reach.

It can be hypothesized that the activation profiles of proteins, such as phospho-proteins that drive proliferation and activation signaling cascades will differ, in disease states, both from a "normal" profile of a non-disease presence and from other samples with significantly different pathology. During disease pathogenesis, cells are accessing different environmental cues, or ignoring those that might be attempting to block their replication (or induce their apoptosis). As such, it would be expected that there would be underlying differences in the activation profiles of certain phospho-proteins across immune and non-immune cells in RA pathogenesis.

Therefore, with sufficient understanding of relationships between cell signaling and immunopathology, activation profiles of phospho-proteins could indicate the presence of individual aggressive cell subsets within a complex population of cells. Since it is hard to predict which kinases might be relevant in different cell subsets, this hypothesis has limited utility in the absence of a high throughput manner to measure many kinases. However, if one could measure dozens of kinase activation profiles—or their target proteins—simultaneously—there is the opportunity to generate invaluable information about the role of signaling events in rheumatologic disease, test hypotheses of signaling systems in response to various therapies, as well as develop diagnostic indicators based on kinase profiles. Finally, it might be possible to reveal signaling states that are hidden from obvious view if one were only looking at basal phosphorylation states.

Knowledge of intracellular signaling differences among arthritic immune cells could therefore provide the basis for an improved autoimmune classification system. Importantly, such a classification system would go beyond a simple signature, but could be used to infer mechanism associated with the signature.

In the present studies the inventors have shown that by surveying phospho-protein/basal phosphorylation states, the underlying dysregulated signaling nodes in primary human RA samples can be revealed and the identification of signaling pathology profiles can be enabled. Specifically, based on our gene and protein expression data elaborating an emerging phenotype for the RA FLS, the inventors examined peripheral blood mononuclear cells (PBMC) for a fibrocyte population with similar properties. At the outset, PBMC from healthy individuals were analyzed by multiparameter flow cytometry to identify the fibrocyte population. The data in FIG. 4 indicate that immunostaining for collagen, CD34, CD45, prolyl 4-hydroxylase and CD14 identifies this precursor fibrocyte population. In subsequent experiments, multiparametric staining using both surface and intracellular stains was employed to determine the activation status of the circulating fibrocytes in the PBMC of healthy individuals, patients with early RA and later stage disease. Early RA was defined as patients within the first year of onset of symptoms with 3 swollen joints. Changes in the signaling status that occurs during the functional activation of this fibrocyte population might include phosphorylation-activation of STATs, Erk and MAP kinases. Accordingly, using polychromatic analyses the inventors examined the frequency of activated fibrocytes, focusing on STAT3, STAT5, Erk and p38 MAPK. CD3-CD45+collagen+ fibrocytes were stained for phospho-STAT3 (FIG. 5), phospho-STAT5 (FIG. 6), phospho-Erk (FIG. 7) and phospho-p38 MAPK (FIG. 8) and the frequency of staining determined in each patient population: healthy individuals (n=20), early RA patients (n=8), late stage disease RA patients (n=4). These data indicate that the frequency of phospho-staining for these signaling effectors in the RA patient fibrocytes is significantly higher (panels B) than that seen in fibrocytes from healthy individuals.

Example 4

Collagen-Induced Arthritis Model

Collagen-induced arthritis (CIA) is a widely used model of rheumatoid arthritis (55) (56). Mice with CIA exhibit obvious swelling of paws and joints as compared to control animals (FIG. 12A). The mice were given a clinical disease score based on the severity of the disease (FIG. 12B). FIG. 12C shows immunohistochemistry staining of the joint.

The inventors collected PBMC by cardiac puncture at different stages of disease and analyzed the cells by FACS for positive staining to α-SMA and collagen. As can be seen in FIGS. 12D and E, the number of circulating fibrocytes is higher in mice with higher disease scores.

Figure 13:
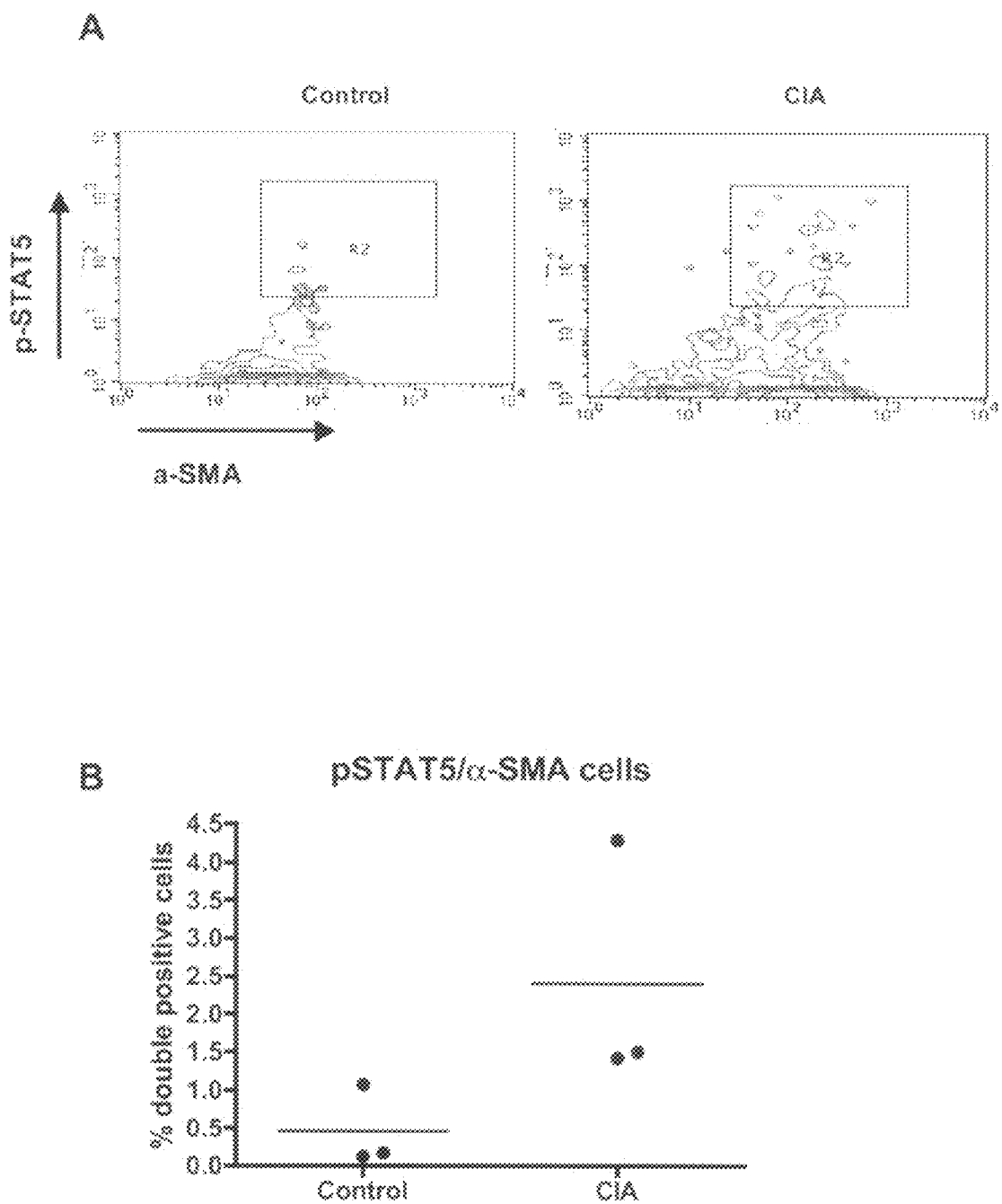
FIG. 13 shows evidence of increased p-STAT5 in circulating fibrocytes from animals with early stages of CIA. PBMC were isolated from the peripheral blood of control and CIA mice at stage 1-2. The cells were stained for Collagen I-Alexa647, α-SMA-FITC and p-STAT5-PE and analyzed by FACS. The ColI+ cells were gated and the percentage of α-SMA/p-STAT5 double positive cells are shown (A, R2 gate and B).

The circulating fibrocytes also showed increased p-STAT5 in the animals with CIA as compared to the control animals (FIG. 13).

Figure 14:
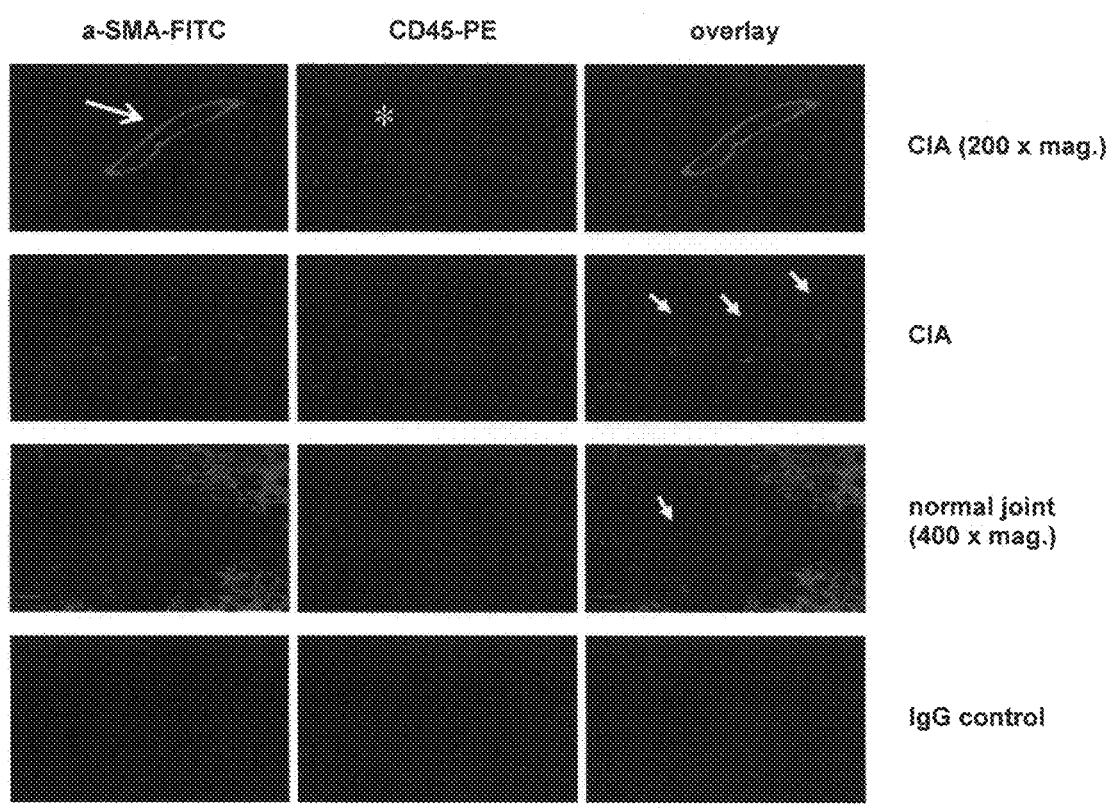
FIG. 14 shows immunohistochemistry of paraffin embedded joints from mice with collagen induced arthritis stained with α-SMA-FITC (green) and CD45-PE (red). α-SMA also stains smooth muscle and is clearly identified surrounding an artery (open arrow). A profound cellular influx of leukocytes is evident (*) in the CIA joint tissue and the majority of these cells do not stain with α-SMA (overlay). α-SMA/CD45 fibrocytes/myofibroblasts were easily identified in the CIA joints (closed arrow) and were more abundant than in normal joints.
Figure 15:
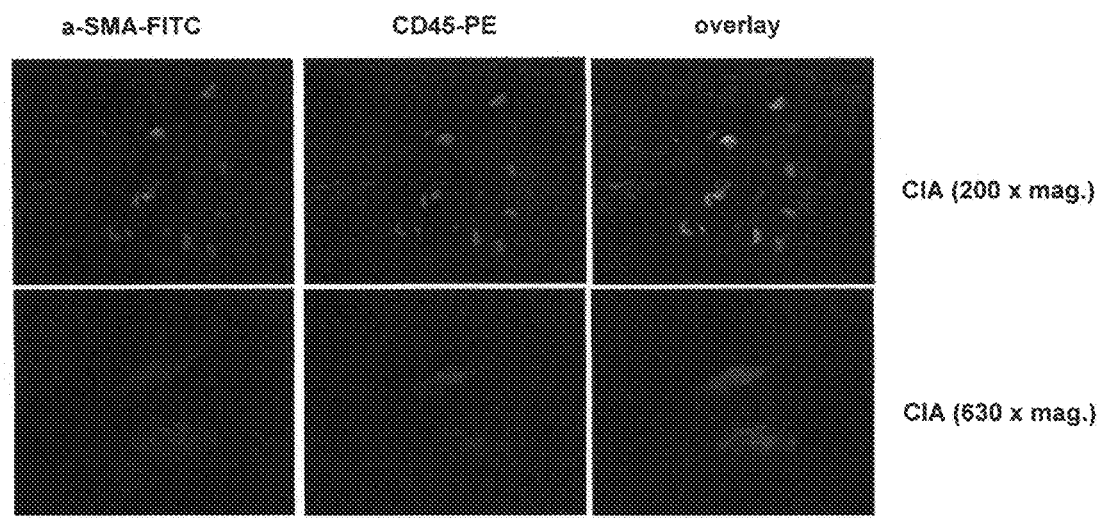
FIG. 15 shows immunohistochemistry of plastic embedded joints from mice with collagen induced arthritis stained with α-SMA-FITC (green) and CD45-PE (red). α-SMA/CD45 double positive fibrocytes/myofibroblasts were identified in the CIA joints.

FIGS. 14 and 15 show the results of immunohistochemistry of samples from mice with CIA as compared to controls.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Probe set ID number | Public ID number (NCBI) | Target description | Chromosomal location | Unigene ID | Gene Title | Gene Symbol |
|---|---|---|---|---|---|---|
| 209765_at | Y13786 | gb:Y13786.2 /DB_XREF = gi:12053590 /FEA = FLmRNA /CNT = 58 /TID = Hs.278679.1 /TIER = Stack /STK = 24 /UG = Hs.278679 /LL = 8728 /UG_GENE = ADAM19 /DEF = Homo sapiens mRNA for meltrin-betaADAM 19 homologue. /PROD = meltrin-betaADAM 19 homologue /FL = gb: AF311317.1 | chr5q32-q33 | Hs.289368 | ADAM metallopeptidase domain 19 (meltrin beta) | ADAM19 |
| 206134_at | NM_014479 | gb: NM_014479.1 /DB_XREF = gi:7667318 /GEN = M12.219 /FEA = FLmRNA /CNT = 21 /TID = Hs.145296.0 /TIER = FL + Stack /STK = 14 /UG = Hs.145296 /LL = 27299 /DEF = Homo sapiens disintegrin protease (M12.219), mRNA. /PROD = disintegrin protease /FL = gb: NM_014479.1 | chr8p21.2 | Hs.145296 | ADAM-like, decysin 1 | ADAMDEC1 |
| 206513_at | NM_004833 | gb: NM_004833.1 /DB_XREF = gi:4757733 /GEN = AIM2 /FEA = FLmRNA /CNT = 15 /TID = Hs.105115.0 /TIER = FL /STK = 7 /UG = Hs.105115 /LL = 9447 /DEF = Homo sapiens absent in melanoma 2 (AIM2), mRNA. /PROD = absent in melanoma 2 /FL = gb: AF024714.1 gb: NM_004833.1 | chr1q22 | Hs.105115 | absent in melanoma 2 | AIM2 |
| 218332_at | NM_018476 | gb: NM_018476.1 /DB_XREF = gi:8923715 /GEN = HBEX2 /FEA = FLmRNA /CNT = 116 /TID = Hs.283719.0 /TIER = FL + Stack /STK = 54 /UG = Hs.283719 /LL = 55859 /DEF = Homo sapiens uncharacterized hypothalamus protein HBEX2 (HBEX2), mRNA. /PROD = uncharacterized hypothalamus protein HBEX2 | chrxq21-q23 | Hs.334370 | brain expressed, X-linked 1 | BEX1 |
| 205715_at | NM_004334 | gb: NM_004334.1 /DB_XREF = gi:4757873 /GEN = BST1 /FEA = FLmRNA /CNT = 43 /TID = Hs.169998.0 /TIER = FL + Stack /STK = 21 /UG = Hs.169998 /LL = 683 /DEF = Homo sapiens bone marrow stromal cell antigen 1 (BST1), mRNA. /PROD = bone marrow stromal cell antigen 1 precursor /FL = gb: D21 | chr4p15 | Hs.169998 | bone marrow stromal cell antigen 1 | BST1 |
| 202953_at | NM_000491 | gb: NM_000491.2 /DB_XREF = gi:11038661 /GEN = C1QB /FEA = FLmRNA /CNT = 135 /TID = Hs.8986.0 /TIER = FL + Stack /STK = 16 /UG = Hs.8986 /LL = 713 /DEF = Homo sapiens complement component 1, q subcomponent, beta polypeptide (C1QB), mRNA. /PROD = complement component 1, q subcompon | chr1p36.3-p34.1 | Hs.8986 | complement component 1, q subcomponent, beta polypeptide | C1QB |
| 209906_at | U62027 | gb: U62027.1 /DB_XREF = gi:1511643 /GEN = HNFAG09 /FEA = FLmRNA /CNT = 43 /TID = Hs.155935.0 /TIER = FL + Stack /STK = 19 /UG = Hs.155935 /LL = 719 /DEF = Human anaphylatoxin C3a receptor (HNFAG09) mRNA, complete cds. /PROD = anaphylatoxin C3a receptor /FL = gb: U62027.1 gb: U28488.1 | chr12p13.31 | Hs.155935 | complement component 3a receptor 1 | C3AR1 |
| 229824_at | AL133706 | gb:AL133706 /DB_XREF = gi:6601894 /DB_XREF = DKFZp761O0410 /CLONE = DKFZp761O0410_s1 /TIER = Stack /STK = 28 /UG = Hs.4257 /UG_TITLE = ESTs | chr9q22.1-q22.2 | Hs.4257 | Endothelial differentiation, sphingolipid G-protein-coupled receptor, 3 | C9orf47 |
| 206407_s_at | NM_005408 | gb: NM_005408.1 /DB_XREF = gi:4885586 /GEN = SCYA13 /FEA = FLmRNA /CNT = 19 /TID = Hs.11383.0 /TIER = FL + Stack /STK = 6 /UG = Hs.11383 /LL = 6357 /DEF = Homo sapiens small inducible cytokine subfamily A (Cys-Cys), member 13 (SCYA13), mRNA. /PROD = small inducible cytokine subfamily A | chr7q11.2 | Hs.414629 | chemokine (C—C motif) ligand 13 | CCL13 |
| 209924_at | AB000221 | gb:AB000221.1 /DB_XREF = gi:2289718 /GEN = PARC /FEA = FLmRNA /CNT = 50 /TID = Hs.16530.0 /TIER = FL + Stack /STK = 21 /UG = Hs.16530 /LL = 6362 /DEF = Homo sapiens mRNA for CC chemokine, complete cds. /PROD = CC chemokine /FL = gb: AB000221.1 gb: NM_002988.1 | chr7q11.2 | Hs.16530 | chemokine (C—C motif) ligand 18 (pulmonary and activation-regulated) | CCL18 |
| 216598_s_at | S69738 | gb:S69738.1 /DB_XREF = gi:545464 /GEN = MCP-1 /FEA = mRNA /CNT = 1 /TID = Hs.303649.1 /TIER = ConsEnd /STK = 0 /UG = Hs.303649 /LL = 6347 /DEF = MCP-1 = monocyte chemotactic protein (human, aortic endothelial cells, mRNA, 661 nt). /PROD = MCP-1 | chr17q11.2-q21.1 | Hs.303649 | chemokine (C—C motif) ligand 2 | CCL2 |
| 205114_s_at | NM_002983 | gb: NM_002983.1 /DB_XREF = gi:4506842 /GEN = SCYA3 /FEA = FLmRNA /CNT = 78 /TID = Hs.73817.0 /TIER = FL + Stack /STK = 30 /UG = Hs.73817 | chr7q21.1 | Hs.512304 | chemokine (C—C motif) ligand 3 /// chemokine (C—C motif) ligand 3- | CCL3 /// CCL3L1 /// |

TABLE 1-continued

| Probe set ID number | Public ID number (NCBI) | Target description | Chromosomal location | Unigene ID | Gene Title | Gene Symbol |
|---|---|---|---|---|---|---|
| 214038_at | AI984980 | /LL = 6348 /DEF = Homo sapiens small inducible cytokine A3 (homologous to mouse Mip-1a) (SCYA3), mRNA. /PROD = small inducible cytokine A3 (hom gb: AI984980 /DB_XREF = gi: 5812257 /DB_XREF = wr88g11.x1 /CLONE = IMAGE: 2494820 /FEA = FLmRNA /CNT = 29 /TID = Hs.271387.0 /TIER = Stack /STK = 16 /UG = Hs.271387 /LL = 6355 /UG_GENE = SCYA8 /UG_TITLE = small inducible cytokine subfamily A (Cys-Cys), member 8 (monocyte chemotacti | chr17q11.2 | Hs.271387 | like 1 /// chemokine (C—C motif) ligand 3-like 3 chemokine (C—C motif) ligand 8 | CCL3L3 CCL8 |
| 209583_s_at | AF063591 | gb: AF063591.1 /DB_XREF = gi: 12002013 /FEA = FLmRNA /CNT = 108 /TID = Hs.79015.0 /TIER = FL + Stack /STK = 37 /UG = Hs.79015 /LL = 4345 /UG_GENE = MOX2 /DEF = Homo sapiens brain my033 protein mRNA, complete cds. /PROD = brain my033 protein /FL = gb: AF063591.1 | chr3q12-q13 | Hs.79015 | CD200 antigen | CD200 |
| 207277_at | AF290886 | gb: AF290886.1 /DB_XREF = gi: 13383467 /FEA = FLmRNA /CNT = 8 /TID = Hs.278694.0 /TIER = FL/STK = 0 /UG = Hs.278694 /LL = 30835 /UG_GENE = CD209 /DEF = Homo sapiens DC-SIGN mRNA, complete cds. /PROD = DC-SIGN /FL = gb: AF290886.1 gb: M98457.1 gb: NM_021155.1 | chr19p13 | Hs.278694 | CD209 antigen | CD209 |
| 203416_at | NM_000560 | gb: NM_000560.1 /DB_XREF = gi: 10834971 /GEN = CD53 /FEA = FLmRNA /CNT = 137 /TID = Hs.82212.0 /TIER = FL + Stack /STK = 64 /UG = Hs.82212 /LL = 963 /DEF = Homo sapiens CD53 antigen (CD53), mRNA. /PROD = CD53 antigen /FL = gb: NM_000560.1 gb: M60871.1 gb: M37033.1 | chr1p13 | Hs.443057 | CD53 antigen | CD53 |
| 218451_at | NM_022842 | gb: NM_022842.1 /DB_XREF = gi: 12383093 /GEN = FLJ22969 /FEA = FLmRNA /CNT = 97 /TID = Hs.146170.0 /TIER = FL + Stack /STK = 16 /UG = Hs.146170 /LL = 64866 /DEF = Homo sapiens hypothetical protein FLJ22969 (FLJ22969), mRNA. /PROD = hypothetical protein FLJ22969 /FL = gb: NM_022842.1 | chr3p21.31 | Hs.146170 | CUB domain containing protein 1 | CDCP1 |
| 217428_s_at | X98568 | gb: X98568 /DB_XREF = gi: 1405722 /FEA = DNA /CNT = 2 /TID = Hs.179729.1 /TIER = ConsEnd /STK = 0 /UG = Hs.10029.0 /LL = 1300 /UG_GENE = COL10A1 /UG_TITLE = collagen, type X, alpha 1 (Schmid metaphyseal chondrodysplasia) /DEF = H. sapiens type X collagen gene | chr6q21-q22 | Hs.179729 | collagen, type X, alpha 1(Schmid metaphyseal chondrodysplasia) | COL10A1 |
| 205159_at | AV756141 | gb: AV756141 /DB_XREF = gi: 10913989 /DB_XREF = AV756141 /CLONE = BMFAKF10 /FEA = FLmRNA /CNT = 51 /TID = Hs.285401.0 /TIER = Stack /STK = 20 /UG = Hs.285401 /LL = 1439 /UG_GENE = CSF2RB /UG_TITLE = colony stimulating factor 2 receptor, beta, low-affinity (granulocyte-macrophage) | chr22q13.1 | Hs.285401 | colony stimulating factor 2 receptor, beta, low-affinity (granulocyte-macrophage) /// colony stimulating factor 2 receptor, beta, low-affinity (granulocyte-macrophage) | CSF2RB |
| 201487_at | NM_001814 | gb: NM_001814.1 /DB_XREF = gi: 4503140 /GEN = CTSC /FEA = FLmRNA /CNT = 257 /TID = Hs.10029.0 /TIER = FL + Stack /STK = 125 /UG = Hs.10029 /LL = 1075 /DEF = Homo sapiens cathepsin C (CTSC), mRNA. /PROD = cathepsin C /FL = gb: NM_001814.1 | chr11q14.1-q14.3 | Hs.128065 | cathepsin C | CTSC |
| 203666_at | NM_000609 | gb: NM_000609.1 /DB_XREF = gi: 10834987 /GEN = SDF1 /FEA = FLmRNA /CNT = 114 /TID = Hs.237356.0 /TIER = FL + Stack /STK = 60 /UG = Hs.237356 /LL = 6387 /DEF = Homo sapiens stromal cell-derived factor 1 (SDF1), mRNA. /PROD = stromal cell-derived factor 1 /FL = gb: L36033.1 gb: NM_00060 | chr10q11.1 | Hs.436042 | chemokine (C-X-C motif) ligand 12 (stromal cell-derived factor 1) | CXCL12 |
| 223553_s_at | BC004564 | gb: BC004564.1 /DB_XREF = gi: 13528734 /FEA = FLmRNA /CNT = 30 /TID = Hs.122559.1 /TIER = FL + Stack /STK = 12 /UG = Hs.122559 /DEF = Homo sapiens, Similar to hypothetical protein FLJ22570, clone MGC: 10476, mRNA, complete cds. /PROD = Similar to hypothetical protein FLJ22570 / | chr5q35.3 | Hs.122559 | docking protein 3 | DOK3 |
| 219454_at | NM_015507 | gb: NM_015507.2 /DB_XREF = gi: 13124887 /GEN = EGFL6 /FEA = FLmRNA /CNT = 163 /TID = Hs.12844.0 /TIER = FL + Stack /STK = 40 /UG = Hs.12844 /LL = 25975 /DEF = Homo sapiens EGF-like-domain, multiple 6 (EGFL6), | chrxp22 | Hs.12844 | EGF-like-domain, multiple 6 | EGFL6 |

TABLE 1-continued

| Probe set ID number | Public ID number (NCBI) | Target description | Chromosomal location | Unigene ID | Gene Title | Gene Symbol |
|---|---|---|---|---|---|---|
| 1554899_s_at | BC020763 | mRNA./PROD = epidermal growth factor-like protein 6precursor/FL = gb: NM_/gb: BC020763.1/DB_XREF = gi: 18088866/TID = Hs2.433300.2/CNT = 3/FEA = FLmRNA/TIER = FL/STK = 1/LL = 2207/UG_GENE = FCER1G/UG = Hs.433300/DEF = Homo sapiens, Similar to Fc fragment of IgE, high affinity I, receptor for; gamma polypeptide, clone MGC: 22620 IMAGE: 4704442 | chr1q23 | Hs.433300 | Fc fragment of IgE, high affinity I, receptor for; gamma polypeptide | FCER1G |
| 203561_at | NM_021642 | gb: NM_021642.1/DB_XREF = gi: 11056051/GEN = FCGR2A/FEA = FLmRNA/CNT = 142/TID = Hs.78864.0/TIER = FL + Stack/STK = 8/UG = Hs.78864/LL = 2212/DEF = Homo sapiens Fc fragment of IgG, low affinity IIa, receptor for (CD32) (FCGR2A), mRNA./PROD = Fc fragment of IgG, low affi | chr1q23 | Hs.352642 | Fc fragment of IgG, low affinity IIa, receptor (CD32) | FCGR2A |
| 218468_s_at | AF154054 | gb: AF154054.1/DB_XREF = gi: 10863087/GEN = DRM/FEA = FLmRNA/CNT = 228/TID = Hs.40098.0/TIER = FL + Stack/STK = 20/UG = Hs.40098/LL = 26585/DEF = Homo sapiens DRM (DRM) mRNA, complete cds./PROD = DRM/FL = gb: NM_013372.1 gb: AF154054.1 | chr15q13-q15 | Hs.40098 | gremlin 1, cysteine knot superfamily, homolog (Xenopus laevis) | GREM1 |
| 217478_s_at | X76775 | gb: X76775/DB_XREF = gi: 512468/FEA = DNA_1/CNT = 1/TID = Hs.77522.1/TIER = ConsEnd/STK = 0/UG = Hs.77522/LL = 3108/UG_GENE = HLA-DMA/UG_TITLE = major histocompatibility complex, class II, DM alpha/DEF = H. sapiens HLA-DMA gene | chr6p21.3 | Hs.351279 | major histocompatibility complex, class II, DM alpha | HLA-DMA |
| 203932_at | NM_002118 | gb: NM_002118.1/DB_XREF = gi: 4504398/GEN = HLA-DMB/FEA = FLmRNA/CNT = 91/TID = Hs.1162.0/TIER = FL + Stack/STK = 49/UG = Hs.1162/LL = 3109/DEF = Homo sapiens major histocompatibility complex, class II, DM beta (HLA-DMB), mRNA./PROD = major histocompatibility complex, c | chr6p21.3 | Hs.1162 | major histocompatibility complex, class II, DM beta /// major histocompatibility complex, class II, DM beta | HLA-DMB |
| 211991_s_at | M27487 | gb: M27487.1/DB_XREF = gi: 703088/GEN = HLA-DPA1/FEA = FLmRNA/CNT = 358/TID = Hs.914.0/TIER = FL + Stack/STK = 139/UG = Hs.914/DEF = Homo sapiens MHC class II DPw3-alpha-1 chain mRNA, complete cds./PROD = MHC class II DP3-alpha/FL = gb: M27487.1 | chr6p21.3 | Hs.914 | major histocompatibility complex, class II, DP alpha 1 | HLA-DPA1 |
| 212671_s_at | BG397856 | gb: BG397856/DB_XREF = gi: 13291304/DB_XREF = 60243895F1/CLONE = IMAGE: 4564956/FEA = mRNA/CNT = 167/TID = Hs.198253.2/TIER = Stack/STK = 59/UG = Hs.198253/LL = 3117/UG_GENE = HLA-DQA1/UG_TITLE = major histocompatibility complex, class II, DQ alpha 1 | chr6p21.3 | Hs.387679 | major histocompatibility complex, class II, DQ alpha 1 /// major histocompatibility complex, class II, DQ alpha 2 | HLA-DQA1 /// HLA-DQA2 |
| 208894_at | M60334 | gb: M60334.1/DB_XREF = gi: 188255/GEN = HLA-DRA/FEA = FLmRNA/CNT = 470/TID = Hs.76807.0/TIER = FL/STK = 0/UG = Hs.76807/LL = 3122/DEF = Human MHC class II HLA-DR-alpha mRNA, complete cds./PROD = cell surface glycoprotein/FL = gb: M60334.1 gb: NM_019111.1 | chr6p21.3 | Hs.409805 | major histocompatibility complex, class II, DR alpha /// major histocompatibility complex, class II, DR alpha | HLA-DRA |
| 204670_x_at | NM_002125 | gb: NM_002125.1/DB_XREF = gi: 4504412/GEN = HLA-DRB5/FEA = FLmRNA/CNT = 62/TID = Hs.308026.0/TIER = FL/STK = 1/UG = Hs.308026/LL = 3127/DEF = Homo sapiens major histocompatibility complex, class II, DR beta 5 (HLA-DRB5), mRNA./PROD = major histocompatibility complex, | chr6p21.3 | Hs.308026 | major histocompatibility complex, class II, DR beta 1 | HLA-DRB1 |
| 209312_x_at | U65585 | gb: U65585.1/DB_XREF = gi: 5478215/GEN = HLA-DRB4/CNT = 126/TID = Hs.180255.0/TIER = FL/STK = 0/UG = Hs.180255/LL = 3123/DEF = Homo sapiens MHC class II antigen (HLA-DRB1) mRNA, HLA-DRB1*PBL allele, complete cds./PROD = MHC class II antigen/FL = gb: NM_0021 | | | major histocompatibility complex, class II, DR beta /// major histocompatibility complex, class II, DR beta 1 | HLA-DRB1 |
| 208306_x_at | NM_021983 | gb: NM_021983.2/DB_XREF = gi: 11875206/GEN = HLA-DRB4/FEA = FLmRNA/CNT = 2/TID = Hs.293934.0/TIER = FL/STK = 0/UG = Hs.293934/LL = 3126/DEF = Homo sapiens major histocompatibility | chr6p21.3 | Hs.308026 | Major histocompatibility complex, class II, DR beta 3 | HLA-DRB3 |

TABLE 1-continued

| Probe set ID number | Public ID number (NCBI) | Target description | Chromosomal location | Unigene ID | Gene Title | Gene Symbol |
|---|---|---|---|---|---|---|
| 217362_x_at | AF005487 | complex, class II, DR beta 4 (HLA-DRB4), mRNA. /PROD = major histocompatibility complex, gb: AF005487.1 /DB_XREF = gi: 5915893 /FEA = mRNA /CNT = 2 /TID = Hs.167385.0 /TIER = ConsEnd /STK = 0 /UG = Hs.167385 /UG_TITLE = Homo sapiens MHC class II antigen HLA-DRB6 mRNA, partial cds /DEF = Homo sapiens MHC class II antigen (DRB6) mRNA, HLA-DRB6*0201 allele, sequence | chr6p21.3 | | major histocompatibility complex, class II, DR beta 6 (pseudogene) | HLA-DRB6 |
| 229400_at | AW299531 | gb: AW299531 /DB_XREF = gi: 6709208 /DB_XREF = xs51a03.x1 /CLONE = IMAGE: 2773132 /FEA = EST /CNT = 17 /TID = Hs.188023.0 /TIER = Stack /STK = 10 /UG = Hs.188023 /UG_TITLE = ESTs | chr2q31.1 | Hs.123070 | homeo box D10 | HOXD10 |
| 209374_s_at | BC001872 | gb: BC001872.1 /DB_XREF = gi: 12804852 /FEA = FLmRNA /CNT = 302 /TID = Hs.302063.0 /TIER = FL + Stack /STK = 207 /UG = Hs.302063 /LL = 3507 /UG_GENE = IGHM /DEF = Homo sapiens, clone MGC: 1228, mRNA, complete cds. /PROD = Unknown (protein for MGC: 1228) /FL = gb: BC002963.1 gb: BC001872 | chr14q32.33 | Hs.439852 | immunoglobulin heavy constant mu | IGHM |
| 214669_x_at | BG485135 | gb: BG485135 /DB_XREF = gi: 13417414 /DB_XREF = 602503756F1 /CLONE = IMAGE: 4617445 /FEA = mRNA /CNT = 101 /TID = Hs.325722.1 /TIER = ConsEnd /STK = 0 /UG = Hs.325722 /LL = 28875 /UG_GENE = IGKV3D-15 /UG_TITLE = immunoglobulin kappa variable 3D-15 | chr2p12 | Hs.377975 /// Hs.449606 /// Hs.494060 /// Hs.512126 /// Hs.534005 | Immunoglobulin kappa variable 1-5 | IGKC |
| 226218_at | BE217880 | gb: BE217880 /DB_XREF = gi: 8905198 /DB_XREF = hv31a11.x1 /CLONE = IMAGE: 3175004 /FEA = EST /CNT = 52 /TID = Hs.237868.1 /TIER = Stack /STK = 24 /UG = Hs.237868 /LL = 3575 /UG_GENE = IL7R /UG_TITLE = interleukin 7 receptor | chr5p13 | Hs.362807 | Interleukin 7 receptor | IL7R |
| 205786_s_at | NM_000632 | gb: NM_000632.2 /DB_XREF = gi: 6006013 /GEN = ITGAM /FEA = FLmRNA /CNT = 40 /TID = Hs.172631.0 /TIER = FL /STK = 1 /UG = Hs.172631 /LL = 3684 /DEF = Homo sapiens integrin, alpha M (complement component receptor 3, alpha; also known as CD11b (p170), macrophage antigen alpha pol | chr16p11.2 | Hs.172631 | integrin, alpha M (complement component receptor 3, alpha; also known as CD11b (p170), macrophage antigen alpha polypeptide) /// integrin, alpha M (complement component receptor 3, alpha; also known as CD11b (p170), macrophage antigen alpha polypeptide) | ITGAM |
| 202803_s_at | NM_000211 | gb: NM_000211.1 /DB_XREF = gi: 4557885 /GEN = ITGB2 /FEA = FLmRNA /CNT = 176 /TID = Hs.83968.0 /TIER = FL + Stack /STK = 80 /UG = Hs.83968 /LL = 3689 /DEF = Homo sapiens integrin, beta 2 (antigen CD18 (p95), lymphocyte function-associated antigen 1; macrophage antigen 1 (mac-1) | chr21q22.3 | Hs.375957 | integrin, beta 2 (antigen CD18 (p95), lymphocyte function-associated antigen 1; macrophage antigen 1 (mac-1) beta subunit) | ITGB2 |
| 228167_at | AW574798 | gb: AW574798 /DB_XREF = gi: 7246337 /DB_XREF = UI-HF-BK0-abh-e-04-0-UI.s1 /CLONE = IMAGE: 3056335 /FEA = mRNA /CNT = 35 /TID = Hs.43616.0 /TIER = Stack /STK = 18 /UG = Hs.43616 /UG_TITLE = Homo sapiens mRNA for FLJ00029 protein, partial cds | chr3q27.3 | Hs.439354 | kelch-like 6 (Drosophila) | KLHL6 |
| 205306_x_at | AI074145 | gb: AI074145 /DB_XREF = gi: 3400789 /DB_XREF = ov13a06.x1 /CLONE = IMAGE: 1637170 /FEA = FLmRNA /CNT = 48 /TID = Hs.107318.0 /TIER = Stack /STK = 10 /UG = Hs.107318 /LL = 8564 /UG_GENE = KMO /UG_TITLE = kynurenine 3-monooxygenase (kynurenine 3-hydroxylase) /FL = gb: NM_003679.1 gb: AF0 | chr1q42-q44 | Hs.409081 | kynurenine 3-monooxygenase (kynurenine 3-hydroxylase) | KMO |
| 201720_s_at | AI589086 | gb: AI589086 /DB_XREF = gi: 4598134 /FEA = FLmRNA /CNT = 274 /TID = Hs.79356.0 /CLONE = IMAGE: 2105634 /FEA = FLmRNA /CNT = 274 /TID = Hs.79356.0 /TIER = Stack /STK = 22 /UG = Hs.79356 /LL = 7805 /UG_GENE = LAPTM5 | chr1p34 | Hs.436200 | lysosomal associated multispanning membrane protein 5 | LAPTM5 |

TABLE 1-continued

| Probe set ID number | Public ID number (NCBI) | Target description | Chromosomal location | Unigene ID | Gene Title | Gene Symbol |
|---|---|---|---|---|---|---|
| 206140_at | NM_004789 | /UG_TITLE = Lysosomal-associated multispanning membrane protein-5 /FL = gb: NM_006762.1 gb: U | chr9q33-q34.1 | Hs.1569 | LIM homeobox 2 | LHX2 |
| 213909_at | AU147799 | gb: NM_004789.1 /DB_XREF = gi: 4758673 /GEN = LHX2 /FEA = FLmRNA /CNT = 18 /TID = Hs.1569.0 /TIER = FL /STK = 1 /UG = Hs.1569 /LL = 9355 /DEF = Homo sapiens LIM homeobox protein 2 (LHX2), mRNA. /PROD = LIM homeobox protein 2 /FL = gb: NM_004789.1 gb: AF124735.1 | chr3q29 | Hs.288467 | leucine rich repeat containing 15 | LRRC15 |
| 213975_s_at | AV711904 | gb: AU147799 /DB_XREF = gi: 11009320 /DB_XREF = AU147799 /CLONE = MAMMA1001744 /FEA = mRNA /CNT = 43 /TID = Hs.288467.0 /TIER = Stack /STK = 20 /UG = Hs.288467 /UG_TITLE = Homo sapiens cDNA FLJ12280 fis, clone MAMMA1001744 | chr19q13.4 /// chr12q15 | Hs.149924 | lysozyme (renal amyloidosis) /// leukocyte immunoglobulin-like receptor, subfamily B (with TM and ITIM domains), member 1 | LYZ /// LILRB1 |
| 203435_s_at | NM_007287 | gb: AV711904 /DB_XREF = gi: 10731210 /DB_XREF = AV711904 /CLONE = DCAAIF08 /FEA = mRNA /CNT = 21 /TID = Hs.277431.0 /TIER = Stack /STK = 8 /UG = Hs.277431 /UG_TITLE = Homo sapiens cDNA: FLJ23356 fis, clone HEP14919 | chr3q25.1-q25.2 | Hs.307734 | membrane metallo-endopeptidase (neutral endopeptidase, enkephalinase, CALLA, CD10) | MME |
| 204580_at | NM_002426 | gb: NM_007287.1 /DB_XREF = gi: 6042199 /GEN = MME /FEA = FLmRNA /CNT = 219 /TID = Hs.1298.2 /TIER = FL + Stack /STK = 59 /UG = Hs.1298 /LL = 4311 /DEF = Homo sapiens membrane metallo-endopeptidase (neutral endopeptidase, enkephalinase, CALLA, CD10) (MME), transcript variant 1 bis | chr11q22.3 | Hs.1695 | matrix metallopeptidase 12 (macrophage elastase) | MMP12 |
| 226844_at | AI375115 | gb: NM_002426.1 /DB_XREF = gi: 4505206 /GEN = MMP12 /FEA = FLmRNA /CNT = 72 /TID = Hs.1695.0 /TIER = FL + Stack /STK = 18 /UG = Hs.1695 /LL = 4321 /DEF = Homo sapiens matrix metalloproteinase 12 (macrophage elastase) (MMP12), mRNA. /PROD = matrix metalloproteinase 12 preproprotein | chr9p21.2 | Hs.128905 | MOB1, Mps One Binder kinase activator-like 2B (yeast) | MOBKL2B |
| 226818_at | T64884 | gb: AI375115 /DB_XREF = gi: 4175105 /DB_XREF = tc09e10.x1 /CLONE = IMAGE: 2063370 /FEA = EST /CNT = 43 /TID = Hs.293849.0 /TIER = Stack /STK = 27 /UG = Hs.293849 /UG_TITLE = ESTs | chr11q12.1 | Hs.62264 | macrophage expressed gene 1 | MPEG1 |
| 204438_at | NM_002438 | gb: T64884 /DB_XREF = gi: 673929 /DB_XREF = yd10b06.s1 /CLONE = IMAGE: 66707 /FEA = mRNA /CNT = 72 /TID = Hs.288581.0 /TIER = Stack /STK = 8 /UG = Hs.288581 /UG_TITLE = Homo sapiens cDNA FLJ14296 fis, clone PLACE1008455 | chr10p13 | Hs.75182 | mannose receptor, C type 1 /// mannose receptor, C type 1-like 1 | MRC1 /// MRC1L1 |
| 1555728_a_at | AF354928 | gb: NM_002438.1 /DB_XREF = gi: 4505244 /GEN = MRC1 /FEA = FLmRNA /CNT = 64 /TID = Hs.75182.0 /TIER = FL + Stack /STK = 25 /UG = Hs.75182 /LL = 4360 /DEF = Homo sapiens mannose receptor, C type 1 (MRC1), mRNA. /PROD = mannose receptor, C type 1 /FL = gb: NM_002438.1 gb: J05550.1 | chr11q12 | Hs.325960 | membrane-spanning 4-domains, subfamily A, member 4 | MS4A4A |
| 209949_at | BC001606 | gb: AF354928.1 /DB_XREF = gi: 15808758 /TID = Hs2.325960.4 /CNT = 1 /FEA = FLmRNA /TIER = FL /STK = 1 /LL = 51338 /UG_GENE = MS4A4A /UG = Hs.325960 /DEF = Homo sapiens MS4A4A protein mRNA, complete cds, alternatively spliced. /PROD = MS4A4A protein /FL = gb: AF354928.1 | chr1q25 | Hs.949 | neutrophil cytosolic factor 2 (65 kDa, chronic granulomatous disease, autosomal 2) | NCF2 |
| 221210_s_at | NM_030769 | gb: BC001606.1 /DB_XREF = gi: 12804408 /FEA = FLmRNA /CNT = 31 /TID = Hs.949.0 /TIER = FL /UG = Hs.949 /LL = 4688 /UG_GENE = NCF2 /DEF = Homo sapiens, Similar to neutrophil cytosolic factor 2 (65 kD, chronic granulomatous disease, autosomal 2), clone MGC: 2275, mRNA, co | chr1q25 | Hs.64896 | N-acetylneuraminate pyruvate lyase (dihydrodipicolinate synthase) /// N-acetylneuraminate pyruvate lyase (dihydrodipicolinate synthase) | NPL |
| 218625_at | NM_016588 | gb: NM_030769.1 /DB_XREF = gi: 13540532 /GEN = C1ORF13 /FEA = FLmRNA /CNT = 1 /TID = Hs.Affx.900046.172 /TIER = FL /STK = 0 /DEF = Homo sapiens hypothetical protein similar to swine acylneuraminate lyase (C1ORF13), mRNA. /PROD = hypothetical protein similar to swineacylneuram | chr6p25.1 | Hs.103291 | neuritin 1 | NRN1 |
| | | gb: NM_016588.1 /DB_XREF = gi: 7706122 /GEN = LOC51299 /FEA = FLmRNA /CNT = 106 /TID = Hs.103291.0 /TIER = FL + Stack /STK = 36 /UG = Hs.103291 /LL = 51299 /DEF = Homo sapiens neuritin (LOC51299), | | | | |

TABLE 1-continued

| Probe set ID number | Public ID number (NCBI) | Target description | Chromosomal location | Unigene ID | Gene Title | Gene Symbol |
|---|---|---|---|---|---|---|
| 231867_at | AB032953 | mRNA. /PROD = neuritin /FL = gb: NM_016588.1 gb: BC002683.1 gb: AF136631.1 gb: AB032953.1 /DB_XREF = gi: 6329762 /GEN = KIAA1127 /FEA = mRNA /CNT = 32 /TID = Hs.173560.0 /TIER = ConsEnd /STK = 2 /UG = Hs.173560 /LL = 57451 /DEF = Homo sapiens mRNA for KIAA1127 protein, partial cds. /PROD = KIAA1127 protein | chr5q34 | Hs.173560 | odz, odd Oz/ten-m homolog 2 (Drosophila) | ODZ2 |
| 226459_at | AW575754 | gb: AW575754 /DB_XREF = gi: 7247293 /DB_XREF = UI-HF-BM0-adw-c-06-0-UI.s1 /CLONE = IMAGE: 3063154 /FEA = EST /CNT = 60 /TID = Hs.86437.0 /TIER = Stack /STK = 35 /UG = Hs.86437 /UG_TITLE = ESTs, Highly similar to AF219140 1 gastric cancer-related protein GCYS-20 (H. sapiens) | chr10q24.1 | Hs.374836 | phosphoinositide-3-kinase adaptor protein 1 | PIK3AP1 |
| 206214_at | NM_005084 | gb: NM_005084.1 /DB_XREF = gi: 482683 /GEN = PLA2G7 /FEA = FLmRNA /CNT = 21 /TID = Hs.93304.0 /TIER = FL + Stack /STK = 8 /UG = Hs.93304 /LL = 7941 /DEF = Homo sapiens phospholipase A2, group VII (platelet-activating factor acetylhydrolase, plasma) (PLA2G7), mRNA. /PROD = phospho | chr6p21.2-p12 | Hs.93304 | phospholipase A2, group VII (platelet-activating factor acetylhydrolase, plasma) /// phospholipase A2, group VII (platelet-activating factor acetylhydrolase, plasma) | PLA2G7 |
| 212588_at | Y00062 | gb: Y00062.1 /DB_XREF = gi: 34275 /FEA = mRNA /CNT = 145 /TID = Hs.170121.1 /TIER = Stack /STK = 18 /UG = Hs.170121 /LL = 5788 /UG_GENE = PTPRC /UG_TITLE = protein tyrosine phosphatase, receptor type, C /DEF = Human mRNA for T200 leukocyte common antigen (CD45, LC-A). | chr1q31-q32 | Hs.444324 | protein tyrosine phosphatase, receptor type, C | PTPRC |
| 37793_r_at | AF034956 | Cluster Incl. AF034956: Homo sapiens RAD51D mRNA, complete cds /cds = (124,993) /gb = AF034956 /gi = 2920581 /ug = Hs.125244 /len = 1564 | chr17q11 | Hs.125244 | RAD51-like 3 (S. cerevisiae) | RAD51L3 |
| 203185_at | NM_014737 | gb: NM_014737.1 /DB_XREF = gi: 7761963 /GEN = RASSF2 /FEA = FLmRNA /CNT = 152 /TID = Hs.80905.0 /TIER = FL + Stack /STK = 30 /UG = Hs.80905 /LL = 9770 /DEF = Homo sapiens Ras association (RalGDS/AF-6) domain family 2 (RASSF2), mRNA. /PROD = Ras association (RalGDS/AF-6) domain famil | chr20pter-p12.1 | Hs.80905 | Ras association (RalGDS/AF-6) domain family 2 | RASSF2 |
| 225763_at | AI659418 | gb: AI659418 /DB_XREF = gi: 476988 /DB_XREF = tu30a07.x1 /CLONE = IMAGE: 2252532 /FEA = mRNA /CNT = 77 /TID = Hs.14040.0 /TIER = Stack /STK = 23 /UG = Hs.14040 /UG_TITLE = Homo sapiens cDNA: FLJ21772 fis, clone COLF7808 | chr1q22-q24 | Hs.233125 | RCSD domain containing 1 | RCSD1 |
| 213566_at | NM_005615 | gb: NM_005615.1 /DB_XREF = gi: 5032044 /GEN = RNASE6 /FEA = FLmRNA /CNT = 53 /TID = Hs.23262.0 /TIER = FL + Stack /STK = 30 /UG = Hs.23262 /LL = 6039 /DEF = Homo sapiens ribonuclease, RNase A family, k6 (RNASE6), mRNA. /PROD = ribonuclease, RNase A family, k6 /FL = gb: NM_005615.1 | chr14q11.2 | Hs.23262 | ribonuclease, RNase A family, k6 /// ribonuclease, RNase A family, k6 | RNASE6 |
| 219385_at | NM_020125 | gb: NM_020125.1 /DB_XREF = gi: 9910341 /GEN = SBBI42 /FEA = FLmRNA /CNT = 37 /TID = Hs.20450.0 /TIER = FL /STK = 0 /UG = Hs.20450 /LL = 56833 /DEF = Homo sapiens BCM-like membrane protein precursor (SBBI42), mRNA. /PROD = BCM-like membrane protein precursor /FL = gb: NM_020125.1 gb | chr1q23.2 | Hs.438683 | SLAM family member 8 | SLAMF8 |
| 203473_at | NM_007256 | gb: NM_007256.1 /DB_XREF = gi: 6005819 /GEN = SLC21A9 /FEA = FLmRNA /CNT = 120 /TID = Hs.7884.0 /TIER = FL + Stack /STK = 25 /UG = Hs.7884 /LL = 11309 /DEF = Homo sapiens solute carrier family 21 (organic anion transporter), member 9 (SLC21A9), mRNA. /PROD = solute carrier family | chr11q13 | Hs.7884 | solute carrier organic anion transporter family, member 2B1 | SLCO2B1 |
| 240715_at | AW269421 | gb: AW269421 /DB_XREF = gi: 6656451 /DB_XREF = xv42e03.x1 /CLONE = IMAGE: 2815804 /FEA = EST /CNT = 4 /TID = Hs.128093.0 /TIER = ConsEnd /STK = 4 /UG = Hs.128093 /UG_TITLE = ESTs | chr12q24.1 | Hs.381715 | T-box 5 | TBX5 |
| 205844_at | NM_004666 | gb: NM_004666.1 /DB_XREF = gi: 4759311 /GEN = VNN1 /FEA = FLmRNA | chr6q23-q24 | Hs.12114 | vanin 1 /// vanin 1 | VNN1 |

TABLE 1-continued

| Probe set ID number | Public ID number (NCBI) | Target description | Chromosomal location | Unigene ID | Gene Title | Gene Symbol |
|---|---|---|---|---|---|---|
| 205922_at | NM_004665 | /CNT = 36 /TID = Hs.12114.0 /TIER = FL + Stack /STK = 13 /UG = Hs.12114 /LL = 8876 /DEF = Homo sapiens vanin 1 (VNN1), mRNA. /PROD = vanin 1 /FL = gb: U39664.1 gb: NM_004666.1 gb: NM_004665.1 /DB_XREF = gi: 4759313 /GEN = VNN2 /FEA = FLmRNA /CNT = 24 /TID = Hs.121102.0 /TIER = FL + Stack /STK = 13 /UG = Hs.121102 /LL = 8875 /DEF = Homo sapiens vanin 2 (VNN2), mRNA. /PROD = vanin 2 /FL = gb: D89974.1 gb: NM_004665.1 | | | vanin 2 /// vanin 2 | VNN2 |
| 227346_at | AI741188 | gb: AI741188 /DB_XREF = gi: 5109476 /DB_XREF = wg26a11.x1 /CLONE = IMAGE: 2366204 /FEA = EST /CNT = 36 /TID = Hs.121587.0 /TIER = Stack /STK = 12 /UG = Hs.121587 /UG_TITLE = ESTs | | | Zinc finger protein, subfamily 1A, 1 (Ikaros) | ZNFN1A1 |
| 214836_x_at | BG536224 | gb: BG536224 /DB_XREF = gi: 13527769 /DB_XREF = 602565445F1 /CLONE = IMAGE: 4692058 /FEA = DNA /CNT = 36 /TID = Hs.123030.0 /TIER = ConsEnd /STK = 0 /UG = Hs.123030 /UG_TITLE = Human kappa-immunoglobulin germline pseudogene (Chr22.4) variable region (subgroup V kappa II) | | Hs.469271 /// Hs.525895 /// Hs.534006 | Immunoglobulin kappa light chain VJ region (ID POM010) /// Immunoglobulin kappa light chain VJ region (ID POM022) /// (clone TR.1.6VL) anti-thyroid peroxidase monoclonal autoantibody IgK chain, V region | — |
| 219947_at | NM_016184 | gb: NM_016184.1 /DB_XREF = gi: 7705337 /GEN = CLECSF6 /FEA = FLmRNA /CNT = 15 /TID = Hs.115515.0 /TIER = FL /STK = 7 /UG = Hs.115515 /LL = 50856 /DEF = Homo sapiens C-type (calcium dependent, carbohydrate-recognition domain) lectin, superfamily member 6 (CLECSF6), mRNA. /PROD= | chr12p13 | Hs.115515 | C-type (calcium dependent, carbohydrate-recognition domain) lectin, superfamily member 6 | CLECSF6 |
| | | | | | endothelial differentiation, sphingolipid G-protein-coupled receptor, 3 | EDG3 |
| | | | | | immunoglobulin heavy constant alpha 1 /// immunoglobulin heavy constant alpha 2 (A2m marker) /// hypothetical protein MGC27165 | IGHA1; IGHA2; MGC27165 |
| | | | | | mast cell-expressed membrane protein 1 | MCEMP1 |
| | | | | | protein kinase substrate MK2S4 | MK2S4 |

TABLE 2

| Probe set ID number | Public ID number (NCBI) | Target description | Chromosomal location | Unigene ID | Gene Title | Gene Symbol |
|---|---|---|---|---|---|---|
| 206046_at | NM_003812 | gb:NM_003812.1/DB_XREF = gi: 4501912/GEN = ADAM23/FEA = FLmRNA/CNT = 26/TID = Hs.7164.0/TIER = FL + Stack/STK = 11/UG = Hs.7164/LL = 8745/DEF = Homo sapiens a disintegrin and metalloproteinase domain 23 (ADAM23), mRNA./PROD = a disintegrin and metalloproteinase domain | chr2q33 | Hs.432317 | ADAM metallopeptidase domain 23 | ADAM23 |
| 206170_at | NM_000024 | gb:NM_000024.2/DB_XREF = gi: 13162366/GEN = ADRB2/FEA = FLmRNA/CNT = 35/TID = Hs.2551.0/TIER = FL/STK = 0/UG = Hs.2551/LL = 154/DEF = Homo sapiens adrenergic, beta-2-, receptor, surface (ADRB2), mRNA./PROD = adrenergic, beta-2-, receptor, surface/FL = gb: NM_000024.2 g | | Hs.89472 | adrenergic, beta-2-, receptor, surface | ADRB2 |
| 205357_s_at | NM_000685 | gb:NM_000685.2/DB_XREF = gi: 6715581/GEN = AGTR1/FEA = FLmRNA/CNT = 61/TID = Hs.89472.0/TIER = FL + Stack/STK = 18/UG = Hs.89472/LL = 185/DEF = Homo sapiens angiotensin receptor 1 (AGTR1), transcript variant 1, mRNA./PROD = angiotensin receptor 1/FL = gb: M93394.1 gb: NM_ | chr3q21-q25 | Hs.89472 | angiotensin II receptor, type 1 | AGTR1 |
| 216594_x_at | S68290 | gb:S68290.1/DB_XREF = gi: 544763/GEN = chlordecone reductase homolog/FEA = mRNA/CNT = 1/TID = Hs.306098.1/TIER = ConsEnd/STK = 0/UG = Hs.306098/LL = 1645/UG_TITLE = aldo-keto reductase family 1, member C1 (dihydrodiol dehydrogenase 1; 20-alpha (3-alpha)-hydroxystero | chr10p15-p14 | Hs.201967 | aldo-keto reductase family 1, member C1 (dihydrodiol dehydrogenase 1; 20-alpha (3-alpha)-hydroxysteroid dehydrogenase) | AKR1C1 |
| 209699_x_at | U05598 | gb:U05598.1/DB_XREF = gi: 531159/FEA = FLmRNA/CNT = 124/TID = Hs.201967.0/TIER = FL + Stack/STK = 29/UG = Hs.201967/LL = 1646/UG_GENE = AKR1C2/DEF = Human dihydrodiol dehydrogenase mRNA, complete cds./PROD = dihydrodiol dehydrogenase/FL = gb: U05598.1 gb:AB031083.1 gb: AB | chr10p15-p14 | Hs.201967 | aldo-keto reductase family 1, member C2 (dihydrodiol dehydrogenase 2; bile acid binding protein; 3-alpha hydroxysteroid dehydrogenase, type III) | AKR1C2 |
| 223093_at | T99215 | gb:T99215/DB_XREF = gi: 748952/DB_XREF = ye63a06.s1/CLONE = IMAGE: 122386/FEA = FLmRNA/CNT = 174/TID = Hs.168640.1/TIER = Stack/STK = 13/UG = Hs.168640/LL = 56172/UG_GENE = ANKH/UG_TITLE = ankylosis, progressive (mouse) homolog/FL = gb: AF274753.1 | chr5p15.1 | Hs.156727 | ankylosis, progressive homolog (mouse) | ANKH |
| 227827_at | AW138143 | gb:AW138143/DB_XREF = gi: 6142543/DB_XREF = UI-H-BI1-acy-b-09-0-UI.s1/CLONE = IMAGE: 2715976/FEA = EST/CNT = 32/TID = Hs.71721.0/TIER = Stack/STK = 16/UG = Hs.71721/UG_TITLE = ESTs | | | Sorbin and SH3 domain containing 2 | ARGBP2 |
| 230309_at | BE876610 | gb:BE876610/DB_XREF = gi: 10325386/DB_XREF = 60148767F1/CLONE = IMAGE: 3889936/FEA = EST/CNT = 13/TID = Hs.172382.1/TIER = Stack/STK = 11/UG = Hs.172382/LL = 23743/UG_GENE = BHMT2/UG_TITLE = betaine-homocysteine methyltransferase 2 | | | Betaine-homocysteine methyltransferase 2 | BHMT2 |
| 206176_at | NM_001718 | gb:NM_001718.2/DB_XREF = gi: 4809281/GEN = BMP6/FEA = FLmRNA/CNT = 18/TID = Hs.285671.0/TIER = FL/STK = 0/UG = Hs.285671/LL = 654/DEF = Homo sapiens bone morphogenetic protein 6 (BMP6), mRNA./PROD = bone morphogenetic protein 6 precursor/FL = gb: M60315.1 gb: NM_001718. | chr6p24-p23 | Hs.285671 | bone morphogenetic protein 6 | BMP6 |
| 241412_at | AI620677 | gb:AI620677/DB_XREF = gi: 4629803/DB_XREF = tu85e09.x1/CLONE = IMAGE: 2257864/FEA = EST/CNT = 7/TID = Hs.154191.0/TIER = ConsEnd/STK = 0/UG = Hs.154191/UG_TITLE = ESTs | chr4q13-q21 | Hs.73105 | betacellulin | BTC |
| 224458_at | BC006115 | gb:BC006115.1/DB_XREF = gi: 13543948/FEA = FLmRNA/CNT = 1/TID = HsAffx.900859.640/TIER = FL/STK = 0/DEF = Homo sapiens, Similar to RIKEN cDNA 2810432L12 gene, clone MGC: 12992, mRNA, complete cds./PROD = Similar to RIKEN cDNA 2810432L12 gene/FL = gb: BC006115.1 | chr9q31.1 | Hs.431270 | chromosome 9 open reading frame 125 /// chromosome 9 open reading frame 125 | C9orf125 |
| 235182_at | AI816793 | gb:AI816793/DB_XREF = gi: 5435872/DB_XREF = wj34b11.x1/CLONE = IMAGE: 2404701/FEA = EST/CNT = 13/TID = Hs.135100.0/TIER = ConsEnd/STK = 4/UG = Hs.135100/UG_TITLE = ESTs | chr20p12.1 | Hs.156650 | chromosome 20 open reading frame 82 | C20orf82 |

TABLE 2-continued

| Probe set ID number | Public ID number (NCBI) | Target description | Chromosomal location | Unigene ID | Gene Title | Gene Symbol |
|---|---|---|---|---|---|---|
| 227226_at | AA418816 | gb: AA418816 /DB_XREF = gi: 2080617 /DB_XREF = zw01a04.s1 /CLONE = IMAGE: 767982 /FEA = EST /CNT = 34 /TID = Hs.20953.0 /TIER = Stack /STK = 24 /UG = Hs.20953 /UG_TITLE = ESTs | chr6q14.3 | Hs.425033 | chromosome 6 open reading frame 117 | C6orf117 |
| 209616_s_at | S73751 | gb: S73751.1 /DB_XREF = gi: 688112 /FEA = FLmRNA /CNT = 178 /TID = Hs.76688.0 /TIER = FL /STK = 0 /UG = Hs.76688 /LL = 1066 /UG_GENE = CES1 /DEF = Homo sapiens acyl coenzyme A: cholesterol acyltransferase mRNA, complete cds. /PROD = acyl coenzyme A: cholesterol acyltransferase /FL | chr16q13-q22.1 | Hs.278997 | carboxylesterase 1 (monocyte/macrophage serine esterase 1) | CES1 |
| 208791_at | M25915 | gb: M25915.1 /DB_XREF = gi: 180619 /FEA = FLmRNA /CNT = 470 /TID = Hs.75106.0 /TIER = FL /STK = 3 /UG = Hs.75106 /LL = 1191 /UG_GENE = CLU /UG_TITLE = clusterin (complement lysis inhibitor, SP-40,40, sulfated glycoprotein 2, testosterone-repressed prostate message 2, apolipopr | chr8p21-p12 | Hs.436657 | clusterin (complement lysis inhibitor, SP-40,40, sulfated glycoprotein 2, testosterone-repressed prostate message 2, apolipoprotein J) | CLU |
| 205713_s_at | NM_000095 | gb: NM_000095.1 /DB_XREF = gi: 4557482 /GEN = COMP /FEA = FLmRNA /CNT = 64 /TID = Hs.1584.0 /TIER = FL + Stack /STK = 16 /UG = Hs.1584 /LL = 1311 /DEF = Homo sapiens cartilage oligomeric matrix protein (pseudoachondroplasia, epiphyseal dysplasia 1, multiple) (COMP), mRNA. /PROD = | chr19p13.1 | Hs.1584 | cartilage oligomeric matrix protein | COMP |
| 206315_at | NM_004750 | gb: NM_004750.1 /DB_XREF = gi: 4758061 /GEN = CRLF1 /FEA = FLmRNA /CNT = 20 /TID = Hs.114948.0 /TIER = FL + Stack /STK = 13 /UG = Hs.114948 /LL = 9244 /DEF = Homo sapiens cytokine receptor-like factor 1 /FL = gb: AF073515.1 gb: NM_004750.1, mRNA. /PROD = cytokine receptor-like factor 1 (CRLF1), | chr19p12 | Hs.114948 | cytokine receptor-like factor 1 | CRLF1 |
| 208350_at | NM_001890 | gb: NM_001890.1 /DB_XREF = gi: 4503084 /GEN = CSN1 /FEA = FLmRNA /CNT = 4 /TID = Hs.3155.0 /TIER = FL /STK = 0 /UG = Hs.3155 /LL = 1446 /DEF = Homo sapiens casein, alpha (CSN1), mRNA. /PROD = casein, alpha /FL = gb: NM_001890.1 gb: U23157.1 | chr4q21.1 | Hs.3155 | casein alpha s1 | CSN1S1 |
| 202435_s_at | AU154504 | gb: AU154504 /DB_XREF = gi: 11016025 /DB_XREF = AU154504 /CLONE = NT2RP4001328 /FEA = FLmRNA /CNT = 212 /TID = Hs.154654.0 /TIER = Stack /STK = 20 /UG = Hs.154654 /LL = 1545 /UG_GENE = CYP1B1 /UG_TITLE = cytochrome P450, subfamily I (dioxin-inducible), polypeptide 1 (glaucoma 3, p | chr2p21 | Hs.154654 | cytochrome P450, family 1, subfamily B, polypeptide 1 | CYP1B1 |
| 205818_at | NM_014618 | gb: NM_014618.1 /DB_XREF = gi: 7657008 /GEN = DBCCR1 /FEA = FLmRNA /CNT = 33 /TID = Hs.6090.0 /TIER = FL + Stack /STK = 8 /UG = Hs.6090 /LL = 1620 /DEF = Homo sapiens deleted in bladder cancer chromosome region candidate 1 (DBCCR1), mRNA. /PROD = deleted in bladder cancer chromoso | chr9q32-q33 | Hs.6090 | deleted in bladder cancer 1 | DBC1 |
| 210397_at | U73945 | gb: U73945.1 /DB_XREF = gi: 1755147 /FEA = FLmRNA /CNT = 26 /TID = Hs.32949.0 /TIER = FL /STK = 0 /UG = Hs.32949 /LL = 1672 /UG_GENE = DEFB1 /DEF = Human beta-defensin-1 mRNA, complete cds. /PROD = beta-defensin-1 /FL = gb: U73945.1 gb: NM_005218.2 | chr8p23.2-p23.1 | Hs.32949 | defensin, beta 1 | DEFB1 |
| 205554_s_at | NM_004944 | gb: NM_004944.1 /DB_XREF = gi: 4826697 /GEN = DNASE1L3 /FEA = FLmRNA /CNT = 51 /TID = Hs.88646.0 /TIER = FL /STK = 0 /UG = Hs.88646 /LL = 1776 /DEF = Homo sapiens deoxyribonuclease I-like 3 (DNASE1L3), mRNA. /PROD = deoxyribonuclease I-like 3 /FL = gb: U56814.1 gb: AF047354.1 gb: NM_ | chr3p21.1-3p14.3 | Hs.88646 | deoxyribonuclease I-like 3 | DNASE1L3 |
| 204014_at | NM_001394 | gb: NM_001394.2 /DB_XREF = gi: 12707552 /GEN = DUSP4 /FEA = FLmRNA /CNT = 105 /TID = Hs.2359.0 /TIER = FL /STK = 4 /UG = Hs.2359 /LL = 1846 /DEF = Homo sapiens dual specificity phosphatase 4 (DUSP4), mRNA. /PROD = dual specificity phosphatase 4 /FL = gb: NM_001394.2 gb: BC002671.1 g | chr8p12-p11 | Hs.417962 | dual specificity phosphatase 4 | DUSP4 |
| 204271_s_at | M74921 | gb: M74921.1 /DB_XREF = gi: 182275 /GEN = ETs /FEA = FLmRNA /CNT = 130 | chr13q22 | Hs.82002 | endothelin receptor type B | EDNRB |

TABLE 2-continued

| Probe set ID number | Public ID number (NCBI) | Target description | Chromosomal location | Unigene ID | Gene Title | Gene Symbol |
|---|---|---|---|---|---|---|
| 206070_s_at | AF213459 | /TID = Hs.82002.0 /TIER = FL/STK = 6 /UG = Hs.82002 /LL = 1910 /DEF = Human endothelin receptor mRNA, complete cds. /PROD = endothelin receptor /FL = gb: D90402.1 gb: NM_000115.1 gb: M74921.1 | | | | |
| 221884_at | BE466525 | gb: AF213459.1 /DB_XREF = gi: 12003434 /GEN = EPHA3 /FEA = FLmRNA /CNT = 20 /TID = Hs.123642.0 /TIER = FL /STK = 0 /UG = Hs.123642 /LL = 2042 /DEF = Homo sapiens ephrin receptor EPHA3 complete form (EPHA3) mRNA, complete cds. /PROD = ephrin receptor EPHA3 complete form /FL = gb: NM_ | chr3p11.2 | Hs.123642 | EPH receptor A3 | EPHA3 |
| 238877_at | BE674583 | gb: BE466525 /DB_XREF = gi: 9512223 /DB_XREF = hx9Ab10.x1 /CLONE = IMAGE: 3195451 /FEA = mRNA /CNT = 52 /TID = Hs.234773.0 /TIER = Stack /STK = 13 /UG = Hs.234773 /UG_TITLE = Homo sapiens cDNA: FLJ22281 fis, clone HRC03849, highly similar to S69002 human mRNA for AML1-EVI-1 | chr3q24-q28 | Hs.436019 | ecotropic viral integration site 1 | EVI1 |
| 202771_at | NM_014745 | gb: BE674583 /DB_XREF = gi: 10035124 /DB_XREF = 7e02h07.x1 /CLONE = IMAGE: 3281341 /FEA = EST /CNT = 7 /TID = Hs.102408.0 /TIER = ConsEnd /STK = 4 /UG = Hs.102408 /UG_TITLE = ESTs | | Hs.123642 | Eyes absent homolog 4 (Drosophila) | EYA4 |
| 227475_at | AI676059 | gb: NM_014745.1 /DB_XREF = gi: 7662013 /GEN = KIAA0233 /FEA = FLmRNA /CNT = 124 /TID = Hs.79077.0 /TIER = FL + Stack /STK = 53 /UG = Hs.79077 /LL = 9780 /DEF = Homo sapiens KIAA0233 gene product (KIAA0233), mRNA. /PROD = KIAA0233 gene product /FL = gb: D87071.1 gb: NM_014745.1 | chr16q24.3 | Hs.79077 | family with sequence similarity 38, member A | FAM38A |
| 219764_at | NM_007197 | gb: AI676059 /DB_XREF = gi: 4876539 /DB_XREF = wc04g08.x1 /CLONE = IMAGE: 2314238 /FEA = EST /CNT = 31 /TID = Hs.163900.0 /TIER = Stack /STK = 23 /UG = Hs.163900 /UG_TITLE = ESTs | chr6p25 | Hs.297452 | forkhead box Q1 | FOXQ1 |
| 227405_s_at | AW340311 | gb: NM_007197.1 /DB_XREF = gi: 6005761 /GEN = FZD10 /FEA = FLmRNA /CNT = 27 /TID = Hs.31664.0 /TIER = FL + Stack /STK = 16 /UG = Hs.31664 /LL = 11211 /DEF = Homo sapiens frizzled (Drosophila) homolog 10 (FZD10), mRNA. /PROD = frizzled (Drosophila) homolog 10 /FL = gb: AB027464.1 gb: N | chr12q24.33 | Hs.31664 | frizzled homolog 10 (Drosophila) | FZD10 |
| 208463_at | NM_000809 | gb: AW340311 /DB_XREF = gi: 6836937 /DB_XREF = hc95l03.x1 /CLONE = IMAGE: 2907773 /FEA = EST /CNT = 38 /TID = Hs.32659.0 /TIER = Stack /STK = 24 /UG = Hs.32659 /UG_TITLE = ESTs | chr10p11.21 | Hs.302634 | frizzled homolog 8 (Drosophila) | FZD8 |
| 218885_s_at | NM_024642 | gb: NM_000809.1 /DB_XREF = gi: 4557604 /GEN = GABRA4 /FEA = FLmRNA /CNT = 8 /TID = Hs.248112.0 /TIER = FL /STK = 0 /UG = Hs.248112 /LL = 2557 /DEF = Homo sapiens gamma-aminobutyric acid (GABA) A receptor, alpha 4 (GABRA4), mRNA. /PROD = gamma-aminobutyric acid A receptor, alpha | chr4p12 | Hs.248112 | gamma-aminobutyric acid (GABA) A receptor; alpha 4 | GABRA4 |
| 230360_at | AW006648 | gb: NM_024642.1 /DB_XREF = gi: 13375880 /GEN = FLJ21212 /FEA = FLmRNA /CNT = 70 /TID = Hs.47099.0 /TIER = FL /STK = 0 /UG = Hs.47099 /LL = 79695 /DEF = Homo sapiens hypothetical protein FLJ21212 (FLJ21212), mRNA. /PROD = hypothetical protein FLJ21212 /FL = gb: NM_024642.1 | chr9q22.33 | Hs.47099 | UDP-N-acetyl-alpha-D-galactosamine: polypeptide N-acetylgalactosaminyltransferase 12 (GalNAc-T12) | GALNT12 |
| 206355_at | R20102 | gb: AW006648 /DB_XREF = gi: 5855426 /DB_XREF = wr06e01.x1 /CLONE = IMAGE: 2506680 /FEA = EST /CNT = 10 /TID = Hs.30484.0 /TIER = Stack /STK = 8 /UG = Hs.30484 /UG_TITLE = ESTs | chr15q21.2 | Hs.30484 | gliomedin | GLDN |
| 227769_at | AI703476 | gb: R20102 /DB_XREF = gi: 774736 /DB_XREF = yg39h06.r1 /CLONE = IMAGE: 35031 /FEA = FLmRNA /CNT = 20 /TID = Hs.288642.0 /TIER = ConsEnd /STK = 0 /UG = Hs.288642 /LL = 2774 /UG_GENE = GNAL /UG_TITLE = guanine nucleotide binding protein (G protein), alpha activating activity polypept | chr18p11.22-p11.21 | Hs.136295 | guanine nucleotide binding protein (G protein), alpha activating activity polypeptide, olfactory type | GNAL |
| | | gb: AI703476 /DB_XREF = gi: 4991376 /DB_XREF = we24f08.x1 /CLONE = IMAGE: 2342055 /FEA = EST /CNT = 30 /TID = Hs.250899.0 /TIER = Stack /STK = 17 /UG = Hs.250899 /LL = 3281 /UG_GENE = HSBP1 /UG_TITLE = heat shock factor binding protein 1 | | | G protein-coupled receptor 27 | GPR27 |

TABLE 2-continued

| Probe set ID number | Public ID number (NCBI) | Target description | Chromosomal location | Unigene ID | Gene Title | Gene Symbol |
|---|---|---|---|---|---|---|
| 206002_at | NM_005756 | gb: NM_005756.1 /DB_XREF = gi: 5031732 /GEN = GPR64 /FEA = FLmRNA /CNT = 24 /TID = Hs.184942.0 /TIER = FL + Stack /STK = 9 /UG = Hs.184942 /LL = 10149 /DEF = Homo sapiens G protein-coupled receptor 64 (GPR64), mRNA. /PROD = G protein-coupled receptor 64 /FL = gb: NM_005756.1 | chrxp22.13 | Hs.421137 | G protein-coupled receptor 64 | GPR64 |
| 201348_at | NM_002084 | gb: NM_002084.2 /DB_XREF = gi: 606000 /GEN = GPX3 /FEA = FLmRNA /CNT = 468 /TID = Hs.172153.0 /TIER = FL + Stack /STK = 256 /UG = Hs.172153 /LL = 2878 /DEF = Homo sapiens glutathione peroxidase 3 (plasma) (GPX3), mRNA. /PROD = plasma glutathione peroxidase 3 precursor /FL = gb: NM_0 | chr5q23 | Hs.386793 | glutathione peroxidase 3 (plasma) | GPX3 |
| 218959_at | NM_017409 | gb: NM_017409.1 /DB_XREF = gi: 8393550 /GEN = HOXC10 /FEA = FLmRNA /CNT = 63 /TID = Hs.44276.0 /TIER = FL + Stack /STK = 18 /UG = Hs.44276 /LL = 3226 /DEF = Homo sapiens homeo box C10 (HOXC10), mRNA. /PROD = homeo box C10 /FL = gb: BC001293.1 gb: NM_017409.1 | chr12q13.3 | Hs.44276 | homeo box C10 | HOXC10 |
| 208937_s_at | D13889 | gb: D13889.1 /DB_XREF = gi: 464181 /GEN = Id-1H /FEA = FLmRNA /CNT = 355 /TID = Hs.75424.1 /TIER = FL /STK = 0 /UG = Hs.75424 /LL = 3397 /DEF = Human mRNA for Id-1H, complete cds. /PROD = Id-1H /FL = gb: NM_002165.1 gb: BC000613.1 gb: D13889.1 gb: AF255675.1 | chr20q11 | Hs.410900 | inhibitor of DNA binding 1, dominant negative helix-loop-helix protein | ID1 |
| 211430_s_at | M87789 | gb: M87789.1 /DB_XREF = gi: 185361 /FEA = FLmRNA /CNT = 1 /TID = Hs.300697.0 /TIER = FL /STK = 0 /UG = Hs.300697 /LL = 3502 /UG_GENE = IGHG3 /DEF = Human (hybridoma H210) anti-hepatitis A IgG variable region, constant region, complementarity-determining regions mRNA, complete | chr14q32.33 | Hs.413826 | immunoglobulin heavy locus /// immunoglobulin heavy constant gamma 1 (G1m marker) /// immunoglobulin heavy constant gamma 2 (G2m marker) /// immunoglobulin heavy constant gamma 3 (G3m marker) /// immunoglobulin heavy constant mu | IGH@ /// IGHG1 /// IGHG2 /// IGHG3 /// IGHM |
| 212592_at | AV733266 | gb: AV733266 /DB_XREF = gi: 10850811 /DB_XREF = AV733266 /CLONE = cdAAIG04 /FEA = EST /CNT = 270 /TID = Hs.76325.1 /TIER = Stack /STK = 67 /UG = Hs.76325 /LL = 10569 /UG_GENE = SLU7 /UG_TITLE = step II splicing factor SLU7 | chr4q21 | Hs.381568 | Immunoglobulin J polypeptide, linker protein for immunoglobulin alpha and mu polypeptides | IGJ |
| 209138_x_at | M87790 | gb: M87790.1 /DB_XREF = gi: 185363 /FEA = FLmRNA /CNT = 660 /TID = Hs.181125.0 /TIER = FL + Stack /STK = 584 /UG = Hs.181125 /LL = 3535 /UG_GENE = IGL@ /DEF = Human (hybridoma H210) anti-hepatitis A immunoglobulin lambda chain variable region, constant region, complementarity-de | chr22q11.2 | Hs.458262 | Immunoglobulin lambda joining 3 | IGLC2 |
| 206766_at | AF112345 | gb: AF112345.1 /DB_XREF = gi: 6650627 /GEN = ITGA10 /FEA = FLmRNA /CNT = 13 /TID = Hs.158237.0 /TIER = FL /STK = 0 /UG = Hs.158237 /LL = 8515 /DEF = Homo sapiens integrin alpha 10 subunit (ITGA10) mRNA, complete cds. /PROD = integrin alpha 10 subunit /FL = gb: AF112345.1 gb: NM_0036 | chr1q21 | Hs.158237 | integrin, alpha 10 | ITGA10 |
| 214927_at | AL359052 | gb: AL359052.1 /DB_XREF = gi: 8518175 /FEA = mRNA /CNT = 13 /TID = Hs.311054.0 /TIER = ConsEnd /STK = 5 /UG = Hs.311054 /DEF = Homo sapiens mRNA full length insert cDNA clone EUROIMAGE 1968422. /PROD = ITGBL1, integrin beta-like 1 | | | Integrin, beta-like 1 (with EGF-like repeat domains) | ITGBL1 |
| 221841_s_at | BF514079 | gb: BF514079 /DB_XREF = gi: 11599258 /DB_XREF = UI-H-BW1-anw-b-08-0-UI.s1 /CLONE = IMAGE: 3071198 /FEA = EST /CNT = 61 /TID = Hs.7934.1 /TIER = Stack /STK = 11 /UG = Hs.7934 /LL = 9314 /UG_GENE = KLF4 /UG_TITLE = Kruppel-like factor 4 (gut) | chr9q31 | Hs.376206 | Kruppel-like factor 4 (gut) | KLF4 |
| 204249_s_at | NM_005574 | gb: NM_005574.2 /DB_XREF = gi: 6633806 /GEN = LMO2 /FEA = FLmRNA /CNT = 93 /TID = Hs.184585.0 /TIER = FL + Stack /STK = 42 /UG = Hs.184585 /LL = 4005 /DEF = Homo sapiens LIM domain only 2 (rhombotin-like 1) (LMO2), | chr11p13 | Hs.283063 | LIM domain only 2 (rhombotin-like 1) | LMO2 |

TABLE 2-continued

| Probe set ID number | Public ID number (NCBI) | Target description | Chromosomal location | Unigene ID | Gene Title | Gene Symbol |
|---|---|---|---|---|---|---|
| 228653_at | AI700341 | mRNA. /PROD = LIM domain only 2 /FL = gb: NM_005574.2 gb: AI700341 /DB_XREF = gi: 4998241 /DB_XREF = wd06e10.x1 /CLONE = IMAGE: 2327370 /FEA = EST /CNT = 23 /TID = Hs.110406.0 /TIER = Stack /STK = 14 /UG = Hs.110406 /UG_TITLE = ESTs | | | SAM domain containing 1 | LOC389432 |
| 206953_s_at | NM_012302 | gb: NM_012302.1 /DB_XREF = gi: 6912463 /GEN = KIAA0786 /FEA = FLmRNA /CNT = 8 /TID = Hs.24212.0 /TIER = FL /STK = 0 /UG = Hs.24212 /LL = 23266 /DEF = Homo sapiens latrophilin (KIAA0786), mRNA. /PROD = latrophilin /FL = gb: NM_012302.1 gb: AF104939.1 | chr1p31.1 | Hs.24212 | latrophilin 2 | LPHN2 |
| 231781_s_at | AK021919 | gb: AK021919.1 /DB_XREF = gi: 10433216 /FEA = FLmRNA /CNT = 13 /TID = Hs.125790.2 /TIER = ConsEnd /STK = 0 /UG = Hs.125790 /LL = 79442 /UG_GENE = LRRC2 /UG_TITLE = leucine-rich repeat-containing 2 /DEF = Homo sapiens cDNA FLJ11857 fis, clone HEMBA1006807, moderately similar to H | chr3p21.31 | Hs.380055 | leucine rich repeat containing 2 | LRRC2 |
| 210302_s_at | AF262032 | gb: AF262032.1 /DB_XREF = gi: 9964006 /GEN = MAB21L2 /FEA = FLmRNA /CNT = 17 /TID = Hs.251390.0 /TIER = FL /STK = 0 /UG = Hs.251390 /LL = 10586 /DEF = Homo sapiens MAB21L2 protein (MAB21L2) mRNA, complete cds. /PROD = MAB21L2 protein /FL = gb: AF262032.1 gb: NM_006439.2 | chr4q31 | Hs.251390 | mab-21-like 2 (C. elegans) | MAB21L2 |
| 202291_s_at | NM_000900 | gb: NM_000900.1 /DB_XREF = gi: 4505178 /GEN = MGP /FEA = FLmRNA /CNT = 227 /TID = Hs.279009.0 /TIER = FL + Stack /STK = 84 /UG = Hs.279009 /LL = 4256 /DEF = Homo sapiens matrix Gla protein (MGP), mRNA. /PROD = matrix Gla protein /FL = gb: NM_000900.1 gb: M58549.1 | chr12p13.1-p12.3 | Hs.365706 | matrix Gla protein | MGP |
| 205680_at | NM_002425 | gb: NM_002425.1 /DB_XREF = gi: 4505204 /GEN = MMP10 /FEA = FLmRNA /CNT = 29 /TID = Hs.2258.0 /TIER = FL /STK = 6 /UG = Hs.2258 /LL = 4319 /DEF = Homo sapiens matrix metalloproteinase 10 (stromelysin 2) (MMP10), mRNA. /PROD = matrix metalloproteinase 10 preproprotein /FL = gb: NM_000900.1 gb: BC002 | chr11q22.3 | Hs.2258 | matrix metallopeptidase 10 (stromelysin 2) | MMP10 |
| 205330_at | NM_002430 | gb: NM_002430.1 /DB_XREF = gi: 4505222 /GEN = MN1 /FEA = FLmRNA /CNT = 43 /TID = Hs.268515.0 /TIER = FL + Stack /STK = 15 /UG = Hs.268515 /LL = 4330 /DEF = Homo sapiens meningioma (disrupted in balanced translocation) 1 (MN1), mRNA. /PROD = meningioma 1 /FL = gb: NM_002430.1 | chr22q12.1 | Hs.268515 | meningioma (disrupted in balanced translocation) 1 | MN1 |
| 213924_at | BF476502 | gb: BF476502 /DB_XREF = gi: 11547329 /DB_XREF = naa27a03.x1 /CLONE = IMAGE: 3255844 /FEA = EST /CNT = 16 /TID = Hs.154145.3 /TIER = Stack /STK = 9 /UG = Hs.154145 /LL = 65258 /UG_GENE = FLJ11585 /UG_TITLE = hypothetical protein FLJ11585 | | | Metallophosphoesterase 1 | MPPE1 |
| 212096_s_at | AL096842 | gb: AL096842.1 /DB_XREF = gi: 5524930 /FEA = mRNA /CNT = 243 /TID = Hs.7946.0 /TIER = Stack /STK = 99 /UG = Hs.7946 /LL = 57509 /UG_GENE = KIAA1288 /UG_TITLE = KIAA1288 protein /DEF = Homo sapiens mRNA; cDNA DKFZp586D1519 (from clone DKFZp586D1519). | chr8p22 | Hs.7946 | mitochondrial tumor suppressor 1 | MTUS1 |
| 217800_s_at | NM_030571 | gb: NM_030571.1 /DB_XREF = gi: 13386479 /GEN = MGC10924 /FEA = FLmRNA /CNT = 361 /TID = Hs.9788.0 /TIER = FL + Stack /STK = 152 /UG = Hs.9788 /LL = 80762 /DEF = Homo sapiens hypothetical protein MGC10924 similar to Nedd4 WW-binding protein 5 (MGC10924), mRNA. /PROD = hypothetical | chr5q31.3 | Hs.9788 | Nedd4 family interacting protein 1 | NDFIP1 |
| 223315_at | AF278532 | gb: AF278532.1 /DB_XREF = gi: 11120047 /FEA = FLmRNA /CNT = 97 /TID = Hs.102541.0 /TIER = FL + Stack /STK = 49 /UG = Hs.102541 /LL = 59277 /UG_GENE = NTN4 /DEF = Homo sapiens beta-netrin mRNA, complete cds. /PROD = beta-netrin /FL = gb: AF119916.1 gb: AF297711.1 gb: NM_021229.1 gb: AF27 | chr12q22-q23 | Hs.102541 | netrin 4 | NTN4 |
| 236088_at | AV723308 | gb: AV723308 /DB_XREF = gi: 10826596 /DB_XREF = AV723308 /CLONE = HTBBFC07 /FEA = EST /CNT = 11 /TID = Hs.171136.0 | chr1p13.3 | Hs.111224 | netrin G1 | NTNG1 |

TABLE 2-continued

| Probe set ID number | Public ID number (NCBI) | Target description | Chromosomal location | Unigene ID | Gene Title | Gene Symbol |
|---|---|---|---|---|---|---|
| 212582_at | AL049923 | /TIER = ConsEnd /STK = 2 /UG = Hs.171136 /UG_TITLE = ESTs gb: AL049923.1 /DB_XREF = gi: 4884169 /FEA = mRNA /CNT = 140 /TID = Hs.109694.0 /TIER = Stack /STK = 25 /UG = Hs.109694 /LL = 57601 /UG_GENE = KIAA1451 /UG_TITLE = KIAA1451 protein /DEF = *Homo sapiens* mRNA; cDNA DKFZp564E2282 (from clone DKFZp564E2282). | chr12q14 | Hs.109694 | oxysterol binding protein-like 8 | OSBPL8 |
| 223435_s_at | AI268404 | gb: AI268404 /DB_XREF = gi: 3887571 /DB_XREF = qm05e10.x1 /CLONE = IMAGE: 1880970 /FEA = FLmRNA /CNT = 73 /TID = Hs.167399.0 /TIER = Stack /STK = 13 /UG = Hs.167399 /LL = 56143 /UG_GENE = PCDHA5 /UG_TITLE = protocadherin alpha 5 /FL = gb: NM_018908.1 gb: AF152313.1 | chr5q31 | Hs.247734 | protocadherin alpha 9 /// protocadherin alpha subfamily C, 2 /// protocadherin alpha subfamily C, 1 /// protocadherin alpha 13 /// protocadherin alpha 12 /// protocadherin alpha 11 /// protocadherin alpha 10 /// protocadherin alpha 8 /// protocadherin alpha 7 /// protocadherin alpha 6 /// protocadherin alpha 5 /// protocadherin alpha 4 /// protocadherin alpha 3 /// protocadherin alpha 2 /// protocadherin alpha 1 | PCDHA9 /// PCDHAC2 /// PCDHAC1 /// PCDHA13 /// PCDHA12 /// PCDHA11 /// PCDHA10 /// PCDHA8 /// PCDHA7 /// PCDHA6 /// PCDHA5 /// PCDHA4 /// PCDHA3 /// PCDHA2 /// PCDHA1 |
| 1558680_s_at | BQ894022 | gb: BQ894022 /DB_XREF = gi: 22286036 /DB_XREF = AGENCOURT_8122690 /CLONE = IMAGE: 6180918 /TID = Hs2.383511.1 /CNT = 7 /FEA = mRNA /TIER = ConsEnd /STK = 0 /UG = Hs.383511 /UG_TITLE = *Homo sapiens* HSPDE1A mRNA for calmodulin-dependent phosphodiesterase, partial cds, N-terminal | chr2q32.1 | Hs.416061 | phosphodiesterase 1A, calmodulin-dependent | PDE1A |
| 208510_s_at | NM_015869 | gb: NM_015869.1 /DB_XREF = gi: 7705548 /GEN = PPARG /FEA = FLmRNA /CNT = 4 /TID = Hs.100724.1 /TIER = FL /STK = 0 /UG = Hs.100724 /LL = 5468 /DEF = *Homo sapiens* peroxisome proliferative activated receptor, gamma (PPARG), mRNA. /PROD = peroxisome proliferative activated receptorg | chr3p25 | Hs.387667 | peroxisome proliferative activated receptor, gamma | PPARG |
| 206007_at | NM_005807 | gb: NM_005807.1 /DB_XREF = gi: 5031924 /GEN = PRG4 /FEA = FLmRNA /CNT = 26 /TID = Hs.218791.0 /TIER = FL /STK = 0 /UG = Hs.218791 /LL = 10216 /DEF = *Homo sapiens* proteoglycan 4, (megakaryocyte stimulating factor, articular superficial zone protein) (PRG4), mRNA. /PROD = megakary | chr1q25-q31 | Hs.432458 | proteoglycan 4 | PRG4 |
| 206805_at | NM_006080 | gb: NM_006080.1 /DB_XREF = gi: 5174672 /GEN = SEMA3A /FEA = FLmRNA /CNT = 12 /TID = Hs.2414.0 /TIER = FL /STK = 0 /UG = Hs.2414 /LL = 10371 /DEF = *Homo sapiens* sema domain, immunoglobulin domain (Ig), short basic domain, secreted, (semaphorin) 3A (SEMA3A), mRNA. /PROD = sema dom | chr7p12.1 | Hs.252451 | sema domain, immunoglobulin domain (Ig), short basic domain, secreted, (semaphorin) 3A | SEMA3A |
| 206941_x_at | NM_012431 | gb: NM_012431.1 /DB_XREF = gi: 6912649 /GEN = SEMA3E /FEA = FLmRNA /CNT = 7 /TID = Hs.212414.0 /TIER = FL /STK = 0 /UG = Hs.212414 /LL = 9723 /DEF = *Homo sapiens* sema domain, immunoglobulin domain (Ig), short basic domain, secreted, (semaphorin) 3E (SEMA3E), mRNA. /PROD = sema d | chr7q21.11 | Hs.528721 | sema domain, immunoglobulin domain (Ig), short basic domain, secreted, (semaphorin) 3E | SEMA3E |
| 226492_at | AL036088 | gb: AL036088 /DB_XREF = gi: 5405713 /DB_XREF = DKFZp564J0223_s1 /CLONE = DKFZp564J0223 /FEA = mRNA /CNT = 49 /TID = Hs.191098.0 /TIER = Stack /STK = 19 /UG = Hs.191098 /LL = 57618 /UG_GENE = KIAA1479 /UG_TITLE = KIAA1479 protein | chr15q21.1 | Hs.191098 | sema domain, transmembrane domain (TM), and cytoplasmic domain, (semaphorin) 6D | SEMA6D |
| 223121_s_at | AW003584 | gb: AW003584 /DB_XREF = gi: 5850500 /DB_XREF = wq98h04.x1 /CLONE = IMAGE: 2480119 /FEA = FLmRNA /CNT = 207 /TID = Hs.31386.0 /TIER = Stack /STK = 26 /UG = Hs.31386 /LL = 6423 /UG_GENE = SFRP2 /UG_TITLE = secreted frizzled-related protein 2 /FL = gb: AF311912.1 | chr4q31.3 | Hs.31386 | secreted frizzled-related protein 2 | SFRP2 |

TABLE 2-continued

| Probe set ID number | Public ID number (NCBI) | Target description | Chromosomal location | Unigene ID | Gene Title | Gene Symbol |
|---|---|---|---|---|---|---|
| 206634_at | NM_005413 | gb: NM_005413.1 /DB_XREF = gi: 4885596 /GEN = SIX3 /FEA = FLmRNA /CNT = 14 /TID = Hs.227277.0 /TIER = FL /STK = 1 /UG = Hs.227277 /LL = 6496 /DEF = Homo sapiens sine oculis homeobox (Drosophila) homolog 3 (SIX3), mRNA. /PROD = sine oculis homeobox (Drosophila) homolog 3 /FL = gb: N | chr2p16-p21 | Hs.227277 | sine oculis homeobox homolog 3 (Drosophila) | SIX3 |
| 223044_at | AL136944 | gb: AL136944.1 /DB_XREF = gi: 12053382 /GEN = DKFZp586J0624 /FEA = FLmRNA /CNT = 341 /TID = Hs.5944.0 /TIER = FL + Stack /STK = 188 /UG = Hs.5944 /LL = 30061 /DEF = Homo sapiens mRNA; cDNA DKFZp586J0624 (from clone DKFZp586J0624); complete cds. /PROD = hypothetical protein /FL = gb: | chr2q32 | Hs.409875 | solute carrier family 40 (iron-regulated transporter), member 1 | SLC40A1 |
| 209921_at | AB040875 | gb: AB040875.1 /DB_XREF = gi: 13516845 /GEN = hxCT /FEA = FLmRNA /CNT = 45 /TID = Hs.6682.1 /TIER = FL + Stack /STK = 33 /UG = Hs.6682 /LL = 23657 /DEF = Homo sapiens hxCT mRNA for cystineglutamate exchanger, complete cds. /PROD = cystineglutamate exchanger /FL = gb: AB040875.1 | chr4q28-q32 | Hs.6682 | solute carrier family 7, (cationic amino acid transporter, y+ system) member 11 | SLC7A11 |
| 222784_at | AJ249900 | gb: AJ249900.1 /DB_XREF = gi: 10432430 /GEN = smoc1 /FEA = FLmRNA /CNT = 89 /TID = Hs.14144.0 /TIER = Stack /STK = 33 /UG = Hs.14144 /LL = 64093 /DEF = Homo sapiens mRNA for secreted modular calcium-binding protein (smoc1 gene). /PROD = secreted modular calcium-binding protein / | chr14q24.2 | Hs.14144 | SPARC related modular calcium binding 1 | SMOC1 |
| 227752_at | AA005105 | gb: AA005105 /DB_XREF = gi: 1448894 /DB_XREF = zh96f09.s1 /CLONE = IMAGE: 429161 /FEA = EST /CNT = 38 /TID = Hs.18441.0 /TIER = Stack /STK = 11 /UG = Hs.18441 /UG_TITLE = ESTs | chr3p25 | Hs.425023 | serine palmitoyltransferase, long chain base subunit 2-like (aminotransferase 2) | SPTLC2L |
| 203000_at | BF967657 | gb: BF967657 /DB_XREF = gi: 12334872 /DB_XREF = 602287358T1 /CLONE = IMAGE: 4374495 /FEA = FLmRNA /CNT = 403 /TID = Hs.90005.0 /TIER = Stack /STK = 18 /UG = Hs.90005 /LL = 11075 /UG_GENE = SCGN10 /UG_TITLE = superiorcervical ganglia, neural specific 10 /FL = gb: NM_007029.1 gb: D50375. | chr8q21.13 | Hs.90005 | stathmin-like 2 | STMN2 |
| 211276_at | AF063606 | gb: AF063606.1 /DB_XREF = gi: 12002041 /FEA = FLmRNA /CNT = 1 /TID = Hs.17481.0 /TIER = FL /STK = 0 /UG = Hs.17481 /DEF = Homo sapiens brain my048 protein mRNA, complete cds. /PROD = brain my048 protein /FL = gb: AF063606.1 | | | transcription elongation factor A (SII)-like 2 | TCEAL2 |
| 206243_at | NM_003256 | gb: NM_003256.1 /DB_XREF = gi: 4507514 /GEN = TIMP4 /FEA = FLmRNA /CNT = 25 /TID = Hs.190787.0 /TIER = FL + Stack /STK = 16 /UG = Hs.190787 /LL = 7079 /DEF = Homo sapiens tissue inhibitor of metalloproteinase 4 (TIMP4), mRNA. /PROD = tissue inhibitor of metalloproteinase 4precurso | chr3p25 | Hs.190787 | TIMP metallopeptidase inhibitor 4 | TIMP4 |
| 203661_s_at | BC002660 | gb: BC002660.1 /DB_XREF = gi: 12803650 /FEA = FLmRNA /CNT = 110 /TID = Hs.170453.0 /TIER = FL + Stack /STK = 19 /UG = Hs.170453 /LL = 7111 /UG_GENE = TMOD /DEF = Homo sapiens, tropomodulin, clone MGC: 3643, mRNA, complete cds. /PROD = tropomodulin /FL = gb: NM_003275.1 gb: M77016.1 gb: | chr9q22.3 | Hs.374849 | tropomodulin 1 | TMOD1 |
| 221085_at | NM_005118 | gb: NM_005118.1 /DB_XREF = gi: 4827031 /GEN = TNFSF15 /FEA = FLmRNA /CNT = 2 /TID = Hs.241382.0 /TIER = FL /STK = 0 /UG = Hs.241382 /LL = 9966 /DEF = Homo sapiens tumor necrosis factor (ligand) superfamily, member 15 (TNFSF15), mRNA. /PROD = tumor necrosis factor (ligand) super | chr9q32 | Hs.241382 | tumor necrosis factor (ligand) superfamily, member 15 | TNFSF15 |
| 202341_s_at | AA149745 | gb: AA149745 /DB_XREF = gi: 1720818 /DB_XREF = zo02h04.s1 /CLONE = IMAGE: 566551 /FEA = FLmRNA /CNT = 143 /TID = Hs.12372.0 /TIER = Stack /STK = 18 /UG = Hs.12372 /LL = 23321 /UG_GENE = KIAA0517 /UG_TITLE = tripartite motif protein TRIM2 /FL = gb: AF220018.1 gb: NM_015271.1 | chr4q31.3 | Hs.435734 | tripartite motif-containing 2 | TRIM2 |
| 242162_at | AA904430 | gb: AA904430 /DB_XREF = gi: 3039553 /DB_XREF = ok07f12.s1 | chr2q36.3 | Hs.424594 | WD repeat domain 69 | WDR69 |

TABLE 2-continued

| Probe set ID number | Public ID number (NCBI) | Target description | Chromosomal location | Unigene ID | Gene Title | Gene Symbol |
|---|---|---|---|---|---|---|
| 206373_at | NM_003412 | /CLONE = IMAGE:1507151 /FEA = EST /CNT = 5 /TID = Hs.122049.0 /TIER = ConsEnd /STK = 1 /UG = Hs.122049 /UG_TITLE = ESTs, Weakly similar to T2D4_HUMAN TRANSCRIPTION INITIATION FACTOR TFIID 100 KDA SUBUNIT (*H. sapiens*) gb: NM_003412.1 /DB_XREF = gi: 4507970 /GEN = ZIC1 /FEA = FLmRNA /CNT = 19 /TID = Hs.41154.0 /TIER = FL /STK = 7 /UG = Hs.41154 /LL = 7545 /DEF = *Homo sapiens* Zic family member 1 (odd-paired *Drosophila* homolog) (ZIC1), mRNA. /PROD = Zic family member 1 (odd-paired *Drosophila* homolog | | | Zic family member 1 (odd-paired homolog, *Drosophila*) | ZIC1 |
| 210910_s_at | BC000487 | gb: BC000487.1 /DB_XREF = gi: 12653432 /FEA = FLmRNA /CNT = 3 /TID = Hs.296380.1 /TIER = FL /STK = 0 /UG = Hs.296380 /LL = 22932 /UG_GENE = POMZP3 /DEF = *Homo sapiens*, Similar to POM (POM121 homolog, rat) and ZP3 fusion protein, clone MGC: 8359, mRNA, complete cds. /PROD = Similar homolog) and ZP3 fusion | chr7q11.23 | Hs.296380 | zona pellucida glycoprotein 3 (sperm receptor) /// POM (POM121 homolog, rat) and ZP3 fusion collomin | ZP3 /// POMZP3 COLM |

FULL CITATIONS FOR REFERENCES REFERRED TO IN THE SPECIFICATION

The following references, to the extent that they provide exemplary procedural or other details supplementary to those set forth herein, are specifically incorporated herein by reference.

1. Sayah A, English J C, 3rd. Rheumatoid arthritis: a review of the cutaneous manifestations. J Am Acad Dermatol 2005; 53(2):191-209.
2. Gabriel S E. The epidemiology of rheumatoid arthritis. Rheum Dis Clin North Am 2001; 27(2):269-81.
3. Lee D M, Weinblatt M E. Rheumatoid arthritis. Lancet 2001; 358(9285):903-11.
4. Ryan S. Rheumatology. Sharing care in an outpatient clinic. Nurs Stand 1995; 10(6):23-5.
5. Mor A, Abramson S B, Pillinger M H. The fibroblast-like synovial cell in rheumatoid arthritis: a key player in inflammation and joint destruction. Clin Immunol 2005; 115(2): 118-28.
6. Melnyk V O, Shipley G D, Sternfeld M D, Sherman L, Rosenbaum J T. Synoviocytes synthesize, bind, and respond to basic fibroblast growth factor. Arthritis Rheum 1990; 33(4):493-500.
7. Manabe N, Oda H, Nakamura K, Kuga Y, Uchida S, Kawaguchi H. Involvement of fibroblast growth factor-2 in joint destruction of rheumatoid arthritis patients. Rheumatology (Oxford) 1999; 38(8):714-20.
8. Allen J B, Manthey C L, Hand A R, Ohura K, Ellingsworth L, Wahl S M. Rapid onset synovial inflammation and hyperplasia induced by transforming growth factor beta. J Exp Med 1990; 171(1):231-47.
9. Ota F, Maeshima A, Yamashita S, Ikeuchi H, Kaneko Y, Kuroiwa T, et al. Activin A induces cell proliferation of fibroblast-like synoviocytes in rheumatoid arthritis. Arthritis Rheum 2003; 48(9):2442-9.
10. Gribi R, Tanaka T, Harper-Summers R, Yu J. Expression of activin A in inflammatory arthropathies. Mol Cell Endocrinol 2001; 180(1-2):163-7.
11. Sultan M, Wigle D A, Cumbaa C A, Maziarz M, Glasgow J, Tsao M S, et al. Binary tree-structured vector quantization approach to clustering and visualizing microarray data. Bioinformatics 2002; 18 Suppl 1:S111-9.
12. Kasperkovitz P V, Timmer T C, Smeets T J, Verbeet N L, Tak P P, van Baarsen L G, et al. Fibroblast-like synoviocytes derived from patients with rheumatoid arthritis show the imprint of synovial tissue heterogeneity: evidence of a link between an increased myofibroblast-like phenotype and high-inflammation synovitis. Arthritis Rheum 2005; 52(2):430-41.
13. Spurrell D R, Oldford S A, Frost T, Larsen B, Codner D, Edgecombe A, et al. Discordant expression of HLA class II-associated co-chaperones and HLA-DRB alleles in cultured fibroblast-like synoviocytes. Hum Immunol 2004; 65(12):1516-29.
14. Franke T F, Kaplan D R, Cantley L C. PI3K: downstream AKTion blocks apoptosis. Cell 1997; 88(4):435-7.
15. Cantley L C. The phosphoinositide 3-kinase pathway. Science 2002; 296(5573):1655-7.
16. Zhang H G, Wang Y, Xie J F, Liang X, Liu D, Yang P, et al. Regulation of tumor necrosis factor alpha-mediated apoptosis of rheumatoid arthritis synovial fibroblasts by the protein kinase Akt. Arthritis Rheum 2001; 44(7):1555-67.
17. Kim G, Jun J B, Elkon K B. Necessary role of phosphatidylinositol 3-kinase in transforming growth factor beta-mediated activation of Akt in normal and rheumatoid arthritis synovial fibroblasts. Arthritis Rheum 2002; 46(6): 1504-11.
18. Morel J, Audo R, Hahne M, Combe B. Tumor necrosis factor-related apoptosis-inducing ligand (TRAIL) induces rheumatoid arthritis synovial fibroblast proliferation through mitogen-activated protein kinases and phosphatidylinositol 3-kinase/Akt. J Biol Chem 2005; 280(16):15709-18.
19. Pritchard J, Tsui S, Horst N, Cruikshank W W, Smith T J. Synovial fibroblasts from patients with rheumatoid arthritis, like fibroblasts from Graves' disease, express high levels of IL-16 when treated with Igs against insulin-like growth factor-1 receptor. J Immunol 2004; 173(5):3564-9.
20. Hwang S Y, Kim J Y, Kim K W, Park M K, Moon Y, Kim W U, et al. IL-17 induces production of IL-6 and IL-8 in rheumatoid arthritis synovial fibroblasts via NF-kappaB- and PI3-kinase/Akt-dependent pathways. Arthritis Res Ther 2004; 6(2):R120-8.
21. Morel J C, Park C C, Zhu K, Kumar P, Ruth J H, Koch A E. Signal transduction pathways involved in rheumatoid arthritis synovial fibroblast interleukin-18-induced vascular cell adhesion molecule-1 expression. J Biol Chem 2002; 277(38):34679-91.
22. Nakayamada S, Okada Y, Saito K, Tamura M, Tanaka Y. Beta1 integrin/focal adhesion kinase-mediated signaling induces intercellular adhesion molecule 1 and receptor activator of nuclear factor kappaB ligand on osteoblasts and osteoclast maturation. J Biol Chem 2003; 278(46): 45368-74.
23. Scott B B, Zaratin P F, Gilmartin A G, Hansbury M J, Colombo A, Belpasso C, et al. TNF-alpha modulates angiopoietin-1 expression in rheumatoid synovial fibroblasts via the NF-kappa B signalling pathway. Biochem Biophys Res Commun 2005; 328(2):409-14.
24. Migita K, Miyashita T, Maeda Y, Aoyagi T, Kawabe Y, Nakamura M, et al. FK506 suppresses the stimulation of matrix metalloproteinase 13 synthesis by interleukin-1 beta in rheumatoid synovial fibroblasts. Immunol Lett 2005; 98(2):194-9.
25. Hammaker D R, Boyle D L, Chabaud-Riou M, Firestein G S. Regulation of c-Jun N-terminal kinase by MEKK-2 and mitogen-activated protein kinase kinase kinases in rheumatoid arthritis. J Immunol 2004; 172(3):1612-8.
26. Kawasaki H, Komai K, Nakamura M, Yamamoto E, Ouyang Z, Nakashima T, et al. Human wee1 kinase is directly transactivated by and increased in association with c-Fos/AP-1: rheumatoid synovial cells overexpressing these genes go into aberrant mitosis. Oncogene 2003; 22(44): 6839-44.
27. Nykanen P, Helve T, Kankaanpaa U, Larsen A. Characterization of the DNA-synthesizing cells in rheumatoid synovial tissue. Scand J Rheumatol 1978; 7(2):118-22.
28. Jacobs R A, Perrett D, Axon J M, Herbert K E, Scott D L. Rheumatoid synovial cell proliferation, transformation and fibronectin secretion in culture. Clin Exp Rheumatol 1995; 13(6):717-23.
29. Tsumuki H, Hasunuma T, Kobata T, Kato T, Uchida A, Nishioka K. Basic FGF-induced activation of telomerase in rheumatoid synoviocytes. Rheumatol Int 2000; 19(4): 123-8.
30. Yudoh K, Matsuno H, Nezuka T, Kimura T. Different mechanisms of synovial hyperplasia in rheumatoid arthritis and pigmented villonodular synovitis: the role of telom- 30. erase activity in synovial proliferation. Arthritis Rheum 1999; 42(4):669-77.
31. Dunphy J. The fibroblast-a unique ally for the surgeon. The New England Journal of Medicine 1963; 268:1367-77.
32. Quan T E, Cowper S, Wu S P, Bockenstedt L K, Bucala R. Circulating fibrocytes: collagen-secreting cells of the peripheral blood. Int J Biochem Cell Biol 2004; 36(4):598-606.
33. Phillips R J, Burdick M D, Hong K, Lutz M A, Murray L A, Xue Y Y, et al. Circulating fibrocytes traffic to the lungs in response to CXCL12 and mediate fibrosis. J Clin Invest 2004; 114(3):438-46.
34. Barth P J, Ebrahimsade S, Ramaswamy A, Moll R. CD34+ fibrocytes in invasive ductal carcinoma, ductal carcinoma in situ, and benign breast lesions. Virchows Arch 2002; 440(3):298-303.
35. Schmidt M, Sun G, Stacey M A, Mori L, Mattoli S. Identification of circulating fibrocytes as precursors of bronchial myofibroblasts in asthma. J Immunol 2003; 171(1):380-9.
36. Pilling D, Buckley C D, Salmon M, Gomer R H. Inhibition of fibrocyte differentiation by serum amyloid P. J Immunol 2003; 171(10):5537-46.
37. Mori L, Bellini A, Stacey M A, Schmidt M, Mattoli S. Fibrocytes contribute to the myofibroblast population in wounded skin and originate from the bone marrow. Exp Cell Res 2005; 304(1):81-90.
38. Abe R, Donnelly S C, Peng T, Bucala R, Metz C N. Peripheral blood fibrocytes: differentiation pathway and migration to wound sites. J Immunol 2001; 166(12):7556-62.
39. Bucala R, Spiegel L A, Chesney J, Hogan M, Cerami A. Circulating fibrocytes define a new leukocyte subpopulation that mediates tissue repair. Mol Med 1994; 1(1):71-81.
40. Chesney J, Bacher M, Bender A, Bucala R. The peripheral blood fibrocyte is a potent antigen-presenting cell capable of priming naive T cells in situ. Proc Natl Acad Sci USA 1997; 94(12):6307-12.
41. Reines B P. Is rheumatoid arthritis premature osteoarthritis with fetal-like healing? Autoimmun Rev 2004; 3(4): 305-11.
42. Buckley C D. Why does chronic inflammatory joint disease persist? Clin Med 2003; 3(4):361-6.
43. Mattey D L, Dawes P T, Nixon N B, Slater H. Transforming growth factor beta 1 and interleukin 4 induced alpha smooth muscle actin expression and myofibroblast-like differentiation in human synovial fibroblasts in vitro: modulation by basic fibroblast growth factor. Ann Rheum Dis 1997; 56(7):426-31.
44. Ruger B, Giurea A, Wanivenhaus A H, Zehetgruber H, Hollemann D, Yanagida G, et al. Endothelial precursor cells in the synovial tissue of patients with rheumatoid arthritis and osteoarthritis. Arthritis Rheum 2004; 50(7): 2157-66.
45. Kurosaka D, Yasuda J, Yoshida K, Yasuda C, Toyokawa Y, Yokoyama T, et al. Kinetics of circulating endothelial progenitor cells in mice with type II collagen arthritis. Blood Cells Mol Dis 2005.
46. Grisar J, Aletaha D, Steiner C W, Kapral T, Steiner S, Seidinger D, et al. Depletion of endothelial progenitor cells in the peripheral blood of patients with rheumatoid arthritis. Circulation 2005; 111(2):204-11.
47. Vittal R, Horowitz J C, Moore B B, Zhang H, Martinez F J, Toews G B, et al. Modulation of prosurvival signaling in fibroblasts by a protein kinase inhibitor protects against fibrotic tissue injury. Am J Pathol 2005; 166(2):367-75.
48. Horowitz J C, Lee D Y, Waghray M, Keshamouni V G, Thomas P E, Zhang H, et al. Activation of the pro-survival phosphatidylinositol 3-kinase/AKT pathway by transforming growth factor-beta1 in mesenchymal cells is mediated by p38 MAPK-dependent induction of an autocrine growth factor. J Biol Chem 2004; 279(2): 1359-67.
49. Mimura Y, Ihn H, Jinnin M, Asano Y, Yamane K, Tamaki K. Constitutive phosphorylation of focal adhesion kinase is involved in the myofibroblast differentiation of scleroderma fibroblasts. J Invest Dermatol 2005; 124(5):886-92.
50. Irish J M, Hovland R, Krutzik P O, Perez O D, Bruserud O, Gjertsen B T, et al. Single cell profiling of potentiated phospho-protein networks in cancer cells. Cell 2004; 118 (2):217-28.
51. Perez O D, Nolan G P. Simultaneous measurement of multiple active kinase states using polychromatic flow cytometry. Nat Biotechnol 2002; 20(2):155-62.
52. Perez O D, Mitchell D, Jager G C, South S, Murriel C, McBride J, et al. Leukocyte functional antigen 1 lowers T cell activation thresholds and signaling through cytohesin-1 and Jun-activating binding protein 1. Nat Immunol 2003; 4(11):1083-92.
53. Perez O D, Mitchell D, Jager G C, Nolan G P. LFA-1 signaling through p44/42 is coupled to perforin degranulation in CD56+CD8+ natural killer cells. Blood 2004; 104(4):1083-93.
54. Sachs K, Perez O, Pe'er D, Lauffenburger D A, Nolan G P. Causal protein-signaling networks derived from multiparameter single-cell data. Science 2005; 308(5721):523-9.
55. Kannan K, Ortmann, R A, Kimpel D. Animal models of rheumatoid arthritis and their relevance to human disease. Pathophysiology 2005; 12:167-181.
56. Holmdahl R, Bockermann R, Bäcklund J, Yamada H. The molecular pathogenesis of collagen-induced arthritis in mice—a model for rheumatoid arthritis. Ageing Research Reviews 2002; 1:135-147.

We claim:

1. A method of diagnosing or monitoring rheumatoid arthritis in a subject, comprising the steps:
   determining the activation state of a circulating CD3-CD45+collagen+ fibrocyte from a sample from the subject; and
   comparing the activation state of the fibrocyte from the sample with a control;
   wherein the activation state of the fibrocyte is determined by measuring the phosphorylation levels of signaling molecules, and
   wherein an increase in the activation state of the fibrocyte as compared to the control is indicative of rheumatoid arthritis.

2. The method according to claim 1, wherein the signaling molecules comprise STAT5.

3. The method according to claim 1, wherein the circulating fibrocyte further stains positive for CD14, CD34 and prolyl 4-hydroxylase.

4. A method of identifying a substance to treat rheumatoid arthritis, comprising the steps:
   (a) determining the activation state of circulating CD3-CD45+collagen+ fibrocytes from a sample from a subject administered the substance; and
   (b) comparing the activation state of the fibrocyte from the sample with a control;
   wherein the activation state of the fibrocyte is determined by measuring the phosphorylation levels of signaling molecules, and wherein a decrease in the activation state of the fibrocyte as compared to the control is indicative of a substance to treat rheumatoid arthritis.

5. The method according to claim 4, wherein the signaling molecules comprise STAT5.

6. The method according to claim 4, wherein the circulating fibrocytes further stains positive for CD14, CD34 and prolyl 4-hydroxylase.

* * * * *